United States Patent
Mjalli et al.

(10) Patent No.: US 8,853,226 B2
(45) Date of Patent: Oct. 7, 2014

(54) TRICYCLIC COMPOUNDS AS MODULATORS OF TNF-α SYNTHESIS AND AS PDE4 INHIBITORS

(75) Inventors: Adnan M. M. Mjalli, Oak Ridge, NC (US); Bapu Gaddam, High Point, NC (US); Dharma Rao Polisetti, High Point, NC (US); Matthew J. Kostura, Hillsborough, NC (US); Mustafa Guzel, Jamestown, NC (US)

(73) Assignee: High Point Pharmaceuticals, LLC, High Point, NC (US)

( * ) Notice: Subject to any disclaimer, the term of this patent is extended or adjusted under 35 U.S.C. 154(b) by 0 days.

(21) Appl. No.: 13/040,382

(22) Filed: Mar. 4, 2011

(65) Prior Publication Data

US 2011/0160234 A1    Jun. 30, 2011

Related U.S. Application Data

(63) Continuation of application No. 12/532,861, filed as application No. PCT/US2009/031819 on Jan. 23, 2009, now Pat. No. 7,964,608.

(60) Provisional application No. 61/023,617, filed on Jan. 25, 2008.

(51) Int. Cl.
*A61K 31/519* (2006.01)
*C07D 471/04* (2006.01)

(52) U.S. Cl.
CPC .................................. *C07D 471/04* (2013.01)
USPC ....................................................... 514/267

(58) Field of Classification Search
CPC .................................................. A61K 31/519
USPC ....................................................... 514/267
See application file for complete search history.

(56) References Cited

U.S. PATENT DOCUMENTS

| | | | |
|---|---|---|---|
| 4,927,820 A | 5/1990 | Shutske et al. | |
| 5,834,485 A | 11/1998 | Dyke et al. | |
| 8,329,715 B2 | 12/2012 | Mjalli et al. | |
| 2004/0171593 A1 | 9/2004 | Keating et al. | |
| 2005/0065116 A1 | 3/2005 | Carson et al. | |
| 2008/0255209 A1 | 10/2008 | Klein et al. | |
| 2012/0028932 A1 | 2/2012 | Nickolaus et al. | |
| 2012/0035143 A1 | 2/2012 | Nickolaus et al. | |

FOREIGN PATENT DOCUMENTS

| | | |
|---|---|---|
| EP | 0143001 A2 | 5/1985 |
| PL | 193012 B1 | 1/2007 |
| WO | WO 03/24489 | 3/2003 |
| WO | WO 03/062238 A1 | 7/2003 |
| WO | WO 2007/004958 A1 | 1/2007 |
| WO | WO 2011/124524 | 10/2011 |
| WO | WO 2011/124525 | 10/2011 |

OTHER PUBLICATIONS

Sturton, et al., Phosphodiesterase 4 Inhibitors for the Treatment of COPD, Chest, 121, 192S-196S (2002).*
Katritzky, et al., Polycyclic Heteroaromatics from Reactions of Acylbenzotriazoles with Aryl Isocyanates, J. Org. Chem., 65, 8069-8073 (2000).*
Chemical Abstracts Registry Entry 375362-97-3, entered Dec. 14, 2001.
Geis et al., "Tricyclic theophylline derivatives with high water-solubility: Structure-activity relationships at adenosine receptors, phosphodiesterases, and benzodiazepine binding sites," Pharmazie, vol. 50(5), pp. 333-336 (1995).
Haede, "Herstellung Kondensierter 2-Alkylthio-4-hydroxypyrimidine," J. Heterocyclic Chem., vol. 18(7), pp. 1417-1419 (1981).
Haider et al., "Product Class 9: Cinnolines," in Science of Synthesis, vol. 16, pp. 251-313 (2004).
International Preliminary Report on Patentability for PCT/US2009/031819, dated Jul. 27, 2010.
International Search Report for PCT/US2009/031819, dated Mar. 25, 2009.
Katritzky et al., "Polycyclic Heteroaromatics from Reactions of Acylbenzotriazoles with Aryl Isocyanates," Journal of Organic Chemistry, vol. 65(23), pp. 8069-8073 (2000).
Lewgowd et al., "Determination of Lipophilicity, pKa Measurement and Action on the Central Nervous System of Some Pyrimido[5,4-c]quinolines," Acta Poloniae Pharmaceutica—Drug Research, vol. 62(4), pp. 271-281 (2005).
Lewgowd et al., "Synthesis and Cytotoxicity of New Potential Intercalators Based on Tricyclic Systems of Some Pyrimido[5,4-c]cinnoline and Pyrimido[5,4-c]quinoline Derivatives. Part I," Acta Poloniae Pharmaceutica—Drug Research, vol. 62(2), pp. 105-110 (2005).
Menon et al., "Synthesis and Antimicrobial Properties of Pyrimido[5,4-c]cinolin-2,4(1H,3H)-diones," J. Indian Chem. Soc., vol. 72(10), pp. 731-733 (1995).
Nargund, et al., "Synthesis and Antimicrobial and Anti-inflammatory Activities of Substituted 2-Mercapto-3-(N-aryl)pyrimido[5,4-c]cinnolin-4-(3H)-ones," J. Pharm. Sci., vol. 81(4), pp. 365-366 (1992).
Reimund et al., "Anti-TNF-alpha Properties of New 9-Benzyladenine Derivatives with Selective Phosphodiesterase-4-Inhibiting Properties," Biochemical and Biophysical Research Communications, vol. 288, pp. 427-434 (2001).
Shindo et al., "Synthesis of Heterocyclic Compounds Isosterically Related to Pyrazolo[4,3-c]quinolines as Benzodiazepine Receptor Ligands," Heterocycles, vol. 29(5), pp. 899-912 (1989).
Stanczak et al., "Comparison of pharmacophore cinnoline and quinoline systems on the basis of computer calculation and pharmacological screening of their condensed systems," Pharmazie, vol. 56(6), pp. 501-505 (2001).

(Continued)

*Primary Examiner* — Erich A Leeser
(74) *Attorney, Agent, or Firm* — Samuel B. Rollins

(57) ABSTRACT

The present invention relates to chemical compounds of Formula (I) are as herein defined, pharmaceutical compositions, and methods of use in the treatment of conditions or disorders mediated by TNF-α or by PDE4, including but not limited to rheumatoid arthritis.

11 Claims, No Drawings

(56) References Cited

OTHER PUBLICATIONS

Stanczak et al., "Determination of the Lipophilicity of Pyrimido[5,4-c]quinoline Derivatives by Reversed-Phase Thin-Layer Chromatography. Part 1. Lipophilicity of Pyrimido[5,4-c]quinolin-4(3H)-ones and 1,2,3,4-Tetrahydropyrimido[5,4-c]quinolin-2,4-diones," J. Planar Chromatography, vol. 15(3), pp. 169-176 (2002).

Stanczak et al., "Synthesis and biological activity of some 4-amino-3-cinnoline carboxylic acid derivatives," Pharmazie, vol. 53(3), pp. 156-161 (1998).

Zahran et al., "Synthesis of Some Pyrimidines and their Benzo-Derivatives via 6 pi-Electron Cyclization Reactions," Afinidad, vol. 52(460), pp. 415-418 (1995).

European Search Report for EP Application No. 09704760.9, mailed Dec. 13, 2011.

Landells et al., "ABiochemical and Functional Assessment of Monocyte Phosphodiesterase Activity in Healthy and Asthmatic Subjects,"0 Pulmonary Pharmacoly & Therapeutics, 13-231-239 (2000).

Office Action in related U.S. Appl. No. 13/410,628, mailed May 14, 2012.

Peter et al., "Inhibition of cyclooxygenase-2 prevents adverse effects induced by phosphodiesterase type 4 inhibitors in rats," British Journal of Pharmacology, 162:415-427 (2011).

Office Action for related Chinese Application No. 200980102961.0, dated Jan. 13, 2014.

Spina, "PDE4 inhibitors: current status," British Journal of Pharmacology 155:308-315 (2008).

Chinese Patent Office Action for related Chinese Patent Application No. 200980102961.0 dated Jun. 26, 2013.

* cited by examiner

TRICYCLIC COMPOUNDS AS MODULATORS OF TNF-α SYNTHESIS AND AS PDE4 INHIBITORS

CROSS-REFERENCE TO RELATED APPLICATIONS

The present application is a continuation application of U.S. patent application Ser. No. 12/532,861, which is a United States national-stage application of PCT international application No. PCT/US2009/031819, filed Jan. 23, 2009, which claims the benefit of priority to U.S. Provisional Patent Application No. 61/023,617, filed Jan. 25, 2008. Each of the aforementioned applications is incorporated by reference in its entirety as though each were fully set forth herein.

FIELD OF THE INVENTION

The present invention relates to chemical compounds useful as inhibitors of the activity of tumor necrosis factor alpha (TNF-α) and as inhibitors of phosphodiesterase IV (PDE4), synthetic methods for their manufacture, and methods for use of such compounds.

BACKGROUND OF THE INVENTION

Tumor necrosis factor-alpha (TNF-α), also referred to as TNF, DIF, TNF-alpha, TNFA, and TNFSF2, is a cell-associated cytokine that is processed from a 26 kd precursor form to a 17 kd soluble form. TNF-α has been shown to be a primary mediator in humans and in animals of inflammation, fever, and acute phase responses, similar to those observed during acute infection and shock. Excess TNF-α has been shown to be lethal. There is now considerable evidence that blocking the effects of TNF-α by use of soluble TNF receptor or with specific neutralizing antibodies can be beneficial in a variety of circumstances including autoimmune diseases such as rheumatoid arthritis (RA), non-insulin dependent diabetes mellitus (NIDDM or Type II diabetes), and Crohn's disease.

Tumor necrosis factor (TNF) was first found in the serum of mice and rabbits infected with *Bacillus* Calmette-Guerin or injected with endotoxin, and was recognized on the basis of its cytotoxic, antitumor and metabolic properties. Many cell and tissues can produce TNF but its production is largely accomplished by macrophages and monocytes.

TNF can have a positive effect on the host organism by stimulating neutrophils and monocytes and by inhibiting the replication of viruses. Moreover, TNF-α activates the immune defenses against parasites and acts directly or indirectly as a mediator in immune reactions, inflammatory processes, and other processes in the body, although the mechanisms by which it works have not yet been clarified in a number of cases. The administration of TNF-α can also be accompanied by harmful phenomena such as shock and tissue damage, which can be remedied by means of antibodies against TNF-α.

TNF-α appears to be a mediator of cachexia which can occur in chronically invasive, for example, parasitic, diseases. TNF-α also appears to play a major part in the pathogenesis of shock caused by gram negative bacteria, for example, endotoxic shock; TNF-α would also appear to be implicated in some if not all the effects of lipopolysaccharides. TNF-α has also been postulated to have a function in the tissue damage which occurs in inflammatory processes in the joints and other tissues, and in the lethality and morbidity of the graft-versus host reaction (GVHR, Transplant Rejection). A correlation has also been reported between the concentration of TNF in the serum and the fatal outcome of meningococcal diseases.

The administration of TNF-α over a lengthy period causes a state of anorexia and malnutrition which has symptoms similar to those of cachexia, which accompany neoplastic and chronic infectious diseases.

A protein derived from the urine of fever patients has a TNF inhibiting activity; the effect of this protein is presumed to be due to a competitive mechanism at the level of the receptors (similar to the effect of the interleukin 1 inhibitor).

Anti-TNF-α antibodies (cA2) are effective in treating patients with rheumatoid arthritis (RA), which discovery led to an increased interest in finding novel TNF-α inhibitors as possible potent drugs for RA. Rheumatoid arthritis is an autoimmune chronic inflammatory disease characterized by irreversible pathological changes in the joints. In addition to RA, TNF-α antagonists may also be used in numerous pathological conditions and diseases. Some proofs indicating the biological importance of TNF-α were obtained by in vivo experiments in mice, in which mouse genes for TNF-α or its receptor were inactivated. Such animals are resistant to collagen-induced arthritis and to endotoxin-caused shock. In animal assays where the TNF-α level was increased, a chronic inflammatory polyarthritis occurred and its pathological picture was alleviated by inhibitors of TNF-α production. The treatment of such inflammatory and pathological conditions usually includes the application of non-steroid antiinflammatory drugs (NSAIDs) and, in more severe cases, gold salts, D-pencillinamine or methotrexate are administered. These drugs act symptomatically, but they do not stop the pathological process.

Novel approaches in the therapy of rheumatoid arthritis are based upon drugs such as tenidap, leflunomide, cyclosporin, FK-506 and upon biomolecules neutralizing the TNF-α action. Commercially available therapies include etanercept (Enbrel®, Immunex), a fusion protein of the soluble TNF-α receptor, and infliximab (Remicade®, Centocor), a chimeric monoclonal human and mouse antibody. Additionally, etanercept and infliximab are also registered for the therapy of Crohn's disease.

Compounds which inhibit the production of TNF-α are believed useful in a wide variety of diseases and disorders through mechanism based therapeutic intervention. TNF-α inhibitors are believed useful for diseases including but not limited to viral, alcoholic, or drug-induced acute and fulminant hepatitis, hepatic steatosis, both alcoholic and non-alcoholic, viral and non-viral hepatitis, hepatic cirrhosis, autoimmune hepatitis, chronic active hepatitis, Wilson's disease, myasthenia gravis, idiopathic sprue, autoimmune inflammatory bowel disease, ulcerative colitis, Crohn's disease, inflammatory bowel diseases, endocrine ophthalmopathy, Grave's disease, sarcoidosis, primary biliary cirrhosis, pancreatitis, nephritis, endotoxin shock, septic shock, haemodynamic shock, sepsis syndrome, post ischemic reperfusion injury, malaria, mycobacterial infection, meningitis, psoriasis, asthma, chronic obstructive pulmonary disease (COPD), eosinophilia, congestive heart failure, fibrotic diseases, cystic fibrosis, pulmonary fibrosis, hepatic fibrosis, renal fibrosis, cachexia, graft rejection, rejection by transplantation, cancer, diseases involving angiogenesis, autoimmune diseases, ankylosing spondylitis, autoimmune encephalomyelitis, autoimmune hematological disorders, hemolytic anemia, aplastic anemia, pure red cell anemia, idiopathic thrombocytopenia, systemic lupus erythematosus (SLE), polychondritis, scleroderma, Wegener granulomatosis, dermatomyositis, Reiter's syndrome, non infection uveitis, autoimmune keratitis, keratoconjunctivitis sicca, vernal keratoconjunctivitis, interstitial lung fibrosis, psoriatic arthritis, psoriasis and other benign or malignant proliferative skin diseases, atopic dermatitis, urticaria, neurodegenerative disorders, Parkinson's disease, Alzheimer's disease, acute and chronic multiple sclerosis, cancer, viral infection, human immunodeficiency virus (HIV), cachexia, thrombosis, skin inflammatory diseases, osteoarthritis (OA), osteoporosis, RA, emphysema, chronic bronchiolitis, allergic rhinitis, radiation damage, hyperoxic alveolar injury, periodontal disease, non-insulin dependent diabetes mellitus (Type II diabetes), and insulin dependent diabetes mellitus (Juvenile or Type I diabetes).

Phosphodiesterases (PDEs) comprise a superfamily of enzymes responsible for the hydrolysis and inactivation of the second messengers cyclic adenosine monophosphate (CAMP) and cyclic guanosine monophosphate (cGMP). Eleven different PDE families have been identified to date (PDE1 to PDE11) which differ in substrate preference, catalytic activity, sensitivity to endogenous activators and inhibitors, and encoding genes.

The PDE4 isoenzyme family exhibits a high affinity for cyclic AMP but has weak affinity for cyclic GMP. Increased cyclic AMP levels caused by PDE4 inhibition are associated with the suppression of cell activation in a wide range of inflammatory and immune cells, including lymphocytes, macrophages, basophils, neutrophils, and eosinophils. Moreover, PDE4 inhibition decreases the release of the cytokine Tumor Necrosis Factor-alpha (TNF-α).

In view of these physiological effects, PDE4 inhibitors of varied chemical structures have been recently disclosed for the treatment or prevention of chronic and acute inflammatory diseases and of other pathological conditions, diseases and disorders known to be susceptible to amelioration by inhibition of PDE4.

PDE4 are thought to be useful in the treatment and/or prophylaxis of a variety of diseases/conditions, especially inflammatory and/or allergic diseases, in mammals such as humans, for example: asthma, chronic obstructive pulmonary disease (COPD) (e.g. chronic bronchitis and/or emphysema), atopic dermatitis, urticaria, allergic rhinitis, allergic conjunctivitis, vernal conjunctivitis, eosinophilic granuloma, psoriasis, rheumatoid arthritis, septic shock, ulcerative colitis, Crohn's disease, reperfusion injury of the myocardium and brain, chronic glomerulonephritis, endotoxic shock, adult respiratory distress syndrome, multiple sclerosis, cognitive impairment (e.g. in a neurological disorder such as Alzheimer's disease), depression, or pain. Ulcerative colitis and/or Crohn's disease are collectively often referred to as inflammatory bowel disease.

SUMMARY OF THE INVENTION

The present invention includes a compound of Formula (I):

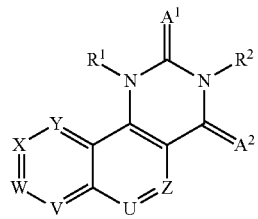

(I)

or a salt thereof, wherein
$A^1$ is O or S;
$A^2$ is O or S;
U is N or C—$(CH_2)_u R^U$;
V is N or C—$(CH_2)_v R^V$;
W is N or C—$(CH_2)_w R^W$;
X is N or C—$(CH_2)_x R^X$;
Y is N or C—$(CH_2)_y R^Y$;
Z is N or C—$(CH_2)_z R^Z$;
$R^1$ is —$(CH_2)_q R^Q$;
$R^2$ is —$(CH_2)_s R^S$;
wherein
  each of q, s, u, v, w, x, y, and z individually is 0, 1, 2, 3, or 4;
  each of $R^Q$, $R^S$, $R^U$, $R^V$, $R^W$, $R^X$, $R^Y$, and $R^Z$ is independently selected from the group consisting of
    alkyl;
    alkyl substituted with one or more $R^{ak}$;
    alkenyl;
    alkynyl;
    aryl;
    aryl substituted with one or more $R^a$;
    azido;
    cyano;
    cycloalkyl;
    cycloalkyl substituted with one or more $R^c$;
    fused cycloalkylaryl substituted with one or more $R^{f1}$;
    fused arylcycloalkyl substituted with one or more $R^{f2}$;
    fused heterocyclyaryl substituted with one or more $R^{f3}$;
    fused arylheterocyclyl substituted with one or more $R^{f4}$;
    fused cycloalkylheteroaryl substituted with one or more $R^{f5}$;
    fused heteroarylcycloalkyl substituted with one or more $R^{f6}$;
    fused heterocyclylheteroaryl substituted with one or more $R^{f7}$;
    fused heteroarylheterocyclyl substituted with one or more $R^{f8}$;
    halogen;
    haloalkyl;
    heterocyclyl;
    heterocyclyl substituted with one or more $R^{hc}$;
    heteroaryl;
    heteroaryl substituted with one or more $R^{ha}$;
    hydrogen;
    —$NR^3R^4$;
    —$C(O)NR^3R^4$;
    —$C(O)R^5$;
    —$C(O)_2R^6$;
    —$S(O)_jR^7$;
    —$OR^8$; and
    nitro;
  wherein
    each of $R^3$ and $R^4$ is independently selected from the group consisting of H, acyl, alkyl, alkoxy, alkoxyalkyl, alkylsulfonyl, aryl, cycloalkyl, heterocyclyl and heteroaryl;
    j is 0, 1, or 2;
    each $R^5$, $R^6$, $R^7$, and $R^8$ is independently selected from the group consisting of
      hydrogen;
      alkyl;
      alkyl substituted with one or more $R^{ak}$;
      alkenyl;
      alkynyl;
      alkoxy;
      aryl;

aryl substituted with one or more $R^a$;
cycloalkyl;
cycloalkyl substituted with one or more $R^c$;
halogen;
haloalkyl;
heterocyclyl;
heterocyclyl substituted with one or more $R^{hc}$;
heteroaryl;
heteroaryl substituted with one or more $R^{ha}$;
wherein each $R^a$, $R^c$, $R^{f1}$, $R^{f2}$, $R^{f3}$, $R^{f4}$, $R^{f5}$, $R^{f6}$, $R^{f7}$, $R^{hc}$ and $R^{ha}$ is independently selected from the group consisting of acyl, alkyl, alkenyl, alkynyl, alkoxy, amide, amino, aryl, cyano, cycloalkyl, halogen, haloalkyl, haloalkoxy, heteroaryl, hydroxy, nitro, $-C(O)OR^9$, $-SO_2R^{10}$, $-SR^{11}$, $-C(O)R^{12}$, $-C(O)NR^{13}$, $-NH-SO_2-R^{14}$, $-SO_2-NR^{15}R^{16}$, and $-SO_2-CH_2-SO_2-CH_3$; and wherein
each $R^9$, $R^{10}$, $R^{11}$, $R^{12}$, $R^{13}$, $R^{14}$, $R^{15}$, and $R^{16}$ is independently selected from the group consisting of hydrogen, alkyl, alkenyl, alkynyl, aryl, cycloalkyl, heterocyclyl, and heteroaryl,
provided that when $R^1$ is hydrogen, $R^S$ is selected from the group consisting of
alkyl;
alkyl substituted with one or more $R^{ak}$;
alkenyl;
alkynyl;
aryl;
aryl substituted with one or more $R^a$;
azido;
cyano;
cycloalkyl;
cycloalkyl substituted with one or more $R^c$;
fused cycloalkylaryl substituted with one or more $R^{f1}$;
fused arylcycloalkyl substituted with one or more $R^{f2}$;
fused heterocyclyaryl substituted with one or more $R^{f3}$;
fused arylheterocyclyl substituted with one or more $R^{f4}$;
fused cycloalkylheteroaryl substituted with one or more $R^{f5}$;
fused heteroarylcycloalkyl substituted with one or more $R^{f6}$;
fused heterocyclylheteroaryl substituted with one or more $R^{f7}$;
fused heteroarylheterocyclyl substituted with one or more $R^{f8}$;
heterocyclyl;
heterocyclyl substituted with one or more $R^{hc}$;
heteroaryl;
heteroaryl substituted with one or more $R^{ha}$;
$-NR^3R^4$;
$-C(O)NR^3R^4$;
$-C(O)R^5$;
$-C(O)_2R^6$;
$-S(O)_jR^7$;
$-OR^8$; and
nitro.

The present invention also provides pharmaceutical compositions comprising a compound of Formula (I) or a salt thereof.

In another embodiment, the present invention provides methods for the preparation of pharmaceutical compositions comprising a compound of Formula (I) or a salt thereof. The pharmaceutical compositions may further comprise a pharmaceutically acceptable carrier, excipient, diluent, or mixture thereof.

In another embodiment, the present invention provides methods for the use of a compound of Formula (I), or a salt thereof, and for the use of pharmaceutical compositions comprising a compound of Formula (I) or a salt thereof. The compounds and pharmaceutical compositions of the present invention may be used for the treatment of human or animal disorders.

Additional features of the present invention will be described hereinafter. It is to be understood that the invention is not limited in its application to the details set forth in the foregoing or following description but is capable of other embodiments and of being practiced or carried out in various ways.

DETAILED DESCRIPTION OF THE INVENTION

The following definitions are meant to clarify, but not limit, the terms defined. If a particular term used herein is not specifically defined, such term should not be considered indefinite. Rather, terms are used within their accepted meanings.

As used herein the term "alkyl" refers to a straight or branched chain hydrocarbon having one to twelve carbon atoms, which may be optionally substituted as herein further described, with multiple degrees of substitution being allowed. Examples of "alkyl" as used herein include, but are not limited to, methyl, ethyl, propyl, isopropyl, isobutyl, n-butyl, tert-butyl, isopentyl, and n-pentyl.

As used throughout this specification, the number of atoms, such as carbon atoms in an alkyl group, for example, will be represented by the phrase "$C_x$-$C_y$ alkyl," which refers to an alkyl group, as herein defined, containing the from x to y, inclusive, carbon atoms. Similar terminology will apply for other terms and ranges as well. One embodiment of the present invention includes so-called 'lower' alkyl chains of one to six carbon atoms. Thus, $C_1$-$C_6$ alkyl represents a lower alkyl chain as hereabove described.

As used herein the term "alkenyl" refers to a straight or branched chain aliphatic hydrocarbon having two to twelve carbon atoms and containing one or more carbon-to-carbon double bonds, which may be optionally substituted as herein further described, with multiple degrees of substitution being allowed. Examples of "alkenyl" as used herein include, but are not limited to, vinyl, and allyl.

As used herein the term "alkynyl" refers to a straight or branched chain aliphatic hydrocarbon having two to twelve carbon atoms and containing one or more carbon-to-carbon triple bonds, which may be optionally substituted as herein further described, with multiple degrees of substitution being allowed. An example of "alkynyl" as used herein includes, but is not limited to, ethynyl.

As used herein, the term "alkylene" refers to a straight or branched chain divalent hydrocarbon radical having from one to ten carbon atoms, which may be optionally substituted as herein further described, with multiple degrees of substitution being allowed. Examples of "alkylene" as used herein include, but are not limited to, methylene, ethylene, n-propylene, and n-butylene.

As used herein, the term "alkenylene" refers to a straight or branched chain divalent hydrocarbon radical having from two to ten carbon atoms and containing one or more carbon-to-carbon double bonds, which may be optionally substituted as herein further described, with multiple degrees of substitution being allowed. Examples of "alkenylene" as used herein include, but are not limited to, vinylene, allylene, and 2-propenylene.

As used herein, the term "alkynylene" refers to a straight or branched chain divalent hydrocarbon radical having from two to ten carbon atoms and containing one or more carbon-to-carbon triple bonds, which may be optionally substituted as herein further described, with multiple degrees of substitution being allowed. An example of "alkynylene" as used herein includes, but is not limited to, ethynylene.

As used herein, the term "cycloalkyl" refers to an optionally substituted non-aromatic, three- to twelve-membered, cyclic hydrocarbon ring, optionally containing one or more degrees of unsaturation, which may be optionally substituted as herein further described, with multiple degrees of substitution being allowed. Exemplary "cycloalkyl" groups as used herein include, but are not limited to, cyclopropyl, cyclobutyl, cyclopentyl, cyclohexyl, and cycloheptyl, as well as rings containing one or more degrees of unsaturation but short of aromatic, such as cyclopropenyl, cyclobutenyl, cyclopentenyl, cyclohexenyl, and cycloheptenyl.

As used herein, the term "cycloalkylene" refers to a divalent, non-aromatic cyclic hydrocarbon ring, which may be optionally substituted as herein further described, with multiple degrees of substitution being allowed. Exemplary "cycloalkylene" groups include, but are not limited to, cyclopropylene, cyclobutylene, cyclopentylene, cyclohexylene, cycloheptylene, and substituted versions thereof. The term is intended to encompass divalent rings having different points of attachment as well as a common point of attachment, which connecting atom may also be referred to as "spiroatom."

As used herein, the term "heterocycle" or "heterocyclyl" refers to an optionally substituted mono- or polycyclic ring system, optionally containing one or more degrees of unsaturation and also containing one or more heteroatoms, which may be optionally substituted as herein further described, with multiple degrees of substitution being allowed. Exemplary heteroatoms include nitrogen, oxygen, or sulfur atoms, including N-oxides, sulfur oxides, and sulfur dioxides. Typically, the ring is three to twelve-membered and is either fully saturated or has one or more degrees of unsaturation. Such rings may be optionally fused to one or more of another heterocyclic ring(s), cycloalkyl ring(s), aryl groups (as defined below) or heteroaryl groups (as defined below). Examples of "heterocyclic" groups as used herein include, but are not limited to, tetrahydrofuran, pyran, 1,4-dioxane, 1,3-dioxane, piperidine, pyrrolidine, morpholine, tetrahydrothiopyran, and tetrahydrothiophene.

As used herein, the term "aryl" refers to a univalent aromatic ring or fused ring system, which may be optionally substituted as herein further described, with multiple degrees of substitution being allowed. Examples of "aryl" groups as used include, but are not limited to, phenyl, 2-naphthyl, 1-naphthyl, anthracene, and phenanthrene.

As used herein, the term "heteroaryl" refers to a monocyclic five to seven membered aromatic ring, or to a fused bicyclic aromatic ring system comprising two of such aromatic rings, which may be optionally substituted as herein further described, with multiple degrees of substitution being allowed. These heteroaryl rings contain one or more nitrogen, sulfur, and/or oxygen atoms, where N-oxides, sulfur oxides, and dioxides are permissible heteroatom substitutions. Examples of "heteroaryl" groups as used herein include, but should not be limited to, furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzodioxolyl, benzothiophene, indole, indazole, benzimidazolyl, imidazopyridinyl, pyrazolopyridinyl, and pyrazolopyrimidinyl.

As used herein, the term "fused cycloalkylaryl" refers to one or two cycloalkyl groups fused to an aryl group, the aryl and cycloalkyl groups having two atoms in common, and wherein the aryl group is the point of substitution. Examples of "fused cycloalkylaryl" used herein include 5-indanyl, 5,6,7,8-tetrahydro-2-naphthyl,

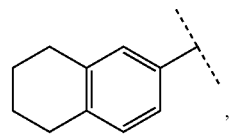

and the like.

As used herein, the term "fused arylcycloalkyl" refers to one or two aryl groups fused to a cycloalkyl group, the cycloalkyl and aryl groups having two atoms in common, and wherein the cycloalkyl group is the point of substitution. Examples of "fused arylcycloalkyl" used herein include 1-indanyl, 2-indanyl, 9-fluorenyl, 1-(1,2,3,4-tetrahydronaphthyl),

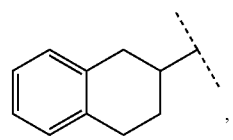

and the like.

As used herein, the term "fused heterocyclylacyl" refers to one or two heterocyclyl groups fused to an aryl group, the aryl and heterocyclyl groups having two atoms in common, and wherein the aryl group is the point of substitution. Examples of "fused heterocyclylacyl" used herein include 3,4-methylenedioxy-1-phenyl,

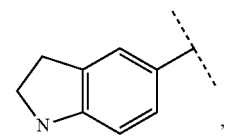

and the like.

As used herein, the term "fused arylheterocyclyl" refers to one or two aryl groups fused to a heterocyclyl group, the heterocyclyl and aryl groups having two atoms in common, and wherein the heterocyclyl group is the point of substitution. Examples of "fused arylheterocyclyl" used herein include 2-(1,3-benzodioxolyl),

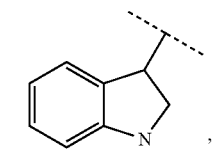

and the like.

As used herein, the term "fused cycloalkylheteroaryl" refers to one or two cycloalkyl groups fused to a heteroaryl group, the heteroaryl and cycloalkyl groups having two atoms in common, and wherein the heteroaryl group is the point of substitution. Examples of "fused cycloalkylheteroaryl" used herein include 5-aza-6-indanyl, and the like.

As used herein, the term "fused heteroarylcycloalkyl" refers to one or two heteroaryl groups fused to a cycloalkyl group, the cycloalkyl and heteroaryl groups having two atoms in common, and wherein the cycloalkyl group is the point of substitution. Examples of "fused heteroarylcycloalkyl" used herein include 5-aza-1-indanyl, and the like.

As used herein, the term "fused heterocyclylheteroaryl" refers to one or two heterocyclyl groups fused to a heteroaryl group, the heteroaryl and heterocyclyl groups having two atoms in common, and wherein the heteroaryl group is the point of substitution. Examples of "fused heterocyclylheteroaryl" used herein include 1,2,3,4-tetrahydro-beta-carbolin-8-yl, and the like.

As used herein, the term "fused heteroarylheterocyclyl" refers to one or two heteroaryl groups fused to a heterocyclyl group, the heterocyclyl and heteroaryl groups having two atoms in common, and wherein the heterocyclyl group is the point of substitution. Examples of "fused heteroarylheterocyclyl" used herein include -5-aza-2,3-dihydrobenzofuran-2-yl, and the like.

As used herein the term "alkoxy" refers to a group —OR$^a$, where R$^a$ is alkyl as defined above.

As used herein the term "halogen" refers to fluorine, chlorine, bromine, or iodine.

As used herein the term "haloalkyl" refers to an alkyl group, as defined herein, that is substituted with at least one halogen. Examples of branched or straight chained "haloalkyl" groups as used herein include, but are not limited to, methyl, ethyl, propyl, isopropyl, n-butyl, and t-butyl substituted independently with one or more halogens, for example, fluoro, chloro, bromo, and iodo. The term "haloalkyl" should be interpreted to include such substituents as perfluoroalkyl groups such as —CF$_3$.

As used herein, the term "haloalkylene" refers to a straight or branched chain divalent hydrocarbon radical, substituted with at least one halogen. The term should be interpreted to include perfluoroalkylene groups such as —CF$_2$—.

As used herein, the term "haloalkoxy" refers to a group —OR$^a$, where R$^a$ is a haloalkyl group as herein defined. As non-limiting examples, haloalkoxy groups include —O(CH$_2$)F, —O(CH)F$_2$, and —OCF$_3$.

As used herein the term "nitro" refers to a group —NO$_2$.

As used herein the term "cyano" refers to a group —CN.

As used herein the term "azido" refers to a group —N$_3$.

As used herein the term "amide" refers to a group —C(O)NR$^a$R$^b$ or —NR$^a$C(O)—, where each R$^a$ and R$^b$ individually is hydrogen, alkyl, alkenyl, alkynyl, cycloalkyl, aryl, heterocyclyl, or heteroaryl.

As used herein "amino" refers to a group —NR$^a$R$^b$, where each of R$^a$ and R$^b$ individually is hydrogen, alkyl, alkenyl, alkynyl, cycloalkyl, aryl, heterocyclyl, or heteroaryl. As used herein, when either R$^a$ or R$^b$ is other than hydrogen, such a group may be referred to as a "substituted amino" or, for example if R$^a$ is H and R$^b$ is alkyl, as an "alkylamino."

As used herein, the term "acyl" refers to a group —C(O)R$^a$, where R$^a$ is hydrogen, alkyl, alkenyl, alkynyl, cycloalkyl, aryl, heterocyclyl, or heteroaryl.

As used herein, the term "hydroxyl" refers to a group —OH.

As used herein, the term "substituted" refers to substitution of one or more hydrogens of the designated moiety with the named substituent or substituents, multiple degrees of substitution being allowed unless otherwise stated, provided that the substitution results in a stable or chemically feasible compound. A stable compound or chemically feasible compound is one in which the chemical structure is not substantially altered when kept at a temperature from about −80° C. to about +40° C., in the absence of moisture or other chemically reactive conditions, for at least a week, or a compound which maintains its integrity long enough to be useful for therapeutic or prophylactic administration to a patient. As used herein, the phrase "substituted with one or more . . . " refers to a number of substituents that equals from one to the maximum number of substituents possible based on the number of available bonding sites, provided that the above conditions of stability and chemical feasibility are met.

The present invention includes a compound of Formula (I):

(I)

or a salt thereof, wherein
A$^1$ is O or S;
A$^2$ is O or S;

U is N or C—$(CH_2)_u R^U$;
V is N or C—$(CH_2)_v R^V$;
W is N or C—$(CH_2)_w R^W$;
X is N or C—$(CH_2)_x R^X$;
Y is N or C—$(CH_2)_y R^Y$;
Z is N or C—$(CH_2)_z R^Z$;
$R^1$ is —$(CH_2)_q R^Q$;
$R^2$ is —$(CH_2)_s R^S$;
wherein
  each of q, s, u, v, w, x, y, and z individually is 0, 1, 2, 3, or 4;
  each of $R^Q$, $R^S$, $R^U$, $R^V$, $R^W$, $R^X$, $R^Y$, and $R^Z$ is independently selected from the group consisting of
    alkyl;
    alkyl substituted with one or more $R^{ak}$;
    alkenyl;
    alkynyl;
    aryl;
    aryl substituted with one or more $R^a$;
    azido;
    cyano;
    cycloalkyl;
    cycloalkyl substituted with one or more $R^c$;
    fused cycloalkylaryl substituted with one or more $R^{f1}$;
    fused arylcycloalkyl substituted with one or more $R^{f2}$;
    fused heterocyclyaryl substituted with one or more $R^{f3}$;
    fused arylheterocyclyl substituted with one or more $R^{f4}$;
    fused cycloalkylheteroaryl substituted with one or more $R^{f5}$;
    fused heteroarylcycloalkyl substituted with one or more $R^{f6}$;
    fused heterocyclylheteroaryl substituted with one or more $R^{f7}$;
    fused heteroarylheterocyclyl substituted with one or more $R^{f8}$;
    halogen;
    haloalkyl;
    heterocyclyl;
    heterocyclyl substituted with one or more $R^{hc}$;
    heteroaryl;
    heteroaryl substituted with one or more $R^{ha}$;
    hydrogen;
    —$NR^3R^4$;
    —$C(O)NR^3R^4$;
    —$C(O)R^5$;
    —$C(O)_2R^6$;
    —$S(O)_jR^7$;
    —$OR^8$; and
    nitro;
    wherein
      each of $R^3$ and $R^4$ is independently selected from the group consisting of H, acyl, alkyl, alkoxy, alkoxyalkyl, alkylsulfonyl, aryl, cycloalkyl, heterocyclyl and heteroaryl;
      j is 0, 1, or 2;
      each $R^5$, $R^6$, $R^7$, and $R^8$ is independently selected from the group consisting of
        hydrogen;
        alkyl;
        alkyl substituted with one or more $R^{ak}$;
        alkenyl;
        alkynyl;
        alkoxy;
        aryl;
        aryl substituted with one or more $R^a$;
        cycloalkyl;
        cycloalkyl substituted with one or more $R^c$;
        halogen;
        haloalkyl;
        heterocyclyl;
        heterocyclyl substituted with one or more $R^{hc}$;
        heteroaryl;
        heteroaryl substituted with one or more $R^{ha}$;
      wherein each $R^a$, $R^c$, $R^{f1}$, $R^{f2}$, $R^{f3}$, $R^{f4}$, $R^{f5}$, $R^{f6}$, $R^{f7}$, $R^{hc}$ and $R^{ha}$ is independently selected from the group consisting of acyl, alkyl, alkenyl, alkynyl, alkoxy, amide, amino, aryl, cyano, cycloalkyl, halogen, haloalkyl, haloalkoxy, heteroaryl, hydroxy, nitro, —$C(O)OR^9$, —$SO_2R^{10}$, —$SR^{11}$, —$C(O)R^{12}$, —$C(O)NR^{13}$, —$NH$—$SO_2$—$R^{14}$, —$SO_2$—$NR^{15}R^{16}$, and —$SO_2$—$CH_2$—$SO_2$—$CH_3$; and wherein
        each $R^9$, $R^{10}$, $R^{11}$, $R^{12}$, $R^{13}$, $R^{14}$, $R^{15}$, and $R^{16}$ is independently selected from the group consisting of hydrogen, alkyl, alkenyl, alkynyl, aryl, cycloalkyl, heterocyclyl, and heteroaryl,
  provided that when $R^1$ is hydrogen, $R^S$ is selected from the group consisting of
    alkyl;
    alkyl substituted with one or more $R^{ak}$;
    alkenyl;
    alkynyl;
    aryl;
    aryl substituted with one or more $R^a$;
    azido;
    cyano;
    cycloalkyl;
    cycloalkyl substituted with one or more $R^c$;
    fused cycloalkylaryl substituted with one or more $R^{f1}$;
    fused arylcycloalkyl substituted with one or more $R^{f2}$;
    fused heterocyclyaryl substituted with one or more $R^{f3}$;
    fused arylheterocyclyl substituted with one or more $R^{f4}$;
    fused cycloalkylheteroaryl substituted with one or more $R^{f5}$;
    fused heteroarylcycloalkyl substituted with one or more $R^{f6}$;
    fused heterocyclylheteroaryl substituted with one or more $R^{f7}$;
    fused heteroarylheterocyclyl substituted with one or more $R^{f8}$;
    heterocyclyl;
    heterocyclyl substituted with one or more $R^{hc}$;
    heteroaryl;
    heteroaryl substituted with one or more $R^{ha}$;
    —$NR^3R^4$;
    —$C(O)NR^3R^4$;
    —$C(O)R^5$;
    —$C(O)_2R^6$;
    —$S(O)_jR^7$;
    —$OR^8$; and
    nitro.

In one embodiment, U is N.
In another embodiment, $A^1$ is O.
In another embodiment, $A^2$ is O.
In another embodiment, both $A^1$ and $A^2$ are O.
In another embodiment x is zero.
In another embodiment y is zero.
In another embodiment, V is C—$(CH_2)_v R^V$; W is C—$(CH_2)_w R^W$; X is C—$(CH_2)_x R^X$; Y is C—$(CH_2)_y R^Y$; and Z is C—$(CH_2)_z R^Z$.
In another embodiment, V is C—$(CH_2)_v R^V$, $R^V$ is halogen or —O—$CH_3$ and v is zero.
In another embodiment, X is C—$(CH_2)_x R^X$, $R^X$ is halogen or hydrogen and x is zero.

In another embodiment, at least one of v, w and z is 1. In another embodiment, at least one of $R^W$, $R^X$ and $R^Y$ is halogen. In another embodiment, w is zero and $R^W$ is chloro or fluoro. In another embodiment, x is zero and $R^X$ is chloro or fluoro.

In another embodiment, $R^1$ is —$(CH_2)_qR^Q$, where q is 0 and $R^Q$ is alkyl; aryl; aryl substituted with one or more alkoxy; cycloalkyl; cycloalkyl substituted with one or more alkyl, halogen, or —$C(O)OR^9$, where $R^9$ is hydrogen; alkyl; haloalkyl; heterocyclyl; or heterocyclyl substituted with one or more acyl, —$C(O)OR^9$, or —$S(O)_2R^{10}$, where each $R^9$ and $R^{10}$ independently is alkyl or aryl. In one embodiment, q is 1, $R^Q$ is aryl, aryl substituted with alkoxy, or heterocyclyl. In one embodiment, q is 3, $R^Q$ is heterocyclyl substituted with —$OR^8$ and $R^8$ is alkyl.

In another embodiment, $R^2$ is —$(CH_2)_sR^S$, where s is 0 and $R^S$ is alkyl; aryl; aryl substituted with one or more alkyl, alkoxy, halogen, haloalkyl, or nitro; cycloalkyl; heteroaryl; or heteroaryl substituted with one or more alkyl or haloalkyl. In one embodiment, s is 1 and $R^S$ is aryl, aryl substituted with one or more alkyl, or heteroaryl. In one embodiment, s is 1 or 2 and $R^S$ is —$C(O)OR^6$, where $R^6$ is alkyl. In one embodiment, s is 2 and $R^S$ is aryl.

In another embodiment, U is —C—$OR^8$. In another embodiment, $R^8$ is alkyl. In yet another embodiment, $R^8$ is methyl. In one embodiment, $R^U$ is H, alkyl, or haloalkoxy.

In another embodiment, $R^S$ is aryl. In another embodiment, $R^S$ is a substituted or unsubstituted phenyl group. In still another embodiment, $R^S$ is a chloro-substituted phenyl group.

In another embodiment, $R^S$ is a benzodioxoyl group. In another embodiment, $R^S$ is a benzo[1,3]dioxolyl group. In one embodiment, $R^S$ is a benzodioxinyl group. In another embodiment, $R^S$ is a benzo[1,4]dioxinyl group.

In another embodiment, $R^Q$ is a substituent having the structure of Formula ($R^Q$)

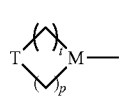

($R^Q$)

wherein M is nitrogen or carbon and T is nitrogen, carbon, oxygen, sulfur or $SO_2$, p is from 1 to 3 and t is from 1 to 3, wherein $R^Q$ may be substituted or unsubstituted as described above. In another embodiment, $R^Q$ is a piperidinyl group, where M is nitrogen, T is —N(H)—, and t and p are both 2.

The present invention also includes a compound of Formula (Ia):

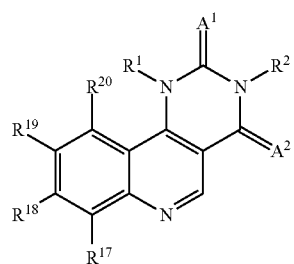

(Ia)

or a salt thereof, wherein
$A^1$ is O or S;
$A^2$ is O or S;
$R^1$ is hydrogen or —$(CH_2)_qR^Q$;
$R^2$ is hydrogen or —$(CH_2)_sR^S$;
$R^{17}$ is hydrogen or —$(CH_2)_vR^V$;
$R^{18}$ is hydrogen or —$(CH_2)_wR^W$;
$R^{19}$ is hydrogen or —$(CH_2)_xR^X$;
$R^{20}$ is hydrogen or —$(CH_2)_yR^Y$;
wherein
each of q, s, v, w, x, and y individually is 0, 1, 2, 3, or 4;
each of $R^Q$, $R^S$, $R^V$, $R^W$, $R^X$, and $R^Y$ is independently selected from the group consisting of
alkyl;
alkyl substituted with one or more $R^{ak}$;
alkenyl;
alkynyl;
aryl;
aryl substituted with one or more $R^a$;
azido;
cyano;
cycloalkyl;
cycloalkyl substituted with one or more $R^c$;
fused cycloalkylaryl;
fused cycloalkylaryl substituted with one or more $R^{f1}$;
fused arylcycloalkyl;
fused arylcycloalkyl substituted with one or more $R^{f2}$;
fused heterocyclylacyl;
fused heterocyclylaryl substituted with one or more $R^{f3}$;
fused arylheterocycyl;
fused arylheterocyclyl substituted with one or more $R^{f4}$;
fused cycloalkylheteroaryl;
fused cycloalkylheteroaryl substituted with one or more $R^{f5}$;
fused heteroarylcycloalkyl;
fused heteroarylcycloalkyl substituted with one or more $R^{f6}$;
fused heterocyclylheteroaryl;
fused heterocyclylheteroaryl substituted with one or more $R^{f7}$;
fused heteroarylheterocyclyl;
fused heteroarylheterocyclyl substituted with one or more $R^{f8}$;
halogen;
haloalkyl;
heterocyclyl;
heterocyclyl substituted with one or more $R^{hc}$;
heteroaryl;
heteroaryl substituted with one or more $R^{ha}$;
—$NR^3R^4$;
—$C(O)NR^3R^4$;
—$C(O)R^5$;
—$C(O)_2R^6$;
—$S(O)_jR^7$;
—$OR^8$; and
nitro;
wherein
each of $R^3$ and $R^4$ is independently selected from the group consisting of H, acyl, alkyl, alkoxy, alkoxyalkyl, alkylsulfonyl, aryl, cycloalkyl, heterocyclyl and heteroaryl;
j is 0, 1, or 2;
each $R^5$, $R^6$, $R^7$, and $R^8$ is independently selected from the group consisting of
hydrogen;
alkyl;
alkyl substituted with one or more $R^{ak}$;
alkenyl;
alkynyl;
alkoxy;
aryl;

aryl substituted with one or more $R^a$;
cycloalkyl;
cycloalkyl substituted with one or more $R^c$;
halogen;
haloalkyl;
heterocyclyl;
heterocyclyl substituted with one or more $R^{hc}$;
heteroaryl;
heteroaryl substituted with one or more $R^{ha}$;
wherein each $R^a$, $R^c$, $R^{f1}$, $R^{f2}$, $R^{f3}$, $R^{f4}$, $R^{f5}$, $R^{f6}$, $R^{f7}$, $R^{hc}$ and $R^{ha}$ is independently selected from the group consisting of acyl, alkyl, alkenyl, alkynyl, alkoxy, amide, amino, aryl, cyano, cycloalkyl, halogen, haloalkyl, haloalkoxy, heteroaryl, hydroxy, nitro, —C(O)OR$^9$, —SO$_2$R$^{10}$, —SR$^{11}$, —C(O)R$^{12}$, —C(O)NR$^{13}$, —NH—SO$_2$—R$^{14}$, —SO$_2$—NR$^{15}$R$^{16}$, and —SO$_2$—CH$_2$—SO$_2$—CH$_3$; and wherein each $R^9$, $R^{10}$, $R^{11}$, $R^{12}$, $R^{13}$, $R^{14}$, $R^{15}$, and $R^{16}$ is independently selected from the group consisting of hydrogen, alkyl, alkenyl, alkynyl, aryl, cycloalkyl, heterocyclyl, and heteroaryl, provided that when $R^1$ is hydrogen, $R^S$ is selected from the group consisting of
alkyl;
alkyl substituted with one or more $R^{ak}$;
alkenyl;
alkynyl;
aryl;
aryl substituted with one or more $R^a$;
azido;
cyano;
cycloalkyl;
cycloalkyl substituted with one or more $R^c$;
fused cycloalkylaryl substituted with one or more $R^{f1}$;
fused arylcycloalkyl substituted with one or more $R^{f2}$;
fused heterocyclyaryl substituted with one or more $R^{f3}$;
fused arylheterocyclyl substituted with one or more $R^{f4}$;
fused cycloalkylheteroaryl substituted with one or more $R^{f5}$;
fused heteroarylcycloalkyl substituted with one or more $R^{f6}$;
fused heterocyclylheteroaryl substituted with one or more $R^{f7}$;
fused heteroarylheterocyclyl substituted with one or more $R^{f8}$;
heterocyclyl;
heterocyclyl substituted with one or more $R^{hc}$;
heteroaryl;
heteroaryl substituted with one or more $R^{ha}$;
—NR$^3$R$^4$;
—C(O)NR$^3$R$^4$;
—C(O)R$^5$;
—C(O)$_2$R$^6$;
—S(O)$_j$R$^7$;
—OR$^8$; and
nitro.

The present invention also includes a compound of Formula (Ib):

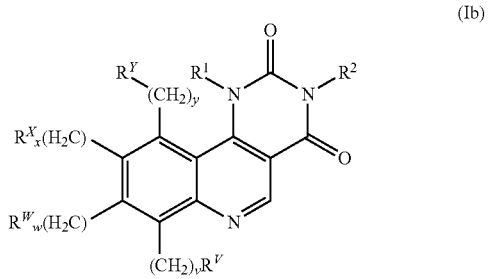

or a salt thereof, wherein $R^1$, $R^2$, $R^V$, $R^W$, $R^X$, $R^Y$, v, w, x and y are as defined with regard to Formula (I).

In one embodiment of Formula (Ib), $R^Y$, $R^X$ and $R^W$ are hydrogen or halogen and y, x and w are each zero.

In another embodiment of Formula (Ib), $R^Y$, $R^X$ and $R^W$ are hydrogen or halogen, y, x and w are each zero, v is zero, and $R^V$ is alkyl, haloalkyl, cycloalkyl, halogen or —OR$^{12}$, where $R^{12}$ is hydrogen, alkyl or haloalkyl.

In another embodiment of Formula (Ib), $R^1$ is hydrogen, alkyl, cycloalkyl, phenyl, benzyl, tetrahydrofuranyl, tetrahydropyranyl, pyrrolidinyl or piperidinyl, wherein, the alkyl, cycloalkyl, piperidinyl, pyrrolidinyl, phenyl and benzyl may be each independently substituted with one or more $R^a$, as described with reference to Formula (I).

In another embodiment of Formula (Ib), $R^2$ is hydrogen alkyl, cycloalkyl, phenyl, benzyl, furanyl, thiophenyl, isoxazolyl, thiophenyl, furanyl, benzodioxolyl, dihydrobenzodioxinyl, indanyl, wherein, the alkyl, cycloalkyl, phenyl, benzyl, thiophenyl and furanyl may be each independently substituted with one or more $R^a$, as described with reference to Formula (I).

In another embodiment of Formula (Ib), $R^Y$, $R^X$ and $R^W$ are hydrogen or halogen, y, x and w are each zero, v is zero, and $R^V$ is alkyl, haloalkyl, halogen or —OR$^{12}$, where $R^{12}$ is hydrogen, alkyl or haloalkyl, and $R^1$ is —(CH$_2$)$_q$—R$^Q$, wherein q is zero and $R^Q$ selected from the group consisting of: hydrogen; $C_3$-$C_6$ cycloalkyl; $C_3$-$C_6$ cycloalkyl substituted with one or more $C_1$-$C_6$ alkyl, halogen, —C(O)OR$^9$ wherein $R^9$ is hydrogen or $C_1$-$C_3$ alkyl, or —NH—SO$_2$—R$^{14}$ wherein $R^{14}$ is $C_1$-$C_3$ alkyl; $C_1$-$C_6$ alkyl; $C_1$-$C_6$ alkyl substituted with one or more halogen, $C_1$-$C_6$ alkoxy, $C_1$-$C_6$ haloalkyl, pyrrolidin-1-yl, or —SO$_2$—R$^{10}$ wherein $R^{10}$ is $C_1$-$C_3$ alkyl; phenyl; phenyl substituted with one or more one or more halogen, $C_1$-$C_6$ alkyl, or $C_1$-$C_6$ alkoxy; —C(O)—R$^5$, wherein $R^5$ is phenyl; —C(O)—R$^5$, wherein $R^5$ is phenyl substituted with one or more halogen, $C_1$-$C_6$ alkyl, or $C_1$-$C_6$ alkoxy; tetrahydro-furan-3-yl; piperidine-4-yl; piperidine-4-yl substituted at the 1 position with —C(O)O—R$^9$ wherein $R^9$ is $C_1$-$C_6$ alkyl, —C(O)—R$^{12}$ wherein $R^{12}$ is $C_1$-$C_6$ alkyl or phenyl, —SO$_2$—R$^{10}$ wherein $R^{10}$ is $C_1$-$C_6$ alkyl, phenyl, 1,1-dioxo-tetrahydro-1-lambda-6-thiophene or —CH$_2$—SO$_2$—CH$_3$, —SO$_2$—NR$^{15}$R$^{16}$ wherein $R^{15}$ and $R^{16}$ are independently selected from the group consisting of hydrogen and $C_1$-$C_6$ alkyl, or —C(O)NR$^{13}$ wherein $R^{13}$ is $C_1$-$C_6$ alkyl; pyrrolidine-3-yl; and pyrrolidine-3-yl substituted at the 1 position with —C(O)O—R$^9$ wherein $R^9$ is $C_1$-$C_6$ alkyl, or —SO$_2$—R$^{10}$ wherein $R^{10}$ is $C_1$-$C_6$ alkyl or phenyl; or $R^1$ is —(CH$_2$)$_q$—R$^Q$, wherein q is 1 and $R^Q$ selected from the group consisting of: phenyl; phenyl substituted with one or more halogen, $C_1$-$C_6$ alkyl, or $C_1$-$C_6$ alkoxy; tetrahydro-furan-2-yl; piperidine-4-yl; piperidine-4-yl substituted at the 1 position with —SO$_2$—R$^{10}$ wherein $R^{10}$ is $C_1$-$C_6$ alkyl; and tetrahydro-pyran-4-yl; and $R^2$ is —$(CH_2)_s$—$R^S$, wherein s is zero and $R^S$ selected from the group consisting of: hydrogen; $C_3$-$C_6$ cycloalkyl; $C_1$-$C_6$ alkyl; $C_1$-$C_6$ alkyl substituted with phenyl or —C(O)$OR^9$ wherein $R^9$ is $C_1$-$C_3$ alkyl; phenyl; phenyl substituted with one or more halogen, $C_1$-$C_6$ alkyl, $C_1$-$C_6$ haloalkyl, $C_1$-$C_6$ alkoxy; $C_1$-$C_6$ haloalkoxy, nitrile, —S—$R^{11}$ wherein $R^{11}$ is $C_1$-$C_6$ alkyl, or —$SO_2$—$R^{10}$ wherein $R^{10}$ is $C_1$-$C_6$ alkyl; furan-3-yl; furan-3-yl substituted with one or more $C_1$-$C_6$ alkyl, or $C_1$-$C_6$ haloalkyl; thiophen-2-yl; thiophen-2-yl substituted with one or more $C_1$-$C_6$ alkyl; thiophen-3-yl; 3,5-dimethyl-isoxazol-4-yl; 3-benzo[1,3]dioxol-5-yl; 3-indan-5-yl; and 2,3-dihydro-benzo[1,4]dioxin-6-yl; or $R^2$ is —$(CH_2)_s$—$R^S$, wherein s is 1 and $R^S$ selected from the group consisting of phenyl; phenyl substituted with one or more halogen, $C_1$-$C_6$ alkyl, $C_1$-$C_6$ alkoxy, or $C_1$-$C_6$ haloalkoxy; —C(O)$OR^9$, wherein $R^9$ is $C_1$-$C_3$ alkyl; and furan-2-yl. In a further embodiment, at least one of $R^1$ or $R^2$ is not hydrogen. In a further embodiment, neither $R^1$ not $R^2$ is hydrogen.

In another embodiment of Formula (Ib), $R^Y$, $R^X$ and $R^W$ are hydrogen or halogen, y, x and w are each zero, v is zero, and $R^V$ is alkyl, haloalkyl, halogen or —$OR^{12}$, where $R^{12}$ is hydrogen, alkyl or haloalkyl, and $R^1$ is —$(CH_2)_q$—$R^Q$, wherein q is zero and $R^Q$ selected from the group consisting of: cyclohexyl; cyclohexyl substituted with one or more $C_1$-$C_6$ alkyl, halogen, —C(O)$OR^9$ wherein $R^9$ is hydrogen or $C_1$-$C_3$ alkyl, or —NH—$SO_2$—$R^{14}$ wherein $R^{14}$ is $C_1$-$C_3$ alkyl; $C_1$-$C_6$ alkyl; $C_1$-$C_6$ alkyl substituted with one or more halogen, —$SO_2$—$R^{16}$ wherein $R^{10}$ is $C_1$-$C_3$ alkyl; phenyl; phenyl substituted with one or more one or more halogen, $C_1$-$C_6$ alkyl, or $C_1$-$C_6$ alkoxy; —C(O)—$R^5$, wherein $R^5$ is phenyl; —C(O)—$R^5$, wherein $R^5$ is phenyl substituted with one or more halogen, $C_1$-$C_6$ alkyl, or $C_1$-$C_6$ alkoxy; piperidine-4-yl; piperidine-4-yl substituted at the 1 position with —C(O)O—$R^9$ wherein $R^9$ is $C_1$-$C_6$ alkyl, —C(O)—$R^{12}$ wherein $R^{12}$ is $C_1$-$C_6$ alkyl, —$SO_2$—$R^{16}$ wherein $R^{10}$ is $C_1$-$C_6$ alkyl or phenyl, —$SO_2$—$NR^{15}R^{16}$ wherein $R^{15}$ and $R^{16}$ are independently selected from the group consisting of hydrogen and $C_1$-$C_6$ alkyl, or —C(O)$NR^{13}$ wherein $R^{13}$ is $C_1$-$C_6$ alkyl; or $R^1$ is —$(CH_2)_q$—$R^Q$, wherein q is 1 and $R^Q$ selected from the group consisting of: phenyl; phenyl substituted with one or more halogen, $C_1$-$C_6$ alkyl, or $C_1$-$C_6$ alkoxy; piperidine-4-yl; piperidine-4-yl substituted at the 1 position with —$SO_2$—$R^{10}$ wherein $R^{10}$ is $C_1$-$C_6$ alkyl; and $R^2$ is —$(CH_2)_s$—$R^S$, wherein s is zero and $R^S$ selected from the group consisting of: $C_3$-$C_6$ cycloalkyl; $C_1$-$C_6$ alkyl; phenyl; phenyl substituted with one or more halogen, $C_1$-$C_6$ alkyl, $C_1$-$C_6$ alkoxy; $C_1$-$C_6$ haloalkoxy, nitrile, —S—$R^{11}$ wherein $R^{11}$ is $C_1$-$C_6$ alkyl, or —$SO_2$—$R^{10}$ wherein $R^{10}$ is $C_1$-$C_6$ alkyl; or $R^2$ is —$(CH_2)_s$—$R^S$, wherein s is 1 and $R^S$ selected from the group consisting of phenyl; and phenyl substituted with one or more halogen, $C_1$-$C_6$ alkyl, $C_1$-$C_6$ alkoxy; or $C_1$-$C_6$ haloalkoxy.

In another embodiment of Formula (Ib), $R^Y$, $R^X$ and $R^W$ are hydrogen or halogen, y, x and w are each zero, v is zero, and $R^V$ is alkyl, haloalkyl, halogen or —$OR^{12}$, where $R^{12}$ is hydrogen, alkyl or haloalkyl, and $R^1$ is —$(CH_2)_q$—$R^Q$, wherein q is zero and $R^Q$ selected from the group consisting of: cyclohexyl; cyclohexyl substituted with one or more $C_1$-$C_6$ alkyl, halogen, —C(O)$OR^9$ wherein $R^9$ is hydrogen or $C_1$-$C_3$ alkyl; $C_1$-$C_6$ alkyl; $C_1$-$C_6$ alkyl substituted with one or more halogen; phenyl; phenyl substituted with one or more one or more halogen, $C_1$-$C_6$ alkyl, or $C_1$-$C_6$ alkoxy; and $R^2$ is —$(CH_2)_s$—$R^S$, wherein s is zero and $R^S$ selected from the group consisting of: $C_1$-$C_6$ alkyl; phenyl; phenyl substituted with one or more halogen, $C_1$-$C_6$ alkyl, $C_1$-$C_6$ alkoxy; $C_1$-$C_6$ haloalkoxy; or $R^2$ is —$(CH_2)_s$—$R^S$, wherein s is 1 and $R^S$ selected from the group consisting of phenyl; and phenyl substituted with one or more halogen, $C_1$-$C_6$ alkyl, $C_1$-$C_6$ alkoxy; or $C_1$-$C_6$ haloalkoxy.

The present invention also includes a compound of Formula (Ic):

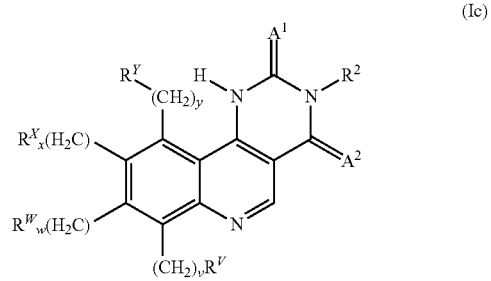

(Ic)

or a salt thereof, wherein $A^1$, $A^2$, $R^2$, $R^V$, $R^W$, $R^X$, $R^Y$, v, w, x and y are as defined with regard to Formula (I).

The present invention also includes a compound of Formula (Id):

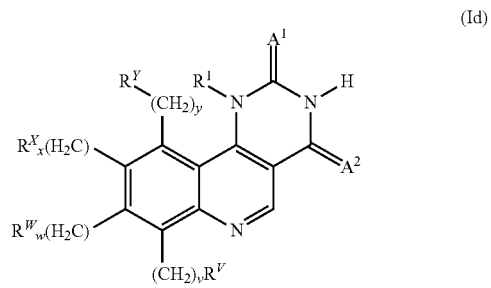

(Id)

or a salt thereof, wherein $A^1$, $A^2$, $R^1$, $R^V$, $R^W$, $R^X$, $R^Y$, v, w, x and y are as defined with regard to Formula (I).

Another embodiment of the present invention includes a compound as hereinbefore described with reference to any one of the below-identified Examples, or a salt thereof.

Another embodiment of the present invention includes a pharmaceutical composition comprising a compound of the present invention. Another embodiment of the present invention includes a pharmaceutical composition further including one or more pharmaceutically acceptable carriers. Another embodiment of the present invention includes a pharmaceutical composition further comprising one or more additional therapeutic agent, yet another embodiment includes wherein the one or more additional therapeutic agent is selected from steroids, cyclooxygenase inhibitors, non-steroidal-anti-inflammatory drugs, or TNF-α antibodies, such as for example acetyl salicylic acid, bufexamac, diclofenac potassium, sulindac, diclofenac sodium, ketorolac trometamol, tolmetine, ibuprofen, naproxen, naproxen sodium, tiaprofen acid, flurbiprofen, mefenamic acid, nifluminic acid, meclofenamate, indomethacin, proglumetacine, ketoprofen, nabumetone, paracetamol, piroxicam, tenoxicam, nimesulide, fenylbutazon, tramadol, beclomethasone dipropionate, betamethasone, beclomethasone, budesonide, fluticasone, mometasone, dexamethasone, hydrocortisone, methylprednisolone, prednisolone, prednisone, triamcinolone, celecoxib, rofecoxib, infliximab, leflunomide, etanercept, CPH 82, methotrexate, sulfasalazine, antilymphocytory immunoglobulines, antithymocytory immunoglobulines, azathioprine, cyclosporine, tacrolimus substances, ascormycin, rapamycin, or muromonab-CD3.

Another embodiment of the present invention includes a compound of the present invention for use as an active therapeutic substance.

Another embodiment of the present invention includes a compound of the present invention for use to inhibit the activity of TNF-α in a subject in need thereof.

Another embodiment of the present invention includes a compound of the present invention for use to inhibit PDE4 in a subject in need thereof.

Another embodiment of the present invention includes a compound of the present invention for use in the treatment or prevention of conditions or disorders mediated by activity of TNF-α.

Another embodiment of the present invention includes a compound of the present invention for use in the treatment or prevention of conditions or disorders mediated by PDE4.

Another embodiment of the present invention includes a use of a compound of the present invention in the manufacture of a medicament for use of inhibiting the activity of TNF-α in a subject in need thereof.

Another embodiment of the present invention includes a use of a compound of the present invention in the manufacture of a medicament for use of inhibiting PDE4 in a subject in need thereof.

Another embodiment of the present invention includes a use of a compound of the present invention in the manufacture of a medicament for use in the treatment or prevention of conditions or disorders mediated by activity of TNF-α.

Another embodiment of the present invention includes a use of a compound of the present invention in the manufacture of a medicament for use in the treatment or prevention of conditions or disorders mediated by PDE4.

Another embodiment of the present invention includes a method of inhibiting the activity of TNF-α in a subject in need thereof through the administration of a compound of the present invention.

Another embodiment of the present invention includes a method of inhibiting PDE4 in a subject in need thereof through the administration of a compound of the present invention.

Another embodiment of the present invention includes a method for the treatment or prevention of conditions or disorders mediated by activity of TNF-α through the administration of a compound of the present invention.

Another embodiment of the present invention includes a method for the treatment or prevention of conditions or disorders mediated by PDE4 through the administration of a compound of the present invention.

Another embodiment of the present invention includes a method for the treatment of an inflammatory disease through the administration of a compound of the present invention. Inflammatory diseases may include, as non-limiting examples, viral, alcoholic, or drug-induced acute and fulminant hepatitis, hepatic steatosis, both alcoholic and non-alcoholic, viral and non-viral hepatitis, hepatic cirrhosis, autoimmune hepatitis, chronic active hepatitis, Wilson's disease, myasthenia gravis, idiopathic sprue, autoimmune inflammatory bowel disease, ulcerative colitis, Crohn's disease, inflammatory bowel diseases, endocrine ophthalmopathy, Grave's disease, sarcoidosis, primary biliary cirrhosis, pancreatitis, nephritis, endotoxin shock, septic shock, haemodynamic shock, sepsis syndrome, post ischemic reperfusion injury, malaria, mycobacterial infection, meningitis, psoriasis, asthma, chronic obstructive pulmonary disease (COPD), eosinophilia, congestive heart failure, fibrotic diseases, cystic fibrosis, pulmonary fibrosis, hepatic fibrosis, renal fibrosis, cachexia, graft rejection, graft vs. host disease, rejection by transplantation, cancer, diseases involving angiogenesis, autoimmune diseases, ankylosing spondylitis, autoimmune encephalomyelitis, autoimmune hematological disorders, hemolytic anemia, aplastic anemia, pure red cell anemia, idiopathic thrombocytopenia, systemic lupus erythematosus (SLE), polychondritis, scleroderma, Wegener granulomatosis, dermatomyositis, Reiter's syndrome, non infection uveitis, autoimmune keratitis, keratoconjunctivitis sicca, vernal keratoconjunctivitis, interstitial lung fibrosis, psoriatic arthritis, psoriasis and other benign or malignant proliferative skin diseases, atopic dermatitis, urticaria, neurodegenerative disorders, Parkinson's disease, Alzheimer's disease, acute and chronic multiple sclerosis, cancer, viral infection, human immunodeficiency virus (HIV), cachexia, thrombosis, skin inflammatory diseases, osteoarthritis (OA), osteoporosis, RA, emphysema, chronic bronchiolitis, allergic rhinitis, radiation damage, hyperoxic alveolar injury, periodontal disease, non-insulin dependent diabetes mellitus (Type II diabetes), and insulin dependent diabetes mellitus (Juvenile or Type I diabetes).

In another embodiment, such treatment or prevention relates to conditions mediated by the inhibition of PDE 4. Such conditions include a variety of conditions, especially inflammatory and/or allergic diseases, in mammals such as humans, for example: asthma, chronic obstructive pulmonary disease (COPD) (e.g. chronic bronchitis and/or emphysema), atopic dermatitis, urticaria, allergic rhinitis, allergic conjunctivitis, vernal conjunctivitis, eosinophilic granuloma, psoriasis, rheumatoid arthritis, septic shock, ulcerative colitis, Crohn's disease, reperfusion injury of the myocardium and brain, chronic glomerulonephritis, endotoxic shock, adult respiratory distress syndrome, multiple sclerosis, cognitive impairment (e.g. in a neurological disorder such as Alzheimer's disease), depression, or pain. Ulcerative colitis and/or Crohn's disease are collectively often referred to as inflammatory bowel disease.

In on embodiment of the present invention, the inflammatory and/or allergic disease is chronic obstructive pulmonary disease (COPD), asthma, rheumatoid arthritis or allergic rhinitis in a mammal (e.g. human).

The scope of the present invention includes combinations of embodiments.

Unless otherwise stated, structures depicted herein are also meant to include compounds which differ only in the presence of one or more isotopically enriched atoms. For example, compounds having the present structure except for the replacement of a hydrogen atom by a deuterium or tritium, or the replacement of a carbon atom by a $^{13}$C- or $^{14}$C-enriched carbon are within the scope of the invention.

Certain of the compounds described herein contain one or more chiral centers, or may otherwise be capable of existing as multiple stereoisomers. The scope of the present invention includes mixtures of stereoisomers as well as purified enantiomers or enantiomerically/diastereomerically enriched mixtures. Also included within the scope of the invention are the individual isomers of the compounds represented by the formulae of the present invention, as well as any wholly or partially equilibrated mixtures thereof. The present invention also includes the individual isomers of the compounds represented by the formulas above as mixtures with isomers thereof in which one or more chiral centers are inverted.

The present invention includes salts of the compounds herein described.

The term "salt" or "pharmaceutically acceptable salt" refers to salts that retain the biological effectiveness and properties of the compounds of Formula I, and which are not biologically or otherwise undesirable. Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl)amines, tri(substituted alkyl)amines, alkenyl amines, dialkenyl amines, trialkenyl amines, substituted alkenyl amines, di(substituted alkenyl)amines, tri(substituted alkenyl)amines, cycloalkyl amines, di(cycloalkyl)amines, tri(cycloalkyl)amines, substituted cycloalkyl amines, disubstituted cycloalkyl amine, trisubstituted cycloalkyl amines, cycloalkenyl amines, di(cycloalkenyl)amines, tri(cycloalkenyl)amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Specific examples of suitable amines include, by way of example only, isopropylamine, trimethyl amine, diethyl amine, tri(iso-propyl)amine, tri(n-propyl)amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Salts of the compounds of the present invention may further comprise acid addition salts. Representative salts include acetate, benzenesulfonate, benzoate, bicarbonate, bisulfate, bitartrate, borate, calcium edetate, camsylate, carbonate, clavulanate, citrate, dihydrochloride, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, sulfate, tannate, tartrate, teoclate, tosylate, triethiodide, trimethylammonium, and valerate salts.

As used herein, the phrase "effective amount" means that amount of a drug or pharmaceutical agent that will elicit the biological or medical response of a tissue, system, animal, or human that is being sought, for instance, by a researcher or clinician. The phrase "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function. For use in therapy, therapeutically effective amounts of a compound of formulae of the present, as well as salts thereof, may be administered as the raw chemical. Additionally, the active ingredient may be presented as a pharmaceutical composition.

A therapeutically effective amount of a compound of the present invention will depend upon a number of factors. For example, the species, age and weight of the recipient, the precise condition requiring treatment and its severity, the nature of the formulation and the route of administration are all factors to be considered. The therapeutically effective amount ultimately should be at the discretion of the attendant or veterinarian. Regardless, an effective amount of a compound of the present invention for the treatment of humans, generally, should be in the range of 0.01 to 100 mg/kg body weight of recipient (mammal) per day. More usually the effective amount should be in the range of 1 to 10 mg/kg body weight per day. Thus, for a 70 kg adult mammal the actual amount per day would usually be from 70 to 700 mg. This amount may be given in a single dose per day or in a number (such as two, three, four, five, or more) of sub-doses per day such that the total daily dose is the same. An effective amount of a salt may be determined as a proportion of the effective amount of the compound of the formulae of the present invention per se. Similar dosages should be appropriate for treatment of the other conditions referred to herein.

The compounds of the present invention demonstrate utility as inhibitors of TNF-α activity. In an embodiment, the invention provides a method for inhibiting TNF-α activity comprising contacting a cell in which inhibition of TNF-α is desired with a TNF-α inhibitor of the present invention. In an embodiment, the TNF-α inhibitor interacts with and reduces the activity of TNF-α in a cell.

As used herein, reference is made to one or more disorder, condition, or disease mediated by TNF-α or amplified by TNF-α and such shall include diseases associated with or implicating TNF-α activity, for example, the overactivity of TNF-α, and conditions that accompany with these diseases with reference to: 1) TNF-α expression in cells which normally do not express TNF-α; 2) TNF-α activity by cells which normally do not possess active TNF-α; 3) increased TNF-α expression leading to unwanted cell proliferation; or 4) mutations leading to constitutive activation of TNF-α.

The present invention further provides pharmaceutical compositions that include effective amounts of compounds of the formulae of the present invention and salts thereof, and one or more pharmaceutically acceptable carriers, diluents, or excipients. The compounds of the formulae of the present invention, including salts thereof, are as herein described. The carrier(s), diluent(s), or excipient(s) must be acceptable, in the sense of being compatible with the other ingredients of the formulation and not deleterious to the recipient of the pharmaceutical composition.

In accordance with another aspect of the invention there is also provided a process for the preparation of a pharmaceutical formulation including admixing a compound of the formulae of the present invention, including a salt thereof, with one or more pharmaceutically acceptable carriers, diluents or excipients.

Pharmaceutical formulations may be presented in unit dose forms containing a predetermined amount of active ingredient per unit dose. Such a unit may contain, as a non-limiting example, 0.5 mg to 1 g of a compound of the present invention, depending on the condition being treated, the route of administration, and the age, weight, and condition of the patient. Typical unit dosage formulations are those containing a daily dose or sub-dose, as herein above recited, or an appropriate fraction thereof, of an active ingredient. Such pharmaceutical formulations may be prepared by any of the methods well known in the pharmacy art.

Pharmaceutical formulations may be adapted for administration by any appropriate route, for example by an oral (including buccal or sublingual), rectal, nasal, topical (including buccal, sublingual or transdermal), vaginal, or parenteral (including subcutaneous, intramuscular, intravenous or intradermal) route. Such formulations may be prepared by any method known in the art of pharmacy, for example by bringing into association the active ingredient with the carrier(s) or excipient(s). By way of example, and not meant to limit the invention, with regard to certain conditions and disorders for which the compounds of the present invention are believed useful, certain routes will be preferable to others.

Pharmaceutical formulations adapted for oral administration may be presented as discrete units such as capsules or tablets; powders or granules; solutions or suspensions, each with aqueous or non-aqueous liquids; edible foams or whips; or oil-in-water liquid emulsions or water-in-oil liquid emulsions. For instance, for oral administration in the form of a tablet or capsule, the active drug component can be combined with an oral, non-toxic pharmaceutically acceptable inert carrier such as ethanol, glycerol, water, and the like. Generally, powders are prepared by comminuting the compound to a suitable fine size and mixing with an appropriate pharmaceutical carrier such as an edible carbohydrate, as, for example, starch or mannitol. Flavorings, preservatives, dispersing agents, and coloring agents can also be present.

Capsules are made by preparing a powder, liquid, or suspension mixture and encapsulating with gelatin or some other appropriate shell material. Glidants and lubricants such as colloidal silica, talc, magnesium stearate, calcium stearate, or solid polyethylene glycol can be added to the mixture before the encapsulation. A disintegrating or solubilizing agent such as agar-agar, calcium carbonate or sodium carbonate can also be added to improve the availability of the medicament when the capsule is ingested. Moreover, when desired or necessary, suitable binders, lubricants, disintegrating agents, and coloring agents can also be incorporated into the mixture. Examples of suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants useful in these dosage forms include, for example, sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

Tablets are formulated, for example, by preparing a powder mixture, granulating or slugging, adding a lubricant and disintegrant, and pressing into tablets. A powder mixture may be prepared by mixing the compound, suitably comminuted, with a diluent or base as described above. Optional ingredients include binders such as carboxymethylcellulose, alginates, gelatins, or polyvinyl pyrrolidone, solution retardants such as paraffin, resorption accelerators such as a quaternary salt, and/or absorption agents such as bentonite, kaolin, or dicalcium phosphate. The powder mixture can be wet-granulated with a binder such as syrup, starch paste, acadia mucilage or solutions of cellulosic or polymeric materials, and forcing through a screen. As an alternative to granulating, the powder mixture can be run through the tablet machine and the result is imperfectly formed slugs broken into granules. The granules can be lubricated to prevent sticking to the tablet-forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Where appropriate, dosage unit formulations for oral administration can be microencapsulated. The formulation can also be prepared to prolong or sustain the release as for example by coating or embedding particulate material in polymers, wax or the like.

Oral fluids such as solutions, syrups, and elixirs can be prepared in dosage unit form so that a given quantity contains a predetermined amount of the compound. Syrups can be prepared, for example, by dissolving the compound in a suitably flavored aqueous solution, while elixirs are prepared through the use of a non-toxic alcoholic vehicle. Suspensions can be formulated generally by dispersing the compound in a nontoxic vehicle. Solubilizers and emulsifiers such as ethoxylated isostearyl alcohols and polyoxy ethylene sorbitol ethers, preservatives; flavor additives such as peppermint oil, or natural sweeteners, saccharin, or other artificial sweeteners; and the like can also be added.

Suitable packaging for the pharmaceutical solution formulations may be all approved containers intended for parenteral use, such as plastic and glass containers, ready-to-use syringes and the like. In an embodiment, the container is a sealed glass container, such as a vial or an ampoule. A hermetically sealed glass vial is one example of a sealed glass container. According to an embodiment of the present invention, there is provided, in a sealed glass container, a sterile, injectable solution comprising a compound of the present invention in a physiologically acceptable solvent, and which has an appropriate pH for stability. Acid salts of the compounds of the present invention may be more soluble in aqueous solutions than their free base counter parts, but when the acid salts are added to aqueous solutions the pH of the solution may be too low to be suitable for administration. Thus, solution formulations having a pH above pH 4.5 may be combined prior to administration with a diluent solution of pH greater than 7 such that the pH of the combination formulation administered is pH 4.5 or higher. In one embodiment, the diluent solution comprises a pharmaceutically acceptable base such as sodium hydroxide and the pH of the combined formulation administered is between pH 5.0 and 7.0. One or more additional components such as co-solubilizing agents, tonicity adjustment agents, stabilizing agents and preservatives, for instance of the kind previously specified, may be added to the solution prior to passing the solution through the sterilizing filter.

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations may be applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouthwashes.

Pharmaceutical formulations adapted for nasal administration, where the carrier is a solid, include a coarse powder having a particle size for example in the range 20 to 500 microns. The powder is administered in the manner in which snuff is taken, i.e., by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists, which may be generated by means of various types of metered dose pressurized aerosols, nebulizers, or insufflators.

Further, the compositions of the present invention may also be in the form of suppositories for rectal administration of the compounds of the invention. These compositions can be prepared by mixing the drug with a suitable non-irritating excipient which is solid at ordinary temperatures but liquid at the rectal temperature and will thus melt in the rectum to release the drug. Such materials include cocoa butter and polyethylene glycols, for example. Pharmaceutical formulations adapted for rectal administration may be presented as suppositories or as enemas.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and solutes that render the formulation isotonic with the blood of the intended recipient; and aqueous and non-aqueous sterile suspensions which may include suspending agents and thickening agents. The formulations may be presented in unit-dose or multi-dose containers, for example sealed ampules and vials, and may be stored in a freeze-dried (lyophilized) condition requiring only the addition of the sterile liquid carrier, for example water for injections, immediately prior to use.

Extemporaneous injection solutions and suspensions may be prepared from sterile powders, granules, and tablets.

In addition to the ingredients particularly mentioned above, the formulations may include other agents conventional in the art having regard to the type of formulation in question. For example, formulations suitable for oral administration may include flavoring or coloring agents.

In a further embodiment to this aspect and described hereinbelow in further detail, the invention encompasses a combination therapy for treating or preventing a disorder mediated by TNF-α in a subject. The combination therapy comprises administering to the subject a therapeutically or prophylactically effective amount of a compound of the present invention and one or more other therapy including chemotherapy, radiation therapy, gene therapy, and immunotherapy.

In an embodiment of the present invention, the compound of the present invention may be administered in combination with other therapeutic compounds. In particular, a compound of this invention can be advantageously used in combination with i) Leukotriene receptor antagonists, ii) Leukotriene biosynthesis inhibitors, iii) COX-2 selective inhibitors, iv) statins, v) NSAIDs, vi) M2/M3 antagonists, vii) corticosteroids, viii) Hi (histamine) receptor antagonists, ix) beta 2 adrenoceptor agonists, x) interferons, xi) antiviral drugs such as protease inhibitors, helicase inhibitors, polymerase inhibitors, lamivudine, and the like, xiii) ursodeoxycholic acid, xiv) glycyrrhizin, xv) human growth factor (HGF), or xvi) aminosalicylic acids such as salazosulfapyridine, mesalazin, or the like.

The compounds of the present invention may also be used in combination with other conventional anti-inflammatory or immunosuppressive agents, such as steroids, cyclooxygenase inhibitors, non-steroidal-anti-inflammatory drugs, TNF-α antibodies or other TNF-binding proteins, such as for example acetyl salicylic acid, bufexamac, diclofenac potassium, sulindac, diclofenac sodium, ketorolac trometamol, tolmetine, ibuprofen, naproxen, naproxen sodium, tiaprofen acid, flurbiprofen, mefenamic acid, nifluminic acid, meclofenamate, indomethacin, proglumetacine, ketoprofen, nabumetone, paracetamol, piroxicam, tenoxicam, nimesulide, fenylbutazon, tramadol, beclomethasone dipropionate, betamethasone, beclamethasone, budesonide, fluticasone, mometasone, dexamethasone, hydrocortisone, methylprednisolone, prednisolone, prednisone, triamcinolone, celecoxib, rofecoxib, infliximab, leflunomide, etanercept, CPH 82, methotrexate, sulfasalazine, antilymphocyte immunoglobulins, antithymocyte immunoglobulins, azathioprine, cyclosporine, tacrolimus substances, ascormycin, rapamycin, adalimumab, muromonab-CD3 or other antibodies or fusion proteins that modulate T-cell function such as abatacept, alefacept and efalizumab. Additionally, yet to emerge agents are contemplated as being useful in combination with the compound of the present invention.

As noted above, the compounds of the present invention may be employed alone or in combination with other therapeutic agents, including other compounds of the present invention. Such a combination of pharmaceutically active agents may be administered together or separately and, when administered separately, administration may occur simultaneously or sequentially, in any order. The amounts of the compounds or agents and the relative timings of administration will be selected in order to achieve the desired therapeutic effect. The administration in combination of a compound of the formulae of the present invention including salts thereof with other treatment agents may be in combination by administration concomitantly in: (1) a unitary pharmaceutical composition including both compounds; or (2) separate pharmaceutical compositions each including one of the compounds. Alternatively, the combination may be administered separately in a sequential manner wherein one treatment agent is administered first and the other second or vice versa. Such sequential administration may be close in time or remote in time. The compounds of the present invention may be used in the treatment of a variety of disorders and conditions and, as such, the compounds of the present invention may be used in combination with a variety of other suitable therapeutic agents useful in the treatment or prophylaxis of those disorders or conditions.

The compounds of this invention may be made by a variety of methods, including well-known standard synthetic methods. An illustrative general synthetic method is set out in the following reaction Scheme (in which variables are as defined before or are defined) using readily available starting materials, and reagents. In these reactions, it is also possible to make use of variants which are themselves known to those of ordinary skill in this art, but are not mentioned in greater detail. Specific compounds of the invention are prepared in the working Examples.

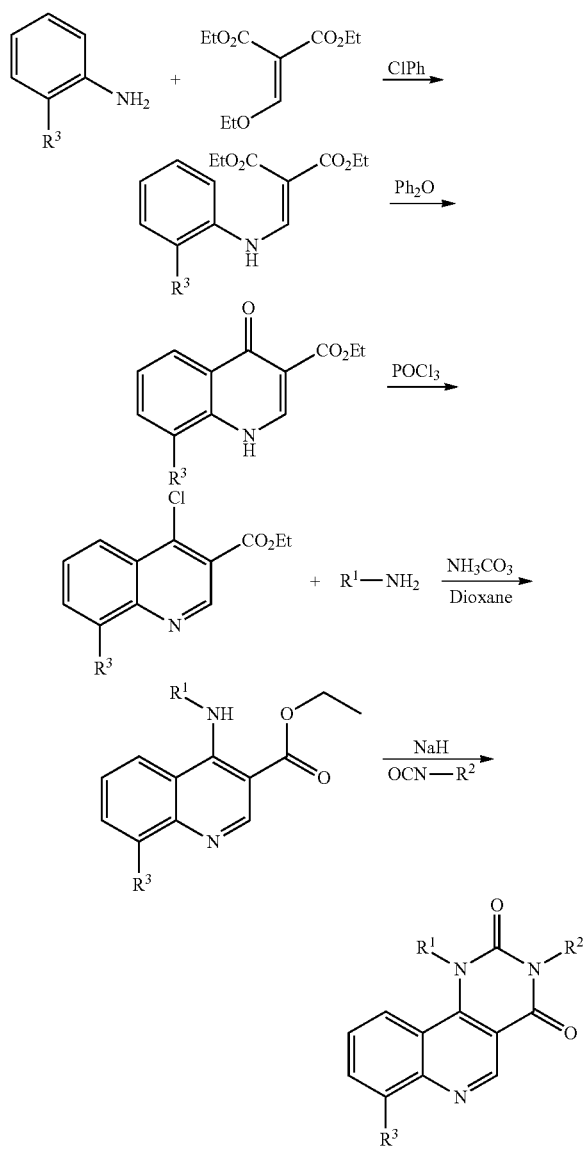

In all of the examples described below, protecting groups for sensitive or reactive groups are employed where necessary in accordance with general principles of synthetic chemistry. Protecting groups may be manipulated according to standard methods of organic synthesis. These groups may be removed at a convenient stage of the compound synthesis using methods that are readily apparent to those skilled in the art. The selection of processes as well as the reaction conditions and order of their execution shall be consistent with the preparation of compounds of the present invention.

Those skilled in the art will recognize if a stereocenter exists. As noted hereinabove, the present invention includes all possible stereoisomers and includes not only racemic compounds but the individual enantiomers as well. When a compound is desired as a single enantiomer, such may be obtained by stereospecific synthesis, by resolution of the final product or any convenient intermediate, or by chiral chromatographic methods as are known in the art. Resolution of the final product, an intermediate, or a starting material may be affected by any suitable method known in the art.

The present invention also provides a method for the synthesis of compounds useful as intermediates in the preparation of compounds of the present invention along with methods for their preparation.

The compounds can be prepared according to the following General procedures. In these reactions, variants may be employed which are themselves known to those of ordinary skill in this art, but are not mentioned in greater detail. As will be apparent to those skilled in the art, the format and designation of variable substituent groups in the following procedures may be different from that used in the Formulae of the present invention.

Description of General Synthetic Methods

General Procedure A: Preparation of 4-chloro-quinoline-3-carboxylic acid ethyl ester Analogues To a substituted aniline (5 mmol) in chlorobenzene (15 mL) is added diethyl ethoxymethylene-malonate (5 mmol) and stirred at 140° C. for 12-16 h. The reaction mass is concentrated to dryness on a rotary evaporator, POCl$_3$ (15 mL) is added and the reaction mass is stirred at 120° C. for 12 h or microwaved at 150° C. for 30 min. After removing most of POCl$_3$ on rotary evaporator, a slurry of ice in sodium bicarbonate solution is slowly added and the resulting reaction product is extracted into ethyl acetate (2×50 mL). The combined ethyl acetate extracts are washed with brine, dried over sodium sulfate, concentrated and purified on column to give the desired quinoline derivative.

The following 4-chloro-quinoline-3-carboxylic acid ethyl ester analogues were prepared using the above procedure:
4,6-Dichloro-8-methoxy-quinoline-3-carboxylic acid ethyl ester;
4,7-Dichloro-8-methoxy-quinoline-3-carboxylic acid ethyl ester;
4-Chloro-6-fluoro-8-methoxy-quinoline-3-carboxylic acid ethyl ester;
4-Chloro-8-ethyl-quinoline-3-carboxylic acid ethyl ester;
4-Chloro-8-propyl-quinoline-3-carboxylic acid ethyl ester;
4-Chloro-8-isopropyl-quinoline-3-carboxylic acid ethyl ester; and
4-Chloro-8-trifluoromethoxy-quinoline-3-carboxylic acid ethyl ester.

General Procedure B: Preparation of 4-alkylamino- or 4-arylamino-quinoline-3-carboxylic acid ethyl ester Analogues To a solution of a 4-chloro-quinoline-3-carboxylic acid ethyl ester analogue (10.0 mmol) in anhydrous THF (50 mL) is added cesium carbonate (20.0 mmol) and an amine (1.2 eq. 12.0 mmol). The reaction mixture is then heated to reflux and stirred at 70° C. for 4 h. After completion of the reaction, the mixture is poured into water (100 mL) and extracted with ethyl acetate (2×50 mL) and the organic extracts are combined, washed with brine solution (2×50 mL), concentrated in vacuo to give the crude product. The concentrated residue is then purified with silica gel chromatography using hexanes-ethyl acetate to afford 4-amino-quinoline-3-carboxylic acid ethyl ester derivative.

General Procedure C: Preparation of Substituted 1H-pyrimido[5,4-c]quinoline-2,4-diones and Substituted 1H-pyrimido[5,4-c]quinoline-thione-ketone Derivatives To a solution of a 4-amino-quinoline-3-carboxylic acid ethyl ester derivative (0.50 mmol) in 10 mL anhydrous DMF is added sodium hydride (4 eq., 2.0 mmol) and stirred at room temperature for 30 min. To this solution an isocyanate or isothiocyanate (1.5-4 eq. 2.0 mmol) is added. The resulting reaction mixture is stirred for 18 h at room temperature or at 100° C. After completion of the reaction, the mixture is poured into water (20 mL) and extracted with ethyl acetate (2×25 mL). The organic extracts are combined, washed with water (2×25 mL), brine (2×25 mL), dried over Na$_2$SO$_4$ and concentrated in vacuo to give the crude product. The residue is then purified by silica gel chromatography using dichloromethane-ethyl acetate to provide desired 1H-pyrimido[5,4-c]quinoline-2,4-dione or thio-ketone derivative.

General Procedure D: Ester Hydrolysis

4-Alkylamino or 4-arylamino-quinoline-3-carboxylic acid ethyl ester (0.50 mmol) is dissolved in THF/MeOH (3 mL, 2:1) and 10 N aq NaOH solution (0.15 mL, 1.5 mmol) is added. After stirring for 1 h at 60° C., the reaction mass is concentrated to dryness, acidified with 4N HCl in dioxane, and concentrated to dryness. To this solid is added 10% methanol in dichloromethane and sodium sulfate. The solution is stirred at room temperature (r.t.), filtered through filter paper and washed with 10% methanol in dichloromethane. The combined filtrates are concentrated to dryness to give acid.

General Procedure E: Preparation of Amides

4-Alkylamino or 4-arylamino-quinoline-3-carboxylic acid analogue (0.5 mmol) and diisopropylethylamine (2.5 mmol) are dissolved in DMF (1 mL) and HBTU (0.6 mmol) is added to the solution. After 15-30 min of stirring, an amine (0.65 mmol) is added and stirred for 30 min. The reaction mixture is diluted with water and the product is extracted into ethyl acetate (2×10 mL). The combined ethyl acetate extracts are washed with brine, dried over sodium sulfate and concentrated to give the amide.

General Procedure F: Preparation of Substituted 1H-pyrimido[5,4-c]quinoline-2,4-diones To an amide (0.5 mmol) in dry THF (or in dry DMF) is added NaH (2.0 mmol) and stirred for 30 min at 60° C. Methyl chloroformate (1.0 mmol) is slowly added and continued stirring at 60° C. for 24 h. The reaction mass is cooled to room temperature, quenched excess NaH with water, diluted with water and extracted into ethyl acetate (2×20 mL). The combined ethyl acetate extracts are washed with brine, dried over sodium sulfate, concentrated and purified on a silica gel column to give desired substituted 1H-pyrimido[5,4-c]quinoline-2,4-dione.

General Procedure G: Removal of tert-butyl carbamate

To a stirred solution of carbamate (1 mmol) in DCM-MeOH (4:1, 1 mL) is added 4 N HCl in dioxane (5 mL). The reaction is stirred at room temperature for 30 min. Solvents are removed under reduced pressure and the residue is dried under vacuum the product.

General Procedure H: Preparation of Amides, Sulfonamides, Sulfamides, Ureas and Carbamates To a stirred solution of amine (1 mmol) in DCM (1 mL) at 0° C. is added triethylamine (3 mmol) followed by addition of an acid chloride or sulfonyl chloride or sulfamyl chloride or chloroformate or isocyanate (1.2 to 1.5 mmol) under $N_2$ atmosphere. The resultant reaction is stirred for 2 h at room temperature. The reaction mixture is diluted with DCM (10 mL), washed with water (2×5 mL), dried over $Na_2SO_4$ and concentrated under reduced pressure. The crude product is purified by silica gel flash column chromatography.

General Procedure I: Acid-Catalyzed Hydrolysis of Esters

To an ester (1 mmol) is added 4N HCl in dioxane (2 mL) and water (0.5 mL) and stirred at 60° C. for 12 h. The reaction mixture is concentrated and azeotroped with toluene three times. The obtained crude is filtered on a small silica gel bed to give the desired acid.

General Procedure J: Oxidation of Sulfides to Sulfones

To solution of a sulfide (0.1 mmol) in dichloromethane (DCM) (5 mL) is added peracetic acid (15 μL, 0.2 mmol, 2.0 eq) at 0° C. and the reaction mixture is slowly warmed up to room temperature while stirring for 30 min. Upon completion of the reaction, the mixture is poured into saturated aqueous sodium bicarbonate (10 mL) solution, extracted with DCM (2×25 mL). The organic extracts are combined and washed with brine (1×25 mL) and concentrated under reduced pressure. The residue is then purified with silica gel chromatography using DCM:EtOAc to give the desired sulfone.

General Procedure K: Cyclization

To the amino-ester (1 mmol) in DMSO (5 mL) was added isocyanate (2 mmol) and the contents were heated at 100° C. for 4 h. Cooled to room temperature and added methanol (10 mL) and concentrated. To the residue was added DBU (1 mmol) and heated for 10 min at 60° C. Cooled the reaction mass to room temperature, diluted with water and extracted into ethyl acetate (2×20 mL). Combined ethyl acetate extracts were washed with brine, dried over sodium sulfate, concentrated and purified on silicagel column to give desired substituted 1H-pyrimido[5,4-c]quinoline-2,4-dione.

EXAMPLES

Example 1

1-cyclopentyl-3-ethyl-7-methoxy-1H-pyrimido[5,4-c]quinoline-2,4-dione

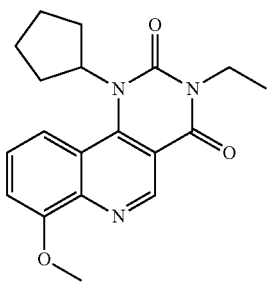 [SMILES: CCn1c(=O)c2cnc3c(OC)cccc3c2n(C2CCCC2)c1=O]

4-Chloro-8-methoxy-quinoline-3-carboxylic acid ethyl ester (2.65 g, 10.0 mmol) was treated with cyclopentylamine (1.06 g, 1.2 eq. 12.0 mmol) following a method similar to general procedure B to afford 4-cyclopentylamino-8-methoxy-quinoline-3-carboxylic acid ethyl ester (2.9 g). The obtained amino-ester (0.5 mmol) was subjected to reaction with ethyl isocyanate (2.0 mmol) according to general procedure C to furnish 1-cyclopentyl-3-ethyl-7-methoxy-1H-pyrimido[5,4-c]quinoline-2,4-dione (83 mg). LCMS: m/z 340 [M+1]$^+$. $^1$H NMR (400 MHz, CDCl$_3$): δ 9.43 (s, 1H), 7.78 (d, 1H), 7.55 (t, 1H), 7.20 (d, 1H), 4.99 (p, 1H), 4.13 (s, 3H), 4.11 (q, 2H), 2.42 (m, 2H), 2.06 (m, 4H), 1.62 (m, 2H) and 1.32 (t, 3H) ppm.

Example 2

1-Cyclopentyl-3-ethyl-7-methoxy-2-thioxo-2,3-dihydro-1H-pyrimido[5,4-c]quinolin-4-one

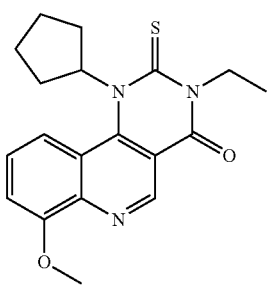 [SMILES: CCn1c(=O)c2cnc3c(OC)cccc3c2n(C2CCCC2)c1=S]

1-Cyclopentyl-3-ethyl-7-methoxy-2-thioxo-2,3-dihydro-1H-pyrimido[5,4-c]quinolin-4-one (12 mg) was prepared from 4-cyclopentylamino-8-methoxy-quinoline-3-carboxylic acid ethyl ester (0.10 mmol) (prepared as described in Example 1) and ethyl isothiocyanate (0.4 mmol) following a procedure similar to general procedure C. LCMS: m/z 356 [M+1]+. 1H NMR (400 MHz, CDCl3): δ 9.50 (s, 1H), 7.74 (d, 1H), 7.53 (t, 1H), 7.21 (d, 1H), 5.03 (p, 1H), 4.09 (s, 3H), 4.07 (q, 2H), 2.42 (m, 2H), 2.08 (m, 4H), 1.64 (m, 2H) and 1.34 (t, 3H).

Example 3

1,3-Dicyclopentyl-7-methoxy-1H-pyrimido[5,4-c]quinoline-2,4-dione

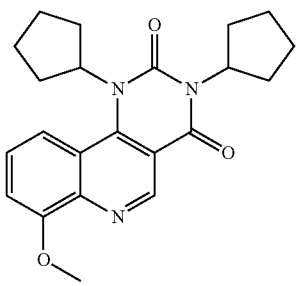 [SMILES: COc1cccc2c1ncc1c(=O)n(C3CCCC3)c(=O)n(C3CCCC3)c12]

1,3-Dicyclopentyl-7-methoxy-1H-pyrimido[5,4-c]quinoline-2,4-dione (17 mg) was prepared from 4-cyclopentylamino-8-methoxy-quinoline-3-carboxylic acid ethyl ester (0.10 mmol) and cyclopentyl isocyanate (0.4 mmol) following general procedure C. LCMS: m/z 380 [M+1]+. 1H NMR (400 MHz, CDCl3): δ 9.51 (s, 1H), 7.82 (d, 1H), 7.62 (t, 1H), 7.28 (d, 1H), 5.34 (m, 1H), 4.98 (m, 1H), 4.15 (s, 3H), 3.95 (m, 4H), 2.38 (m, 2H), 2.12 (m, 2H), 1.93-1.98 (m, 2H), 1.58-169 (m, 4H), and 1.38 (m, 2H) ppm.

Example 4

1-(3,4-Dimethoxy-phenyl)-3-ethyl-7-methoxy-1H-pyrimido[5,4-c]quinoline-2,4-dione

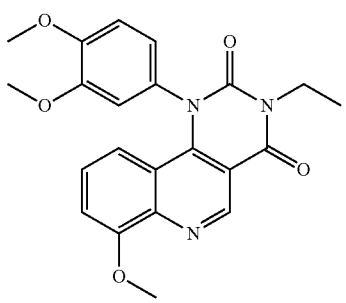 [SMILES: CCn1c(=O)c2cnc3c(OC)cccc3c2n(-c2ccc(OC)c(OC)c2)c1=O]

4-Chloro-8-methoxy-quinoline-3-carboxylic acid ethyl ester (89 mg, 0.3 mmol) was treated with 3,4-dimethoxyaniline following general procedure B to afford 4-(3,4-dimethoxy-phenylamino)-8-methoxy-quinoline-3-carboxylic acid ethyl ester (103 mg). Thus obtained amino-ester (38 mg, 0.1 mmol) was subjected to reaction with ethyl isocyanate (0.5 mmol) according to general procedure C to furnish 1-(3,4-dimethoxy-phenyl)-3-ethyl-7-methoxy-1H-pyrimido [5,4-c]quinoline-2,4-dione (23 mg). LCMS: m/z 408 [M+1]+. 1H NMR (400 MHz, CDCl3): δ 9.64 (s, 1H), 7.11 (m, 2H), 7.00 (s, 1H), 6.91 (m, 2H), 6.60 (s, 1H), 4.20 (q, 2H), 4.09 (s, 3H), 3.99 (s, 3H), 3.86 (s, 3H), and 1.37 (t, 3H) ppm.

Example 5

1-Cyclopentyl-3-isopropyl-7-methoxy-1H-pyrimido[5,4-c]quinoline-2,4-dione

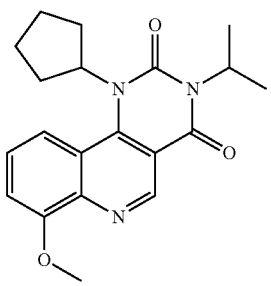 [SMILES: COc1cccc2c1ncc1c(=O)n(C(C)C)c(=O)n(C3CCCC3)c12]

1-Cyclopentyl-3-isopropyl-7-methoxy-1H-pyrimido[5,4-c]quinoline-2,4-dione (19 mg) was prepared from 4-cyclopentylamino-8-methoxy-quinoline-3-carboxylic acid ethyl ester (0.10 mmol) and isopropyl isocyanate (0.4 mmol) following general procedure C. LCMS: m/z 354 [M+1]+. 1H NMR (400 MHz, CDCl3): δ 9.45 (s, 1H), 7.78 (d, 1H), 7.57 (t, 1H), 7.24 (d, 1H), 5.21 (p, 1H), 4.93 (m, 1H), 4.14 (s, 3H), 3.83 (m, 2H), 2.38 (m, 2H), 2.08 (m, 4H), and 1.15 (d, 6H) ppm.

Example 6

1-Cyclopentyl-7-methoxy-3-propyl-1H-pyrimido[5,4-c]quinoline-2,4-dione

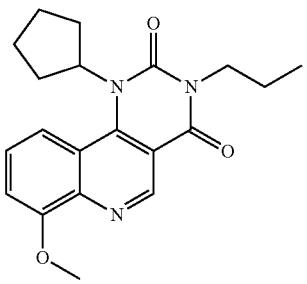 [SMILES: CCCn1c(=O)c2cnc3c(OC)cccc3c2n(C2CCCC2)c1=O]

1-Cyclopentyl-7-methoxy-3-propyl-1H-pyrimido[5,4-c]quinoline-2,4-dione (14 mg) was prepared from 4-cyclopentylamino-8-methoxy-quinoline-3-carboxylic acid ethyl ester (0.10 mmol) and propyl isocyanate (0.4 mmol) following general procedure C. LCMS: m/z 354 [M+1]+. 1H NMR (400 MHz, CDCl3): δ 9.49 (s, 1H), 7.82 (d, 1H), 7.59 (t, 1H), 7.24

(d, 1H), 5.01 (m, 1H), 4.15 (s, 3H), 4.03 (t, 2H), 2.40 (m, 2H), 2.09 (m, 4H), 1.76 (m, 2H), 1.63 (m, 2H), and 1.16 (t, 3H) ppm.

Example 7

3-Butyl-1-cyclopentyl-7-methoxy-1H-pyrimido[5,4-c]quinoline-2,4-dione

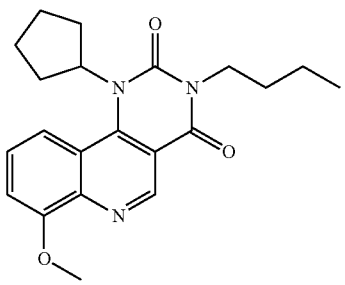 [SMILES: CCCCn1c(=O)c2cnc3c(OC)cccc3c2n(C2CCCC2)c1=O]

3-Butyl-1-cyclopentyl-7-methoxy-1H-pyrimido[5,4-c]quinoline-2,4-dione (26 mg) was prepared from 4-cyclopentylamino-8-methoxy-quinoline-3-carboxylic acid ethyl ester (0.10 mmol) and butyl isocyanate (0.4 mmol) following general procedure C. LCMS: m/z 368 [M+1]+. 1H NMR (400 MHz, CDCl3): δ 9.47 (s, 1H), 7.81 (d, 1H), 7.57 (t, 1H), 7.23 (d, 1H), 4.99 (p, 1H), 4.14 (s, 3H), 4.06 (t, 2H), 2.42 (m, 2H), 2.08 (m, 4H), 1.69 (m, 4H), 1.44 (q, 2H), 0.97 (t, 3H) ppm.

Example 8

1-Cyclopentyl-3-furan-2-ylmethyl-7-methoxy-1H-pyrimido[5,4-c]quinoline-2,4-dione

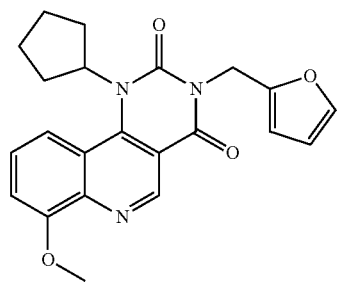 [SMILES: COc1cccc2c1ncc1c(=O)n(Cc3ccco3)c(=O)n(C3CCCC3)c12]

1-Cyclopentyl-3-furan-2-ylmethyl-7-methoxy-1H-pyrimido[5,4-c]quinoline-2,4-dione (21 mg) was prepared from 4-cyclopentylamino-8-methoxy-quinoline-3-carboxylic acid ethyl ester (0.10 mmol) and (2-furyl)methyl isocyanate (0.4 mmol) following general procedure C. LCMS: m/z 392 [M+1]+. 1H NMR (400 MHz, CDCl3): δ 9.45 (s, 1H), 7.78 (d, 1H), 7.57 (t, 1H), 7.32 (d, 1H), 7.24 (d, 1H), 6.30 (d, 1H), 6.18 (d, 1H), 5.04 (p, 1H), 4.33 (s, 2H), 4.12 (s, 3H), 2.40 (m, 2H), 2.11 (m, 4H), and 1.16 (m, 2H) ppm.

Example 9

3-tert-Butyl-1-cyclopentyl-7-methoxy-1H-pyrimido[5,4-c]quinoline-2,4-dione

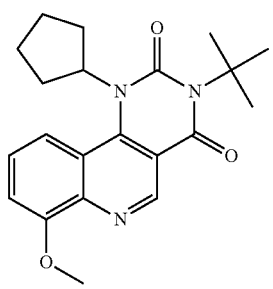 [SMILES: COc1cccc2c1ncc1c(=O)n(C(C)(C)C)c(=O)n(C3CCCC3)c12]

3-tert-Butyl-1-cyclopentyl-7-methoxy-1H-pyrimido[5,4-c]quinoline-2,4-dione (18 mg) was prepared from 4-cyclopentylamino-8-methoxy-quinoline-3-carboxylic acid ethyl ester (0.10 mmol) and tert-butyl isocyanate (0.4 mmol) following general procedure C. LCMS: m/z 368 [M+1]+.

Example 10

1-Cyclopentyl-7-methoxy-3-thiophen-2-yl-1H-pyrimido[5,4-c]quinoline-2,4-dione

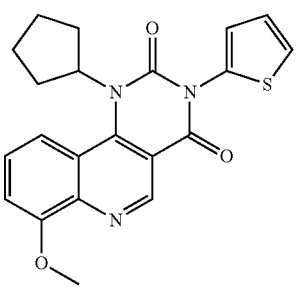 [SMILES: COc1cccc2c1ncc1c(=O)n(-c3cccs3)c(=O)n(C3CCCC3)c12]

1-Cyclopentyl-7-methoxy-3-thiophen-2-yl-1H-pyrimido[5,4-c]quinoline-2,4-dione (19 mg) was prepared from 4-cyclopentylamino-8-methoxy-quinoline-3-carboxylic acid ethyl ester (0.10 mmol) and 2-isocyanatothiophene (0.4 mmol) following general procedure C. LCMS: m/z 394 [M+1]+.

Example 11

3-(1-Cyclopentyl-7-methoxy-2,4-dioxo-1,4-dihydro-2H-pyrimido[5,4-c]quinolin-3-yl)-propionic acid ethyl ester

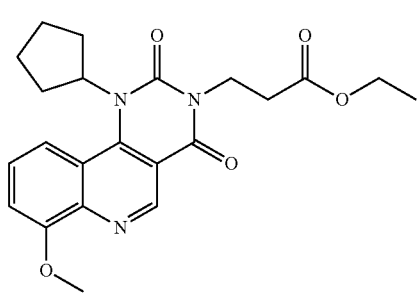 [SMILES: CCOC(=O)CCn1c(=O)c2cnc3c(OC)cccc3c2n(C2CCCC2)c1=O]

4-(1-Cyclopentyl-7-methoxy-2,4-dioxo-1,4-dihydro-2H-pyrimido[5,4-c]quinolin-3-yl)-propionic acid ethyl ester (24 mg) was prepared from 4-cyclopentylamino-8-methoxy-quinoline-3-carboxylic acid ethyl ester (0.10 mmol) and 3-isocyanato-propionic acid ethyl ester (0.4 mmol) following general procedure C. LCMS: m/z 412 [M+1]$^+$.

Example 12

1-Cyclopentyl-3-(2,4-dimethoxy-phenyl)-7-methoxy-1H-pyrimido[5,4-c]quinoline-2,4-dione

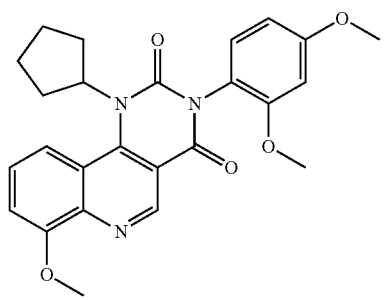 [SMILES: COc1ccc(-n2c(=O)c3cnc4c(OC)cccc4c3n(C3CCCC3)c2=O)c(OC)c1]

1-Cyclopentyl-3-(2,4-dimethoxy-phenyl)-7-methoxy-1H-pyrimido[5,4-c]quinoline-2,4-dione (25 mg) was prepared from 4-cyclopentylamino-8-methoxy-quinoline-3-carboxylic acid ethyl ester (0.10 mmol) and 2,4-dimethoxyphenyl isocyanate (0.4 mmol) following general procedure C. LCMS: m/z 448 [M+1]$^+$.

Example 13

1-Cyclopentyl-7-methoxy-1H-pyrimido[5,4-c]quinoline-2,4-dione

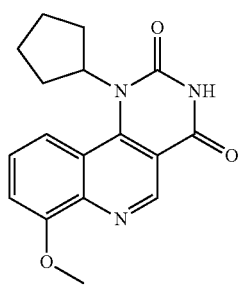 [SMILES: COc1cccc2c1ncc1c(=O)[nH]c(=O)n(C3CCCC3)c12]

1-Cyclopentyl-7-methoxy-1H-pyrimido[5,4-c]quinoline-2,4-dione (8 mg) was prepared from 3-tert-butyl-1-cyclopentyl-7-methoxy-1H-pyrimido[5,4-c]quinoline-2,4-dione (18 mg, 0.05 mmol) with treatment of trifluoroacetic acid (20 L) in DCM (1 mL). LCMS: m/z 312 [M+1]$^+$.

Example 14

1-Isopropyl-7-methoxy-3-propyl-1H-pyrimido[5,4-c]quinoline-2,4-dione

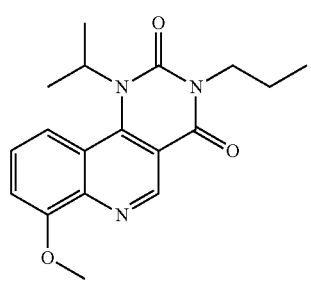 [SMILES: CCCn1c(=O)c2cnc3c(OC)cccc3c2n(C(C)C)c1=O]

1-Isopropyl-7-methoxy-3-propyl-1H-pyrimido[5,4-c]quinoline-2,4-dione (23 mg) was prepared from 4-isopropylamino-8-methoxy-quinoline-3-carboxylic acid ethyl ester (60 mg, 0.20 mmol) and n-propyl isocyanate (1.0 mmol) following general procedure C. LCMS: m/z 328 [M+1]$^+$.

Example 15

1,3-Diisopropyl-7-methoxy-1H-pyrimido[5,4-c]quinoline-2,4-dione

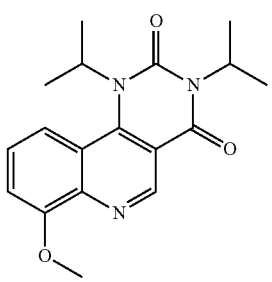 [SMILES: COc1cccc2c1ncc1c(=O)n(C(C)C)c(=O)n(C(C)C)c12]

1,3-Diisopropyl-7-methoxy-1H-pyrimido[5,4-c]quinoline-2,4-dione (21 mg) was prepared from 4-isopropylamino-8-methoxy-quinoline-3-carboxylic acid ethyl ester (59.6 mg, 0.20 mmol) and isopropyl isocyanate (1.0 mmol) following general procedure C. LCMS: m/z 328 [M+1]$^+$.

Example 16

3-Ethyl-7-methoxy-1-propyl-1H-pyrimido[5,4-c]quinoline-2,4-dione

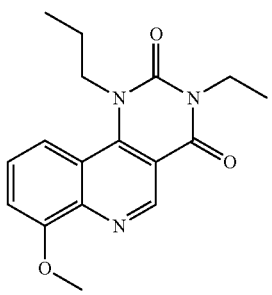 [SMILES: CCCn1c(=O)n(CC)c(=O)c2cnc3c(OC)cccc3c21]

4-Chloro-8-methoxy-quinoline-3-carboxylic acid ethyl ester (250 mg, 0.94 mmol) was treated with 1-aminopropane following general procedure B to afford 8-methoxy-4-propylamino-quinoline-3-carboxylic acid ethyl ester (260 mg). Thus obtained amino-ester was hydrolyzed to the corresponding acid in quantitative yield using general procedure D and then transformed into 8-methoxy-4-propylamino-quinoline-3-carboxylic acid ethylamide (200 mg) following general procedure E. The above ethylamide (0.70 mmol) was subjected to reaction with methyl chloroformate according to general procedure F to furnish 3-ethyl-7-methoxy-1-propyl-1H-pyrimido[5,4-c]quinoline-2,4-dione (26 mg). LCMS: m/z 314 [M+1]$^+$.

Example 17

1-Butyl-3-ethyl-7-methoxy-1H-pyrimido[5,4-c]quinoline-2,4-dione

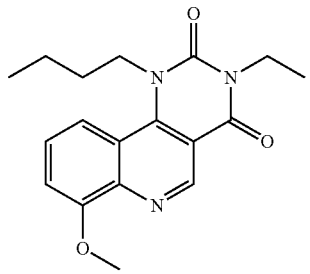 [SMILES: CCCCn1c(=O)n(CC)c(=O)c2cnc3c(OC)cccc3c21]

4-Chloro-8-methoxy-quinoline-3-carboxylic acid ethyl ester (300 mg, 1.13 mmol) was treated with 1-aminobutane following general procedure B to afford 4-butylamino-8-methoxy-quinoline-3-carboxylic acid ethyl ester (295 mg). Thus obtained amino-ester was hydrolyzed to the corresponding acid in quantitative yield using general procedure D and then transformed into the corresponding ethylamide (220 mg) following general procedure E.

The above ethylamide (0.73 mmol) was subjected to reaction with methyl chloroformate according to general procedure F to furnish 1-butyl-3-ethyl-7-methoxy-1H-pyrimido[5,4-c]quinoline-2,4-dione (70 mg). LCMS: m/z 328 [M+1]$^+$.

Example 18

3-Ethyl-1-isobutyl-7-methoxy-1H-pyrimido[5,4-c]quinoline-2,4-dione

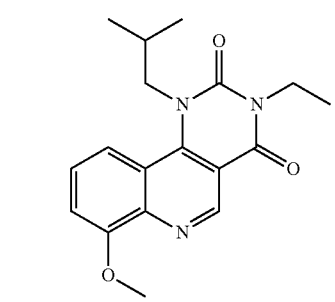 [SMILES: CCn1c(=O)c2cnc3c(OC)cccc3c2n(CC(C)C)c1=O]

4-Chloro-8-methoxy-quinoline-3-carboxylic acid ethyl ester (300 mg, 1.13 mmol) was treated with isobutylamine following general procedure B to afford 4-isobutylamino-8-methoxy-quinoline-3-carboxylic acid ethyl ester (280 mg). Thus obtained amino-ester was hydrolyzed to the corresponding acid in quantitative yield using general procedure D and then transformed into the corresponding ethylamide (180 mg) following general procedure E. The above ethylamide (0.6 mmol) was subjected to reaction with methyl chloroformate according to general procedure F to furnish 3-ethyl-1- isobutyl-7-methoxy-1H-pyrimido[5,4-c]quinoline-2,4-dione (22 mg). LCMS: m/z 328 [M+1]+.

Example 19

3-Ethyl-7-methoxy-1-(tetrahydro-furan-2-ylmethyl)-1H-pyrimido[5,4-c]quinoline-2,4-dione

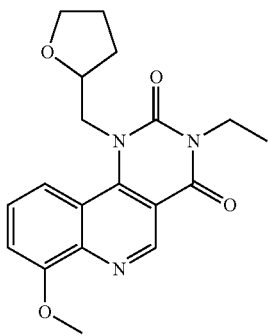 [SMILES: CCn1c(=O)c2cnc3c(OC)cccc3c2n(CC2CCCO2)c1=O]

4-Chloro-8-methoxy-quinoline-3-carboxylic acid ethyl ester (300 mg, 1.13 mmol) was treated with furfurylamine following general procedure B to afford 8-methoxy-4-[(tetrahydro-furan-2-ylmethyl)-amino]-quinoline-3-carboxylic acid ethyl ester (280 mg). Thus obtained amino-ester was hydrolyzed to the corresponding acid in quantitative yield using general procedure D and then transformed into the corresponding ethylamide (220 mg) following general procedure E. The above ethylamide (0.67 mmol) was subjected to reaction with methyl chloroformate according to general procedure F to furnish 3-ethyl-7-methoxy-1-(tetrahydro-furan-2-ylmethyl)-1H-pyrimido[5,4-c]quinoline-2,4-dione (30 mg). LCMS: m/z 356 [M+1]+.

Example 20

1,3-Diethyl-7-methoxy-1H-pyrimido[5,4-c]quinoline-2,4-dione

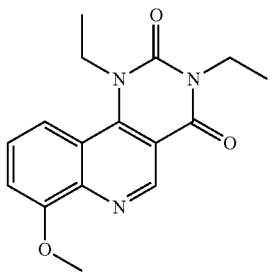 [SMILES: CCn1c(=O)c2cnc3c(OC)cccc3c2n(CC)c1=O]

4-Chloro-8-methoxy-quinoline-3-carboxylic acid ethyl ester (300 mg, 1.13 mmol) was treated with ethylamine following general procedure B to afford 4-ethylamino-8-methoxy-quinoline-3-carboxylic acid ethyl ester (220 mg). Thus obtained amino-ester was hydrolyzed to the corresponding acid in quantitative yield using general procedure D and then transformed into the corresponding ethylamide (180 mg) following general procedure E. The above ethylamide (0.65 mmol) was subjected to reaction with methyl chloroformate according to general procedure F to furnish 1,3-diethyl-7-methoxy-1H-pyrimido[5,4-c]quinoline-2,4-dione (20 mg). LCMS: m/z 300 [M+1]+. LCMS: m/z 300 [M+1]+. 1H NMR (400 MHz, CDCl3): δ 9.48 (s, 1H), 7.87 (d, 1H), 7.56 (t, 1H), 7.22 (d, 1H), 4.42 (q, 2H), 4.16 (q, 2H), 4.12 (s, 3H), 1.73 (t, 3H), and 1.33 (t, 3H) ppm.

Example 21

1-Cyclopropyl-3-ethyl-7-methoxy-1H-pyrimido[5,4-c]quinoline-2,4-dione

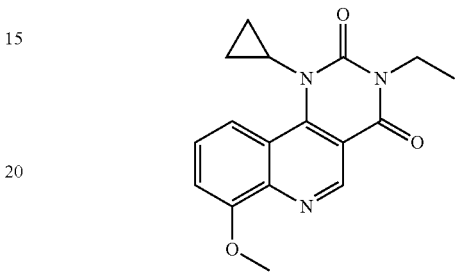

4-Chloro-8-methoxy-quinoline-3-carboxylic acid ethyl ester (300 mg, 1.13 mmol) was treated with cyclopropylamine following general procedure B to afford 4-cyclopropylamino-8-methoxy-quinoline-3-carboxylic acid ethyl ester (200 mg). Thus obtained amino-ester was hydrolyzed to the corresponding acid in quantitative yield using general procedure D and then transformed into the corresponding ethylamide (170 mg) following general procedure E. The above ethylamide (0.6 mmol) was subjected to reaction with methyl chloroformate according to general procedure F to furnish 1-cyclopropyl-3-ethyl-7-methoxy-1H-pyrimido[5,4-c]quinoline-2,4-dione (15 mg). LCMS: m/z 312 [M+1]+.

Example 22

1-Cyclobutyl-3-ethyl-7-methoxy-1H-pyrimido[5,4-c]quinoline-2,4-dione

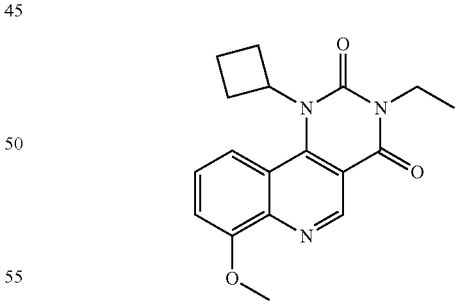

4-Chloro-8-methoxy-quinoline-3-carboxylic acid ethyl ester (300 mg, 1.13 mmol) was treated with cyclobutylamine following general procedure B to afford 4-cyclobutylamino-8-methoxy-quinoline-3-carboxylic acid ethyl ester (240 mg). Thus obtained amino-ester was hydrolyzed to the corresponding acid using general procedure D and then transformed into the corresponding ethylamide (170 mg) following general procedure E.

The above ethylamide (0.60 mmol) was subjected to reaction with methyl chloroformate according to general procedure F to furnish 1-cyclobutyl-3-ethyl-7-methoxy-1H-pyrimido[5,4-c]quinoline-2,4-dione (20 mg). LCMS: m/z 312 [M+1]⁺.

Example 23

3-Ethyl-1-(1-ethyl-propyl)-7-methoxy-1H-pyrimido[5,4-c]quinoline-2,4-dione

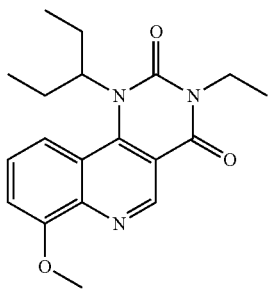 [SMILES: CCC(CC)n1c(=O)n(CC)c(=O)c2cnc3c(OC)cccc3c21]

4-Chloro-8-methoxy-quinoline-3-carboxylic acid ethyl ester (250 mg, 0.94 mmol) was treated with 1-ethyl-propylamine following general procedure B to afford 4-(1-ethyl-propylamino)-8-methoxy-quinoline-3-carboxylic acid ethyl ester (240 mg). Thus obtained amino-ester was hydrolyzed to the corresponding acid in quantitative yield using general procedure D and then transformed into the corresponding ethylamide (160 mg) following general procedure E.

The above ethylamide (0.51 mmol) was subjected to reaction with methyl chloroformate according to general procedure F to furnish 3-ethyl-1-(1-ethyl-propyl)-7-methoxy-1H-pyrimido[5,4-c]quinoline-2,4-dione (15 mg). LCMS: m/z 342 [M+1]⁺.

Example 24

3-Ethyl-7-methoxy-1-(tetrahydro-furan-3-yl)-1H-pyrimido[5,4-c]quinoline-2,4-dione

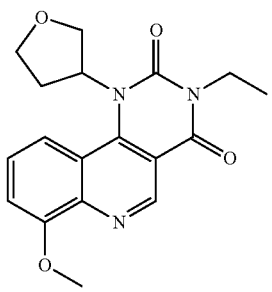 [SMILES: CCn1c(=O)c2cnc3c(OC)cccc3c2n(C2CCOC2)c1=O]

4-Chloro-8-methoxy-quinoline-3-carboxylic acid ethyl ester (300 mg, 1.13 mmol) was treated with tetrahydro-furan-3-ylamine following general procedure B to afford 8-methoxy-4-(tetrahydro-furan-3-ylamino)-quinoline-3-carboxylic acid ethyl ester (275 mg). Thus obtained amino-ester was hydrolyzed to the corresponding acid in quantitative yield using general procedure D and then transformed into the corresponding ethylamide (190 mg) following general procedure E. The above ethylamide (0.6 mmol) was subjected to reaction with methyl chloroformate according to general procedure F to furnish 3-ethyl-7-methoxy-1-(tetrahydro-furan-3-yl)-1H-pyrimido[5,4-c]quinoline-2,4-dione (10 mg). LCMS: m/z 342 [M+1]⁺.

Example 25

3-Ethyl-7-methoxy-1-(3-methoxy-propyl)-1H-pyrimido[5,4-c]quinoline-2,4-dione

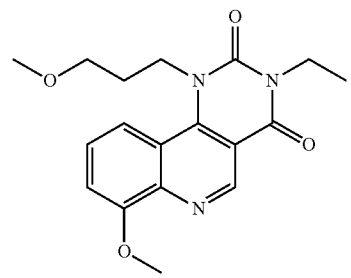 [SMILES: CCn1c(=O)c2cnc3c(OC)cccc3c2n(CCCOC)c1=O]

4-Chloro-8-methoxy-quinoline-3-carboxylic acid ethyl ester (250 mg, 0.94 mmol) was treated with 3-methoxy-propylamine following general procedure B to afford 8-methoxy-4-(3-methoxy-propyl-amino)-quinoline-3-carboxylic acid ethyl ester (260 mg). Thus obtained amino-ester was hydrolyzed to the corresponding acid in quantitative yield using general procedure D and then transformed into the corresponding ethylamide (180 mg) following general procedure E. The above ethylamide (0.57 mmol) was subjected to reaction with methyl chloroformate according to general procedure F to furnish 3-ethyl-7-methoxy-1-(3-methoxy-propyl)-1H-pyrimido[5,4-c]quinoline-2,4-dione (35 mg). LCMS: m/z 344 [M+1]⁺.

Example 26

1-(2,2-Dimethyl-propyl)-3-ethyl-7-methoxy-1H-pyrimido[5,4-c]quinoline-2,4-dione

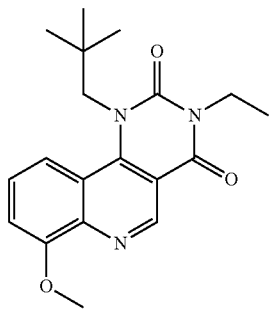 [SMILES: CCn1c(=O)c2cnc3c(OC)cccc3c2n(CC(C)(C)C)c1=O]

4-Chloro-8-methoxy-quinoline-3-carboxylic acid ethyl ester (250 mg, 0.94 mmol) was treated with 2,2-dimethyl-propylamine following general procedure B to afford 4-(2,2-dimethyl-propylamino)-8-methoxy-quinoline-3-carboxylic acid ethyl ester (220 mg). Thus obtained amino-ester was hydrolyzed to the corresponding acid in quantitative yield using general procedure D and then transformed into the corresponding ethylamide (160 mg) following general procedure E. The above ethylamide (0.50 mmol) was subjected to reaction with methyl chloroformate according to general procedure F to furnish 1-(2,2-dimethyl-propyl)-3-ethyl-7-methoxy-1H-pyrimido[5,4-c]quinoline-2,4-dione (5 mg). LCMS: m/z 342 [M+1]⁺.

Example 27

3-Ethyl-7-methoxy-1-(4,4,4-trifluoro-butyl)-1H-pyrimido[5,4-c]quinoline-2,4-dione

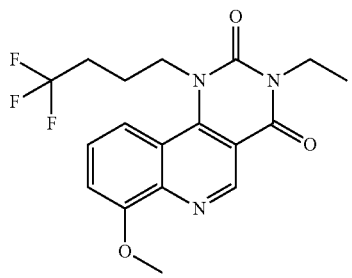 [SMILES: CCn1c(=O)c2cnc3c(OC)cccc3c2n(CCCC(F)(F)F)c1=O]

4-Chloro-8-methoxy-quinoline-3-carboxylic acid ethyl ester (250 mg, 0.94 mmol) was treated with 4,4,4-trifluoro-butylamine following general procedure B to afford 8-methoxy-4-(4,4,4-trifluoro-butylamino)-quinoline-3-carboxylic acid ethyl ester (210 mg). Thus obtained amino-ester was hydrolyzed to the corresponding acid in quantitative yield using general procedure D and then transformed into the corresponding ethylamide (170 mg) following general procedure E. The above ethylamide (0.48 mmol) was subjected to reaction with methyl chloroformate according to general procedure F to furnish 3-ethyl-7-methoxy-1-(4,4,4-trifluoro-butyl)-1H-pyrimido[5,4-c]quinoline-2,4-dione (70 mg). LCMS: m/z 382 [M+1]⁺.

Example 28

9-Chloro-1-cyclopentyl-3-ethyl-7-methoxy-1H-pyrimido[5,4-c]quinoline-2,4-dione

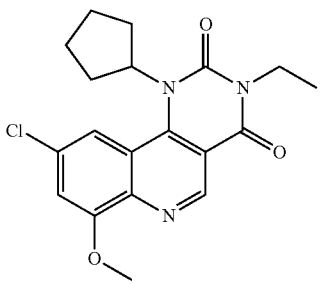 [SMILES: CCn1c(=O)c2cnc3c(OC)cc(Cl)cc3c2n(C2CCCC2)c1=O]

4,6-Dichloro-8-methoxy-quinoline-3-carboxylic acid ethyl ester (250 mg, 0.83 mmol) was treated with cyclopentylamine following general procedure B to afford 6-chloro-4-cyclopentylamino-8-methoxy-quinoline-3-carboxylic acid ethyl ester (240 mg). Thus obtained amino-ester was hydrolyzed to the corresponding acid in quantitative yield using general procedure D and then transformed into the corresponding ethylamide (170 mg) following general procedure E.

The above ethylamide (0.49 mmol) was subjected to reaction with methyl chloroformate according to general procedure F to furnish 9-chloro-1-cyclopentyl-3-ethyl-7-methoxy-1H-pyrimido[5,4-c]quinoline-2,4-dione (15 mg). LCMS: m/z 374 [M+1]⁺.

Example 29

1-Cyclopentyl-3-ethyl-9-fluoro-7-methoxy-1H-pyrimido[5,4-c]quinoline-2,4-dione

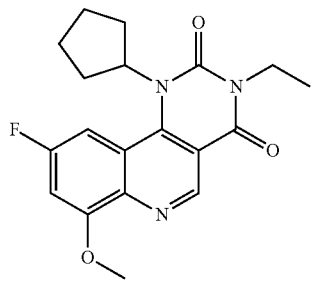 [SMILES: CCn1c(=O)c2cnc3c(OC)cc(F)cc3c2n(C2CCCC2)c1=O]

4-Chloro-6-fluoro-8-methoxy-quinoline-3-carboxylic acid ethyl ester (250 mg, 0.89 mmol) was treated with cyclopentylamine following general procedure B to afford 4-cyclopentylamino-6-fluoro-8-methoxy-quinoline-3-carboxylic acid ethyl ester (200 mg). Thus obtained amino-ester was hydrolyzed to the corresponding acid in quantitative yield using general procedure D and then transformed into the corresponding ethylamide (140 mg) following general procedure E. The above ethylamide (0.42 mmol) was subjected to reaction with methyl chloroformate according to general procedure F to furnish 1-cyclopentyl-3-ethyl-9-fluoro-7-methoxy-1H-pyrimido[5,4-c]quinoline-2,4-dione (13 mg). LCMS: m/z 358 [M+1]⁺.

Example 30

7-Chloro-1-cyclopentyl-3-ethyl-1H-pyrimido[5,4-c]quinoline-2,4-dione

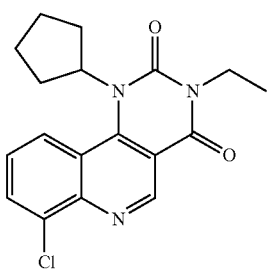 [SMILES: CCn1c(=O)c2cnc3c(Cl)cccc3c2n(C2CCCC2)c1=O]

4,8-Dichloro-quinoline-3-carboxylic acid ethyl ester (250 mg, 0.93 mmol) was treated with cyclopentylamine following general procedure B to afford 8-chloro-4-cyclopentylamino-quinoline-3-carboxylic acid ethyl ester (220 mg). Thus obtained amino-ester was hydrolyzed to the corresponding acid in quantitative yield using general procedure D and then transformed into the corresponding ethylamide (165 mg) following general procedure E.

The above ethylamide (0.52 mmol) was subjected to reaction with methyl chloroformate according to general procedure F to furnish 7-chloro-1-cyclopentyl-3-ethyl-1H-pyrimido[5,4-c]quinoline-2,4-dione (15 mg). LCMS: m/z 344 [M+1]⁺.

Example 31

1-Cyclopentyl-3,7-diethyl-1H-pyrimido[5,4-c]quinoline-2,4-dione

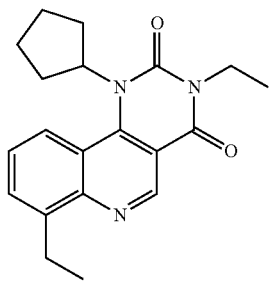 [SMILES: CCc1cccc2c1ncc1c(=O)n(CC)c(=O)n(C3CCCC3)c12]

4-Chloro-8-ethyl-quinoline-3-carboxylic acid ethyl ester (250 mg, 0.95 mmol) was treated with cyclopentylamine following general procedure B to afford 4-cyclopentylamino-8-ethyl-quinoline-3-carboxylic acid ethyl ester (250 mg). Thus obtained amino-ester was hydrolyzed to the corresponding acid in quantitative yield using general procedure D and then transformed into the corresponding ethylamide (180 mg) following general procedure E.

The above ethylamide (0.58 mmol) was subjected to reaction with methyl chloroformate according to general procedure F to furnish 1-cyclopentyl-3,7-diethyl-1H-pyrimido[5,4-c]quinoline-2,4-dione (20 mg). LCMS: m/z 338 [M+1]⁺.

Example 32

1-Cyclopentyl-3-ethyl-7-propyl-1H-pyrimido[5,4-c]quinoline-2,4-dione

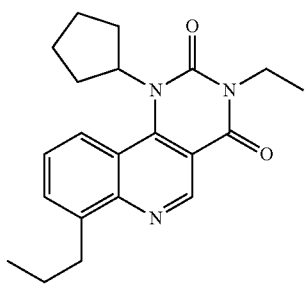 [SMILES: CCCc1cccc2c1ncc1c(=O)n(CC)c(=O)n(C3CCCC3)c12]

4-Chloro-8-propyl-quinoline-3-carboxylic acid ethyl ester (250 mg, 0.9 mmol) was treated with cyclopentylamine following general procedure B to afford 4-cyclopentylamino-8-propyl-quinoline-3-carboxylic acid ethyl ester (260 mg). Thus obtained amino-ester was hydrolyzed to the corresponding acid using general procedure D and then transformed into the corresponding ethylamide (170 mg) following general procedure E.

The above ethylamide (0.52 mmol) was subjected to reaction with methyl chloroformate according to general procedure F to furnish 1-cyclopentyl-3-ethyl-7-propyl-1H-pyrimido[5,4-c]quinoline-2,4-dione (25 mg). LCMS: m/z 352 [M+1]⁺.

Example 33

1-Cyclopentyl-3-ethyl-7-isopropyl-1H-pyrimido[5,4-c]quinoline-2,4-dione

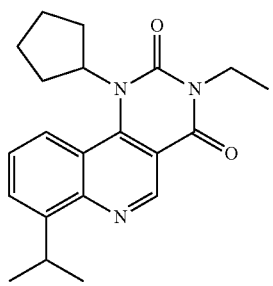 [SMILES: CCn1c(=O)c2cnc3c(C(C)C)cccc3c2n(C2CCCC2)c1=O]

4-Chloro-8-isopropyl-quinoline-3-carboxylic acid ethyl ester (250 mg, 0.9 mmol) was treated with cyclopentylamine following general procedure B to afford 4-cyclopentylamino-8-isopropyl-quinoline-3-carboxylic acid ethyl ester (240 mg). Thus obtained amino-ester was hydrolyzed to the corresponding acid using general procedure D and then transformed into the corresponding ethylamide (165 mg) following general procedure E.

The above ethylamide (0.52 mmol) was subjected to reaction with methyl chloroformate according to general procedure F to furnish 1-cyclopentyl-3-ethyl-7-isopropyl-1H-pyrimido[5,4-c]quinoline-2,4-dione (30 mg). LCMS: m/z 352 [M+1]⁺.

Example 34

1-Cyclopentyl-3-ethyl-7-trifluoromethoxy-1H-pyrimido[5,4-c]quinoline-2,4-dione

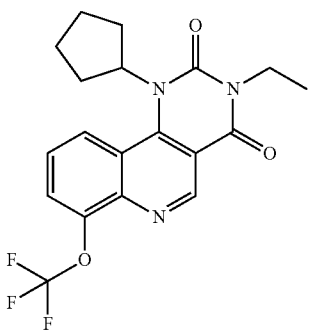 [SMILES: CCn1c(=O)c2cnc3c(OC(F)(F)F)cccc3c2n(C2CCCC2)c1=O]

4-Chloro-8-trifluoromethoxy-quinoline-3-carboxylic acid ethyl ester (250 mg, 0.94 mmol) was treated with cyclopentylamine following general procedure B to afford 4-cyclopentylamino-8-trifluoromethoxy-quinoline-3-carboxylic acid ethyl ester (220 mg). Thus obtained amino-ester was hydrolyzed to the corresponding acid using general procedure D and then transformed into the corresponding ethylamide (180 mg) following general procedure E. The above ethylamide (0.54 mmol) was subjected to reaction with methyl chloroformate according to general procedure F to furnish 1-cyclopentyl-3-ethyl-7-trifluoromethoxy-1H-pyrimido[5,4-c]quinoline-2,4-dione (60 mg). LCMS: m/z 394 [M+1]⁺.

Example 35

1-Benzyl-3-ethyl-7-methoxy-1H-pyrimido[5,4-c]quinoline-2,4-dione

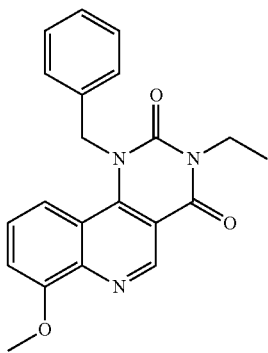 [SMILES: CCn1c(=O)c2cnc3c(OC)cccc3c2n(Cc2ccccc2)c1=O]

4-Chloro-8-methoxy-quinoline-3-carboxylic acid ethyl ester (250 mg, 0.94 mmol) was treated with benzylamine following general procedure B to afford 4-benzylamino-8-methoxy-quinoline-3-carboxylic acid ethyl ester (220 mg). Thus obtained amino-ester was hydrolyzed to the corresponding acid using general procedure D and then transformed into the corresponding ethylamide (180 mg) following general procedure E. The above ethylamide (0.54 mmol) was subjected to reaction with methyl chloroformate according to general procedure F to furnish 1-benzyl-3-ethyl-7-methoxy-1H-pyrimido[5,4-c]quinoline-2,4-dione (60 mg). LCMS: m/z 362 [M+1]⁺.

Example 36

3-Ethyl-7-methoxy-1-(tetrahydro-pyran-4-ylmethyl)-1H-pyrimido[5,4-c]quinoline-2,4-dione

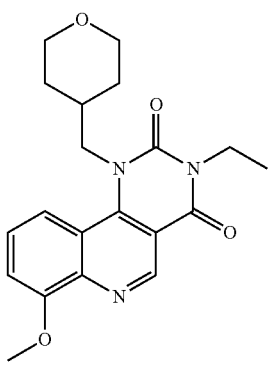 [SMILES: CCn1c(=O)c2cnc3c(OC)cccc3c2n(CC2CCOCC2)c1=O]

4-Chloro-8-methoxy-quinoline-3-carboxylic acid ethyl ester (265 mg, 1.0 mmol) was treated with C-(tetrahydro-pyran-4-yl)-methylamine (1.5 mmol) following general procedure B to afford 8-methoxy-4-[(tetrahydro-pyran-4-ylmethyl)-amino]-quinoline-3-carboxylic acid ethyl ester (324 mg). 3-Ethyl-7-methoxy-1-(tetrahydro-pyran-4-ylmethyl)-1H-pyrimido[5,4-c]quinoline-2,4-dione (19 mg) was prepared from 8-methoxy-4-[(tetrahydro-pyran-4-ylmethyl)-amino]-quinoline-3-carboxylic acid ethyl ester (0.10 mmol) and ethyl isocyanate (0.4 mmol) following general procedure C. LCMS: m/z 370 [M+1]⁺.

Example 37

3-Ethyl-1-isopropyl-7-methoxy-1H-pyrimido[5,4-c]quinoline-2,4-dione

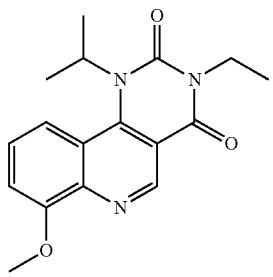 [SMILES: CCn1c(=O)c2cnc3c(OC)cccc3c2n(C(C)C)c1=O]

4-Chloro-8-methoxy-quinoline-3-carboxylic acid ethyl ester (267 mg, 1.0 mmol) was treated with isopropylamine (1.5 mmol) following general procedure B to afford 4-isopropylamino-8-methoxy-quinoline-3-carboxylic acid ethyl ester (256 mg). 3-Ethyl-1-isopropyl-7-methoxy-1H-pyrimido[5,4-c]quinoline-2,4-dione (14 mg) was prepared from 4-isopropylamino-8-methoxy-quinoline-3-carboxylic acid ethyl ester (0.10 mmol) and ethyl isocyanate (0.4 mmol) following general procedure C. LCMS: m/z 314 [M+1]⁺.

Example 38

3-sec-Butyl-1-cyclopentyl-7-methoxy-1H-pyrimido[5,4-c]quinoline-2,4-dione

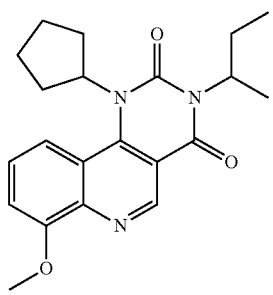 [SMILES: CCC(C)n1c(=O)c2cnc3c(OC)cccc3c2n(C2CCCC2)c1=O]

3-sec-Butyl-1-cyclopentyl-7-methoxy-1H-pyrimido[5,4-c]quinoline-2,4-dione (25 mg) was prepared from 4-cyclopentylamino-8-methoxy-quinoline-3-carboxylic acid ethyl ester (0.10 mmol) and 2-butyl isocyanate (0.4 mmol) following general procedure C. LCMS: m/z 368 [M+1]+.

Example 39

1-Cyclopentyl-7-methoxy-3-phenyl-1H-pyrimido[5,4-c]quinoline-2,4-dione

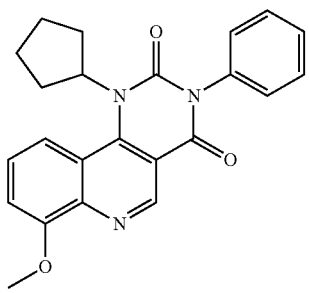 [SMILES: COc1cccc2c1ncc1c(=O)n(-c3ccccc3)c(=O)n(C3CCCC3)c12]

1-Cyclopentyl-7-methoxy-3-phenyl-1H-pyrimido[5,4-c]quinoline-2,4-dione (29 mg) was prepared from 4-cyclopentylamino-8-methoxy-quinoline-3-carboxylic acid ethyl ester (0.10 mmol) and phenyl isocyanate (0.4 mmol) following general procedure C. LCMS: m/z 388 [M+1]+.

Example 40

3-Benzyl-1-cyclopentyl-7-methoxy-1H-pyrimido[5,4-c]quinoline-2,4-dione

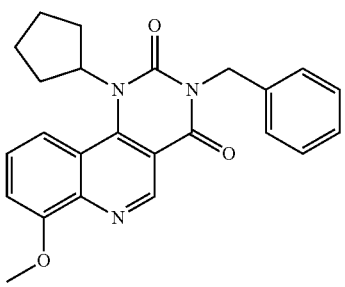 [SMILES: COc1cccc2c1ncc1c(=O)n(Cc3ccccc3)c(=O)n(C3CCCC3)c12]

3-Benzyl-1-cyclopentyl-7-methoxy-1H-pyrimido[5,4-c]quinoline-2,4-dione (28 mg) was prepared from 4-cyclopentylamino-8-methoxy-quinoline-3-carboxylic acid ethyl ester (0.10 mmol) and benzyl isocyanate (0.4 mmol) following general procedure C. LCMS: m/z 402 [M+1]+.

Example 41

1-Cyclopentyl-3-ethyl-7-methyl-1H-pyrimido[5,4-c]quinoline-2,4-dione

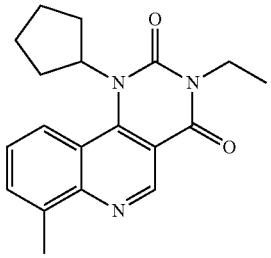 [SMILES: CCn1c(=O)c2cnc3c(C)cccc3c2n(C2CCCC2)c1=O]

4-Chloro-8-methyl-quinoline-3-carboxylic acid ethyl ester (125 mg, 0.5 mmol) was treated with cyclopentylamine following general procedure B to afford 4-Cyclopentylamino-8-methyl-quinoline-3-carboxylic acid ethyl ester (120 mg). Thus obtained amino-ester was hydrolyzed to the corresponding acid using general procedure D and then transformed into the corresponding ethylamide (90 mg) following general procedure E.

The above ethylamide (0.3 mmol) was subjected to reaction with methyl chloroformate according to general procedure F to furnish 1-cyclopentyl-3-ethyl-7-methyl-1H-pyrimido[5,4-c]quinoline-2,4-dione (10 mg). LCMS: m/z 324 [M+1]+.

Example 42

1-Cyclopentyl-3-ethyl-1H-pyrimido[5,4-c]quinoline-2,4-dione

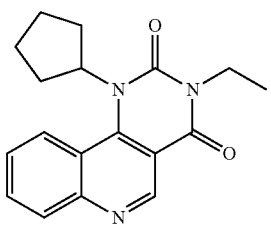 [SMILES: CCn1c(=O)c2cnc3ccccc3c2n(C2CCCC2)c1=O]

4-Chloro-quinoline-3-carboxylic acid ethyl ester (125 mg, 0.53 mmol) was treated with cyclopentylamine following general procedure B to afford 4-Cyclopentylamino-quinoline-3-carboxylic acid ethyl ester (110 mg). Thus obtained amino-ester was hydrolyzed to the corresponding acid using general procedure D and then transformed into the corresponding ethylamide (80 mg) following general procedure E. The above ethylamide (0.28 mmol) was subjected to reaction with methyl chloroformate according to general procedure F to furnish 1-cyclopentyl-3-ethyl-1H-pyrimido[5,4-c]quinoline-2,4-dione (15 mg). LCMS: m/z 310 [M+1]+.

Example 43

3-Ethyl-7-methoxy-1-(4-methoxy-benzyl)-1H-pyrimido[5,4-c]quinoline-2,4-dione

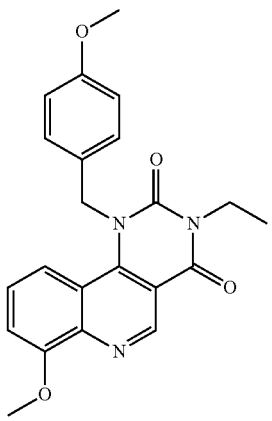 [SMILES: CCn1c(=O)c2cnc3c(OC)cccc3c2n(Cc2ccc(OC)cc2)c1=O]

4-Chloro-8-methoxy-quinoline-3-carboxylic acid ethyl ester (250 mg, 0.94 mmol) was treated with 4-methoxybenzylamine following general procedure B to afford 8-methoxy-4-(4-methoxy-benzylamino)-quinoline-3-carboxylic acid ethyl ester (290 mg). Thus obtained amino-ester was hydrolyzed to the corresponding acid using general procedure D and then transformed into the corresponding ethylamide (190 mg) following general procedure E. The above ethylamide (0.41 mmol) was subjected to reaction with methyl chloroformate according to general procedure F to furnish 3-ethyl-7-methoxy-1-(4-methoxy-benzyl)-1H-pyrimido[5,4-c]quinoline-2,4-dione (110 mg). LCMS: m/z 422 [M+1]+.

Example 44

3-Ethyl-7-methoxy-1H-pyrimido[5,4-c]quinoline-2,4-dione

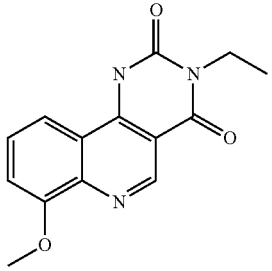 [SMILES: CCn1c(=O)[nH]c2c(cnc3c(OC)cccc32)c1=O]

3-Ethyl-7-methoxy-1H-pyrimido[5,4-c]quinoline-2,4-dione (25 mg) was prepared from 3-ethyl-7-methoxy-1-(4-methoxy-benzyl)-1H-pyrimido[5,4-c]quinoline-2,4-dione (50 mg, 0.11 mmol) via treatment of trifluoroacetic acid in DCM (1 mL). LCMS: m/z 272 [M+1]+.

Example 45

3-Ethyl-7-methoxy-1-(4-methyl-cyclohexyl)-1H-pyrimido[5,4-c]quinoline-2,4-dione

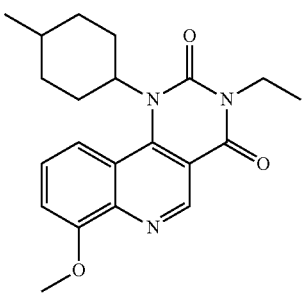 [SMILES: CCn1c(=O)c2cnc3c(OC)cccc3c2n(C2CCC(C)CC2)c1=O]

4-Chloro-8-methoxy-quinoline-3-carboxylic acid ethyl ester (250 mg, 0.94 mmol) was treated with 4-methyl-cyclohexylamine following general procedure B to afford 8-methoxy-4-(4-methyl-cyclohexylamino)-quinoline-3-carboxylic acid ethyl ester (290 mg). Thus obtained amino-ester was hydrolyzed to the corresponding acid using general procedure D and then transformed into the corresponding ethylamide (200 mg) following general procedure E. The above ethylamide (0.41 mmol) was subjected to reaction with methyl chloroformate according to general procedure F to furnish 3-ethyl-7-methoxy-1-(4-methyl-cyclohexyl)-1H-pyrimido[5,4-c]quinoline-2,4-dione (22 mg). LCMS: m/z 368 [M+1]+.

Example 46

(1-Cyclopentyl-7-methoxy-2,4-dioxo-1,4-dihydro-2H-pyrimido[5,4-c]quinolin-3-yl)-acetic acid ethyl ester

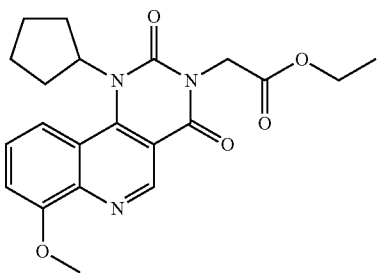 [SMILES: CCOC(=O)Cn1c(=O)c2cnc3c(OC)cccc3c2n(C2CCCC2)c1=O]

(1-Cyclopentyl-7-methoxy-2,4-dioxo-1,4-dihydro-2H-pyrimido[5,4-c]quinolin-3-yl)-acetic acid ethyl ester (24 mg) was prepared from 4-cyclopentylamino-8-methoxy-quinoline-3-carboxylic acid ethyl ester (0.1 mmol) and isocyanatoacetic acid ethyl ester (0.5 mmol) following general procedure C. LCMS: m/z 398 [M+1]+.

Example 47

3-Ethyl-1-(3-fluoro-propyl)-7-methoxy-1H-pyrimido[5,4-c]quinoline-2,4-dione

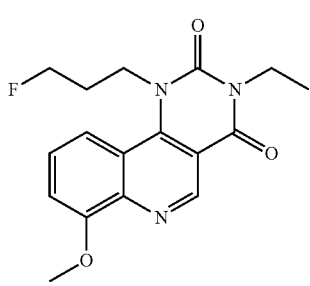 [SMILES: CCn1c(=O)c2cnc3c(OC)cccc3c2n(CCCF)c1=O]

4-Chloro-8-methoxy-quinoline-3-carboxylic acid ethyl ester (250 mg, 0.94 mmol) was treated with 3-fluoro-propylamine following general procedure B to afford 4-(3-fluoro-propylamino)-8-methoxy-quinoline-3-carboxylic acid ethyl ester (262 mg). Thus obtained amino-ester was hydrolyzed to the corresponding acid using general procedure D and then transformed into the corresponding ethylamide (196 mg) following general procedure E. The above ethylamide (0.64 mmol) was subjected to reaction with methyl chloroformate according to general procedure F to furnish 3-ethyl-1-(3-fluoro-propyl)-7-methoxy-1H-pyrimido[5,4-c]quinoline-2,4-dione (138 mg). LCMS: m/z 332 [M+1]+.

Example 48

1-Cyclopentyl-7-methoxy-3-methyl-1H-pyrimido[5,4-c]quinoline-2,4-dione

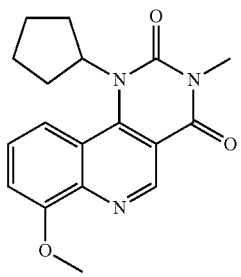 [SMILES: COc1cccc2c1ncc1c(=O)n(C)c(=O)n(C3CCCC3)c12]

1-Cyclopentyl-7-methoxy-3-methyl-1H-pyrimido[5,4-c]quinoline-2,4-dione (18 mg) was prepared from 4-cyclopentylamino-8-methoxy-quinoline-3-carboxylic acid ethyl ester (0.1 mmol) and methyl isocyanate (0.5 mmol) following general procedure C. LCMS: m/z 326 [M+1]+.

Example 49

1-Cyclopentyl-3-(3,5-dimethyl-isoxazol-4-yl)-7-methoxy-1H-pyrimido[5,4-c]quinoline-2,4-dione

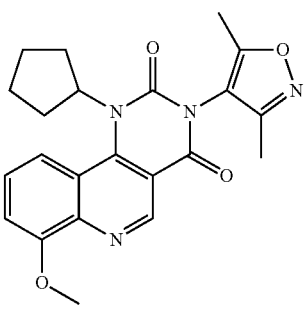 [SMILES: COc1cccc2c1ncc1c(=O)n(-c3c(C)noc3C)c(=O)n(C3CCCC3)c12]

1-Cyclopentyl-3-(3,5-dimethyl-isoxazol-4-yl)-7-methoxy-1H-pyrimido[5,4-c]quinoline-2,4-dione (17 mg) was prepared from 4-cyclopentylamino-8-methoxy-quinoline-3-carboxylic acid ethyl ester (0.1 mmol) and 4-isocyanato-3,5-dimethyl-isoxazole (0.05 mmol) following general procedure C. LCMS: m/z 407 [M+1]+.

Example 50

1-Cyclopentyl-7-methoxy-3-thiophen-3-yl-1H-pyrimido[5,4-c]quinoline-2,4-dione

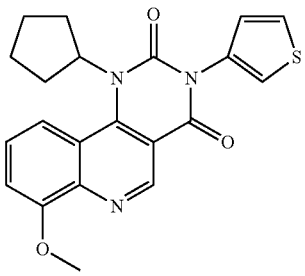 [SMILES: COc1cccc2c1ncc1c(=O)n(-c3ccsc3)c(=O)n(C3CCCC3)c12]

1-Cyclopentyl-7-methoxy-3-thiophen-3-yl-1H-pyrimido[5,4-c]quinoline-2,4-dione (21 mg) was prepared from 4-cyclopentylamino-8-methoxy-quinoline-3-carboxylic acid ethyl ester (0.1. mmol) and 3-isocyanato-thiophene (0.5 mmol) following general procedure C. LCMS: m/z 394 [M+1]+.

Example 51

1-Cyclopentyl-7-methoxy-3-(4-methyl-thiophen-2-yl)-1H-pyrimido[5,4-c]quinoline-2,4-dione

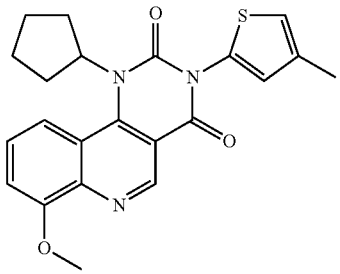 [SMILES: COc1cccc2c1ncc1c(=O)n(-c3cc(C)cs3)c(=O)n(C3CCCC3)c12]

1-Cyclopentyl-7-methoxy-3-(4-methyl-thiophen-2-yl)-1H-pyrimido[5,4-c]quinoline-2,4-dione (26 mg) was prepared from 4-cyclopentylamino-8-methoxy-quinoline-3-carboxylic acid ethyl ester (0.1 mmol) and 2-isocyanato-4-methyl-thiophene (0.5 mmol) following general procedure C. LCMS: m/z 408 [M+1]+. $^1$H NMR (400 MHz, CDCl$_3$): δ 9.44 (s, 1H), 8.32 (s, 1H), 7.80 (d, 1H), 7.63 (t, 1H), 7.28 (d, 1H), 6.89 (s, 1H), 5.05 (p, 1H), 4.10 (s, 3H), 3.02 (s, 3H), 2.29 (m, 2H), 2.11-2.19 (m, 4H), 1.25 (m, 2H) ppm.

Example 52

3-Ethyl-7-methoxy-1-(3-pyrrolidin-1-yl-propyl)-1H-pyrimido[5,4-c]quinoline-2,4-dione

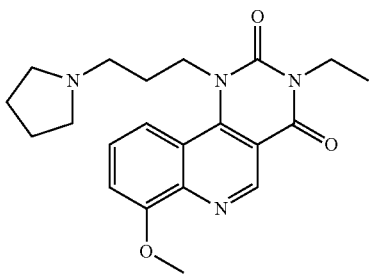 [SMILES: CCn1c(=O)c2cnc3c(OC)cccc3c2n(CCCN2CCCC2)c1=O]

4-Chloro-8-methoxy-quinoline-3-carboxylic acid ethyl ester (266 mg, 1.0 mmol) was treated with 3-pyrrolidin-1-yl-propylamine following general procedure B to afford 8-methoxy-4-(3-pyrrolidin-1-yl-propylamino)-quinoline-3-carboxylic acid ethyl ester (315 mg). Thus obtained amino-ester (36 mg, 0.1 mmol) was subjected to reaction with ethyl isocyanate according to general procedure C to furnish 3-ethyl-7-methoxy-1-(3-pyrrolidin-1-yl-propyl)-1H-pyrimido[5,4-c]quinoline-2,4-dione (19 mg). LCMS: m/z 383 [M+1]+.

Example 53

1-Cyclohexyl-3-ethyl-7-methoxy-1H-pyrimido[5,4-c]quinoline-2,4-dione

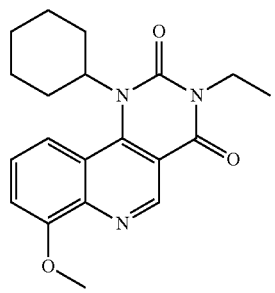 [SMILES: CCn1c(=O)c2cnc3c(OC)cccc3c2n(C2CCCCC2)c1=O]

4-Chloro-8-methoxy-quinoline-3-carboxylic acid ethyl ester (266 mg, 1.0 mmol) was treated with cyclohexylamine following general procedure B to afford 4-cyclohexylamino-8-methoxy-quinoline-3-carboxylic acid ethyl ester (286 mg). Thus obtained amino-ester (33 mg, 0.1 mmol) was subjected to reaction with ethyl isocyanate according to general procedure C to furnish 3-ethyl-7-methoxy-1-(3-pyrrolidin-1-yl-propyl)-1H-pyrimido[5,4-c]quinoline-2,4-dione (15 mg). LCMS: m/z 354 [M+1]+. $^1$H NMR (400 MHz, CDCl$_3$): δ 9.58 (s, 1H), 7.58 (m, 1H), 7.50 (m, 1H), 7.41 (m, 1H), 7.24 (m, 1H), 7.06-7.14 (m, 2H), 6.48 (m, 1H), 4.92 (m, 1H), 4.08 (s, 3H), 2.46 (m, 2H), 1.64-1.92 (m, 5H), 1.42 (m, 2H), 1.28 (m, 1H) ppm.

Example 54

1-Cyclopentyl-7-methoxy-3-m-tolyl-1H-pyrimido[5,4-c]quinoline-2,4-dione

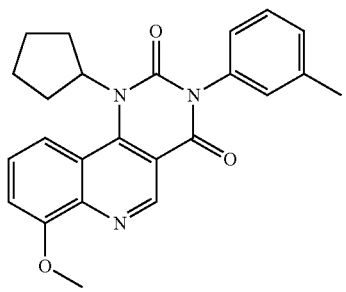 [SMILES: COc1cccc2c1ncc1c(=O)n(-c3cccc(C)c3)c(=O)n(C3CCCC3)c12]

1-Cyclopentyl-7-methoxy-3-m-tolyl-1H-pyrimido[5,4-c]quinoline-2,4-dione (29 mg) was prepared from 4-cyclopentylamino-8-methoxy-quinoline-3-carboxylic acid ethyl ester (0.1 mmol) and 1-isocyanato-3-methyl-benzene (0.5 mmol) following general procedure C. LCMS: m/z 402 [M+1]+. $^1$H NMR (400 MHz, CDCl$_3$): δ 9.46 (s, 1H), 7.77 (d, 1H), 7.53 (t, 1H), 7.46 (d, 1H), 7.32 (s, 1H), 7.16 (d, 1H), 7.14 (d, 1H), 6.83

(d, 1H), 5.06 (p, 1H), 4.12 (s, 3H), 2.41 (m, 2H), 2.32 (s, 3H), 1.98 (m, 4H), 1.32 (m, 2H) ppm.

Example 55

1-Cyclopentyl-7-methoxy-3-p-tolyl-1H-pyrimido[5,4-c]quinoline-2,4-dione

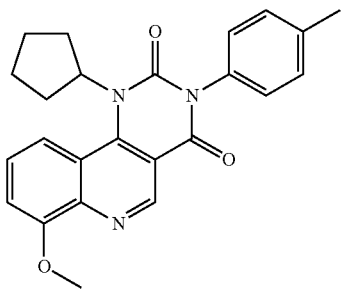 [SMILES: COc1cccc2c1ncc1c(=O)n(-c3ccc(C)cc3)c(=O)n(C3CCCC3)c12]

1-Cyclopentyl-7-methoxy-3-p-tolyl-1H-pyrimido[5,4-c]quinoline-2,4-dione (26 mg) was prepared from 4-cyclopentylamino-8-methoxy-quinoline-3-carboxylic acid ethyl ester (0.1 mmol) and 1-isocyanato-4-methyl-benzene (0.5 mmol) following general procedure C. LCMS: m/z 402 [M+1]$^+$. $^1$H NMR (400 MHz, CDCl$_3$): δ 9.49 (s, 1H), 7.84 (d, 1H), 7.61 (t, 1H), 7.38 (m, 1H), 7.34 (m, 1H), 7.32 (m, 1H), 7.24 (d, 1H), 7.08 (d, 1H), 5.03 (p, 1H), 4.16 (s, 3H), 2.43 (m, 2H), 2.29 (s, 3H), 2.08 (m, 4H), and 1.24 (m, 2H) ppm.

Example 56

8-Chloro-3-ethyl-1-(4-fluoro-butyl)-7-methoxy-1H-pyrimido[5,4-c]quinoline-2,4-dione

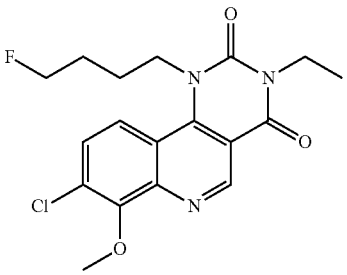 [SMILES: CCn1c(=O)c2cnc3c(OC)c(Cl)ccc3c2n(CCCCF)c1=O]

4,7-Dichloro-8-methoxy-quinoline-3-carboxylic acid ethyl ester (250 mg, 84 mmol) was treated with 4-fluoro-butylamine following general procedure B to afford 7-chloro-4-(4-fluoro-butylamino)-8-methoxy-quinoline-3-carboxylic acid ethyl ester (240 mg). Thus obtained amino-ester was hydrolyzed to the corresponding acid using general procedure D and then transformed into the corresponding ethylamide (175 mg) following general procedure E. The above ethylamide (0.52 mmol) was subjected to reaction with methyl chloroformate according to general procedure F to furnish 8-chloro-3-ethyl-1-(4-fluoro-butyl)-7-methoxy-1H-pyrimido[5,4-c]quinoline-2,4-dione (117 mg). LCMS: m/z 380 [M+1]$^+$.

Example 57

1-Butyl-3-ethyl-9-fluoro-7-methoxy-1H-pyrimido[5,4-c]quinoline-2,4-dione

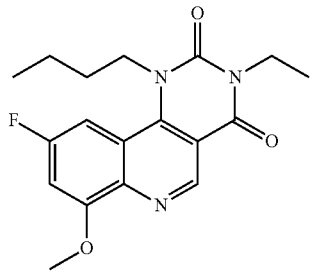 [SMILES: CCCCn1c(=O)n(CC)c(=O)c2cnc3c(OC)cc(F)cc3c21]

4-Chloro-6-fluoro-8-methoxy-quinoline-3-carboxylic acid ethyl ester (250 mg, 0.88 mmol) was treated with butylamine following general procedure B to afford 4-butylamino-6-fluoro-8-methoxy-quinoline-3-carboxylic acid ethyl ester (282 mg). Thus obtained amino-ester was hydrolyzed to the corresponding acid using general procedure D and then transformed into the corresponding ethylamide (170 mg) following general procedure E. The above ethylamide (0.170 mmol) was subjected to reaction with methyl chloroformate according to general procedure F to furnish 1-butyl-3-ethyl-9-fluoro-7-methoxy-1H-pyrimido[5,4-c]quinoline-2,4-dione (105 mg). LCMS: m/z 346 [M+1]$^+$.

Example 58

1-Butyl-9-chloro-3-ethyl-7-methoxy-1H-pyrimido[5,4-c]quinoline-2,4-dione

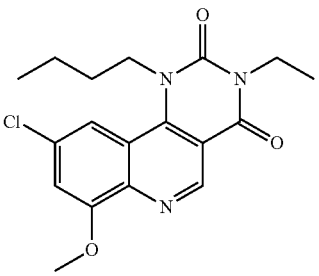 [SMILES: CCCCn1c(=O)n(CC)c(=O)c2cnc3c(OC)cc(Cl)cc3c21]

4,6-Dichloro-8-methoxy-quinoline-3-carboxylic acid ethyl ester (250 mg, 0.84 mmol) was treated with butylamine following general procedure B to afford 4-butylamino-6-chloro-8-methoxy-quinoline-3-carboxylic acid ethyl ester (230 mg). Thus obtained amino-ester was hydrolyzed to the corresponding acid using general procedure D and then transformed into the corresponding ethylamide (155 mg) following general procedure E. The above ethylamide (155 mg, 0.45 mmol) was subjected to reaction with methyl chloroformate according to general procedure F to furnish 1-butyl-9-chloro- 3-ethyl-7-methoxy-1H-pyrimido[5,4-c]quinoline-2,4-dione (87 mg). LCMS: m/z 362 [M+1]+.

Example 59

9-Chloro-3-ethyl-1-(4-fluoro-butyl)-7-methoxy-1H-pyrimido[5,4-c]quinoline-2,4-dione

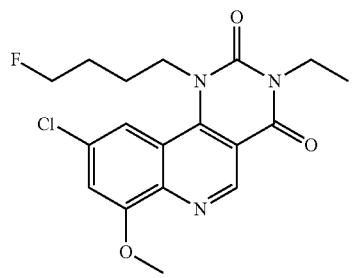 [SMILES: CCn1c(=O)c2cnc3c(OC)cc(Cl)cc3c2n(CCCCF)c1=O]

4,6-Dichloro-8-methoxy-quinoline-3-carboxylic acid ethyl ester (250 mg, 0.836 mmol) was treated with 4-fluorobutylamine following general procedure B to afford 6-Chloro-4-(4-fluoro-butylamino)-8-methoxy-quinoline-3-carboxylic acid ethyl ester (185 mg). Thus obtained aminoester was hydrolyzed to the corresponding acid using general procedure D and then transformed into the corresponding ethylamide (105 mg) following general procedure E. The above ethylamide (100 mg, 0.28 mmol) was subjected to reaction with methyl chloroformate according to general procedure F to furnish 9-chloro-3-ethyl-1-(4-fluoro-butyl)-7-methoxy-1H-pyrimido[5,4-c]quinoline-2,4-dione (54 mg). LCMS: m/z 380 [M+1]+.

Example 60

1-Butyl-8-chloro-3-ethyl-7-methoxy-1H-pyrimido[5,4-c]quinoline-2,4-dione

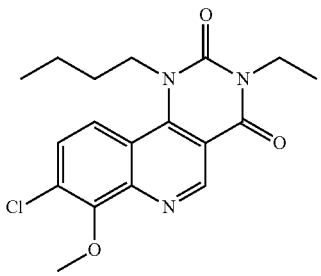 [SMILES: CCCCn1c(=O)n(CC)c(=O)c2cnc3c(OC)c(Cl)ccc3c21]

4,7-Dichloro-8-methoxy-quinoline-3-carboxylic acid ethyl ester (250 mg, 0.84 mmol) was treated with butylamine following general procedure B to afford 7-chloro-4-butylamino-8-methoxy-quinoline-3-carboxylic acid ethyl ester (210 mg). Thus obtained amino-ester was hydrolyzed to the corresponding acid using general procedure D and then transformed into the corresponding ethylamide (125 mg) following general procedure E. The above ethylamide (0.37 mmol) was subjected to reaction with methyl chloroformate according to general procedure F to furnish 8-chloro-3-ethyl-1-butyl-7-methoxy-1H-pyrimido[5,4-c]quinoline-2,4-dione (75 mg). LCMS: m/z 380 [M+1]+.

Example 61

3-Ethyl-9-fluoro-1-(4-fluoro-butyl)-7-methoxy-1H-pyrimido[5,4-c]quinoline-2,4-dione

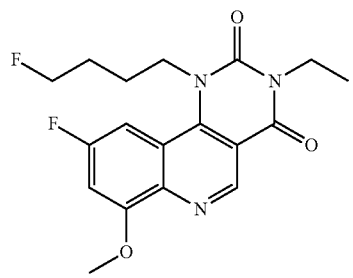 [SMILES: CCn1c(=O)c2cnc3c(OC)cc(F)cc3c2n(CCCCF)c1=O]

4-Chloro-6-fluoro-8-methoxy-quinoline-3-carboxylic acid ethyl ester (250 mg, 0.88 mmol) was treated with 4-fluoro-butylamine following general procedure B to afford 6-fluoro-4-(4-fluoro-butylamino)-8-methoxy-quinoline-3-carboxylic acid ethyl ester (175 mg). Thus obtained aminoester was hydrolyzed to the corresponding acid using general procedure D and then transformed into the corresponding ethylamide (95 mg) following general procedure E. The above ethylamide (95 mg, 0.28 mmol) was subjected to reaction with methyl chloroformate according to general procedure F to furnish 3-ethyl-9-fluoro-1-(4-fluoro-butyl)-7-methoxy-1H-pyrimido[5,4-c]quinoline-2,4-dione (52 mg). LCMS: m/z 364 [M+1]+.

Example 62

3-Ethyl-1-(4-fluoro-butyl)-7-methoxy-1H-pyrimido[5,4-c]quinoline-2,4-dione

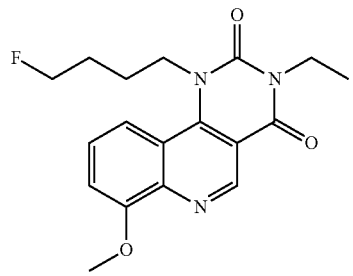 [SMILES: CCn1c(=O)c2cnc3c(OC)cccc3c2n(CCCCF)c1=O]

4-Chloro-8-methoxy-quinoline-3-carboxylic acid ethyl ester (250 mg, 0.94 mmol) was treated with 4-fluoro-butylamine following general procedure B to afford 4-(4-fluoro-butylamino)-8-methoxy-quinoline-3-carboxylic acid ethyl ester (244 mg). Thus obtained amino-ester was hydrolyzed to the corresponding acid using general procedure D and then transformed into the corresponding ethylamide (150 mg) following general procedure E. The above ethylamide (145 mg, 0.45 mmol) was subjected to reaction with methyl chloroformate according to general procedure F to furnish 3-ethyl-1-

(4-fluoro-butyl)-7-methoxy-1H-pyrimido[5,4-c]quinoline-2,4-dione (95 mg). LCMS: m/z 346 [M+1]+.

Example 63

1-Cyclopentyl-3-(4-fluoro-3-methyl-phenyl)-7-methoxy-1H-pyrimido[5,4-c]quinoline-2,4-dione

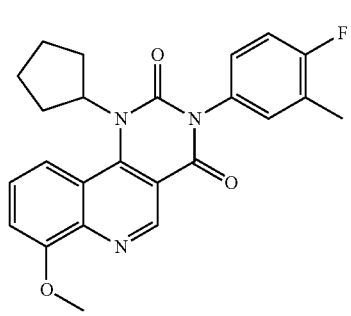 [SMILES: COc1cccc2c1ncc1c(=O)n(-c3ccc(F)c(C)c3)c(=O)n(C3CCCC3)c12]

1-Cyclopentyl-3-(4-fluoro-3-methyl-phenyl)-7-methoxy-1H-pyrimido[5,4-c]quinoline-2,4-dione (25 mg) was prepared from 4-cyclopentylamino-8-methoxy-quinoline-3-carboxylic acid ethyl ester (0.1 mmol) and 1-fluoro-4-isocyanato-2-methyl-benzene (0.5 mmol) following general procedure C. LCMS: m/z 420 [M+1]+.

Example 64

1-Cyclopentyl-3-(3-fluoro-4-methyl-phenyl)-7-methoxy-1H-pyrimido[5,4-c]quinoline-2,4-dione

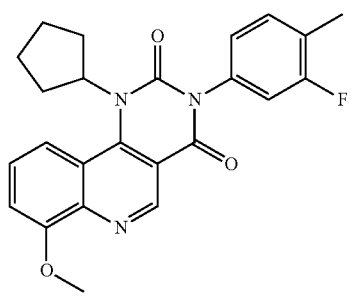 [SMILES: COc1cccc2c1ncc1c(=O)n(-c3ccc(C)c(F)c3)c(=O)n(C3CCCC3)c12]

1-Cyclopentyl-3-(3-fluoro-4-methyl-phenyl)-7-methoxy-1H-pyrimido[5,4-c]quinoline-2,4-dione (28 mg) was prepared from 4-cyclopentylamino-8-methoxy-quinoline-3-carboxylic acid ethyl ester (0.1 mmol) and 1-fluoro-5-isocyanato-2-methyl-benzene (0.5 mmol) following general procedure C. LCMS: m/z 420 [M+1]+.

Example 65

1-Cyclopentyl-7-methoxy-3-(3-methoxy-phenyl)-1H-pyrimido[5,4-c]quinoline-2,4-dione

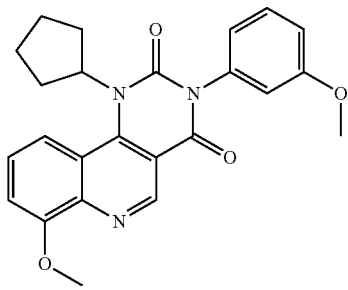 [SMILES: COc1cccc(-n2c(=O)c3cnc4c(OC)cccc4c3n(C3CCCC3)c2=O)c1]

1-Cyclopentyl-7-methoxy-3-(3-methoxy-phenyl)-1H-pyrimido[5,4-c]quinoline-2,4-dione (32 mg) was prepared from 4-cyclopentylamino-8-methoxy-quinoline-3-carboxylic acid ethyl ester (0.1 mmol) and 1-isocyanato-3-methoxy-benzene (0.5 mmol) following general procedure C. LCMS: m/z 418 [M+1]+. $^1$H NMR (400 MHz, CDCl$_3$): δ 9.50 (s, 1H), 7.86 (d, 1H), 7.64 (t, 1H), 7.44 (t, 1H), 7.30 (d, 1H), 6.82 (dd, 1H), 6.60 (d, 1H), 6.28 (s, 1H), 5.04 (p, 1H), 4.17 (s, 3H), 3.80 (s, 3H), 2.40 (m, 2H), 2.04-2.20 (m, 4H), 1.24 (m, 2H) ppm.

Example 66

1-Cyclopentyl-3-(3-fluoro-phenyl)-7-methoxy-1H-pyrimido[5,4-c]quinoline-2,4-dione

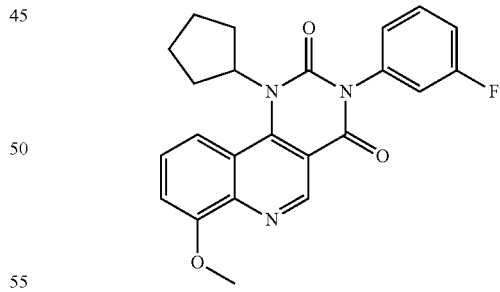

1-Cyclopentyl-3-(3-fluoro-phenyl)-7-methoxy-1H-pyrimido[5,4-c]quinoline-2,4-dione (23 mg) was prepared from 4-cyclopentylamino-8-methoxy-quinoline-3-carboxylic acid ethyl ester (0.1 mmol) and 1-fluoro-3-isocyanato-benzene (0.5 mmol) following general procedure C. LCMS: m/z 406 [M+1]+. $^1$H NMR (400 MHz, CDCl$_3$): δ 9.45 (s, 1H), 7.84 (d, 1H), 7.62 (d, 1H), 7.51 (t, 1H), 7.20 (m, 1H), 7.18 (m, 1H), 7.12 (m, 1H), 7.09 (s, 1H), 5.06 (p, 1H), 4.15 (s, 3H), 2.42 (m, 2H), 2.06-2.18 (m, 4H), 1.26 (m, 2H) ppm.

Example 67

1-Cyclopentyl-3-(4-difluoromethoxy-phenyl)-7-methoxy-1H-pyrimido[5,4-c]quinoline-2,4-dione

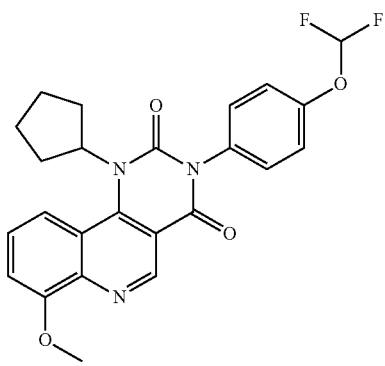 [SMILES: COc1cccc2c1ncc1c(=O)n(-c3ccc(OC(F)F)cc3)c(=O)n(C3CCCC3)c12]

1-Cyclopentyl-3-(4-difluoromethoxy-phenyl)-7-methoxy-1H-pyrimido[5,4-c]quinoline-2,4-dione (19 mg) was prepared from 4-cyclopentylamino-8-methoxy-quinoline-3-carboxylic acid ethyl ester (0.1 mmol) and 1-difluoromethoxy-4-isocyanato-benzene (0.5 mmol) following general procedure C. LCMS: m/z 454 [M+1]$^+$.

Example 68

1-Cyclopentyl-7-methoxy-3-(4-trifluoromethoxy-phenyl)-1H-pyrimido[5,4-c]quinoline-2,4-dione

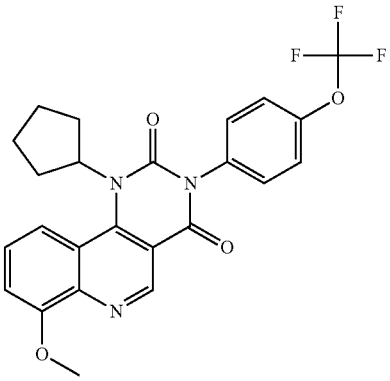 [SMILES: COc1cccc2c1ncc1c(=O)n(-c3ccc(OC(F)(F)F)cc3)c(=O)n(C3CCCC3)c12]

1-Cyclopentyl-7-methoxy-3-(4-trifluoromethoxy-phenyl)-1H-pyrimido[5,4-c]quinoline-2,4-dione (24 mg) was prepared from 4-cyclopentylamino-8-methoxy-quinoline-3-carboxylic acid ethyl ester (0.1 mmol) and 1-isocyanato-4-trifluoromethoxy-benzene (0.5 mmol) following general procedure C. LCMS: m/z 472 [M+1]$^+$.

Example 69

1-Cyclopentyl-7-methoxy-3-(2-trifluoromethyl-phenyl)-1H-pyrimido[5,4-c]quinoline-2,4-dione

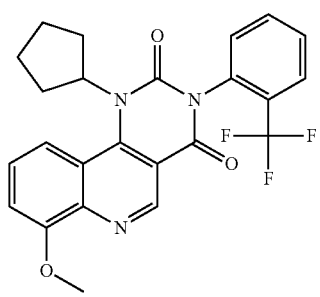 [SMILES: COc1cccc2c1ncc1c(=O)n(-c3ccccc3C(F)(F)F)c(=O)n(C3CCCC3)c12]

1-Cyclopentyl-7-methoxy-3-(2-trifluoromethyl-phenyl)-1H-pyrimido[5,4-c]quinoline-2,4-dione (21 mg) was prepared from 4-cyclopentylamino-8-methoxy-quinoline-3-carboxylic acid ethyl ester (0.1 mmol) and 1-isocyanato-2-trifluoromethyl-benzene (0.5 mmol) following general procedure C. LCMS: m/z 456 [M+1]$^+$.

Example 70

1-Cyclopentyl-7-methoxy-3-(5-methyl-2-trifluoromethyl-furan-3-yl)-1H-pyrimido[5,4-c]quinoline-2,4-dione 1-Cyclopentyl-7-methoxy-3-(5-methyl-2-trifluoromethyl-furan-3-yl)-1H-pyrimido[5,4-c]quinoline-2,4-dione (25 mg) was prepared from 4-cyclopentylamino-8-methoxy-quinoline-3-carboxylic acid ethyl ester (0.1 mmol) and 3-isocyanato-5-methyl-2-trifluoromethyl-furan (0.5 mmol) following general procedure C. LCMS: m/z 460 [M+1]⁺.

Example 71

1-Cyclopentyl-7-methoxy-3-(3-methyl-benzyl)-1H-pyrimido[5,4-c]quinoline-2,4-dione

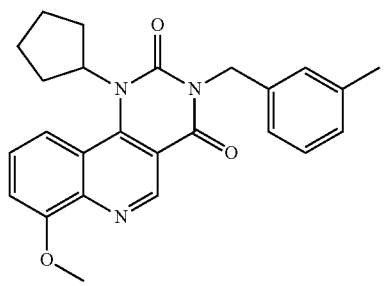 [SMILES: COc1cccc2c1ncc1c(=O)n(Cc3cccc(C)c3)c(=O)n(C3CCCC3)c12]

1-Cyclopentyl-7-methoxy-3-(3-methyl-benzyl)-1H-pyrimido[5,4-c]quinoline-2,4-dione (18 mg) was prepared from 4-cyclopentylamino-8-methoxy-quinoline-3-carboxylic acid ethyl ester (0.1 mmol) and 1-isocyanatomethyl-3-methyl-benzene (0.5 mmol) following general procedure C. LCMS: m/z 416 [M+1]⁺.

Example 72

3-(3-Chloro-phenyl)-7-methoxy-1-(4-methyl-cyclohexyl)-1H-pyrimido[5,4-c]quinoline-2,4-dione

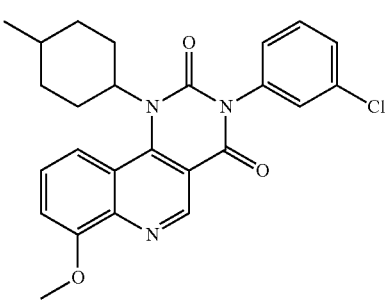 [SMILES: COc1cccc2c1ncc1c(=O)n(-c3cccc(Cl)c3)c(=O)n(C3CCC(C)CC3)c12]

3-(3-Chloro-phenyl)-7-methoxy-1-(4-methyl-cyclohexyl)-1H-pyrimido[5,4-c]quinoline-2,4-dione (115 mg) was prepared from 8-methoxy-4-(4-methyl-cyclohexylamino)-quinoline-3-carboxylic acid ethyl ester (150 mg, 0.44 mmol) and 1-chloro-3-isocyanato-benzene (0.66 mmol) following general procedure C. LCMS: m/z 450 [M+1]⁺.

Example 73

3-(3-Chloro-phenyl)-1-cyclopentyl-7-methoxy-1H-pyrimido[5,4-c]quinoline-2,4-dione

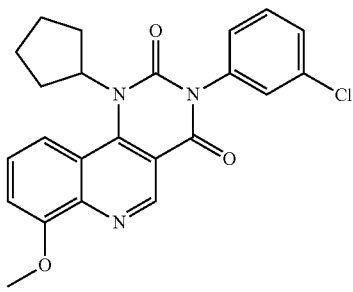 [SMILES: COc1cccc2c1ncc1c(=O)n(-c3cccc(Cl)c3)c(=O)n(C3CCCC3)c12]

3-(3-Chloro-phenyl)-1-cyclopentyl-7-methoxy-1H-pyrimido[5,4-c]quinoline-2,4-dione (55 mg) was prepared from 4-cyclopentylamino-8-methoxy-quinoline-3-carboxylic acid ethyl ester (0.48 mmol) and 1-chloro-3-isocyanato-benzene (0.72 mmol) following general procedure C. LCMS: m/z 422 [M+1]⁺.

Example 74

1-Cyclopentyl-3-(3,5-dimethyl-phenyl)-7-methoxy-1H-pyrimido[5,4-c]quinoline-2,4-dione

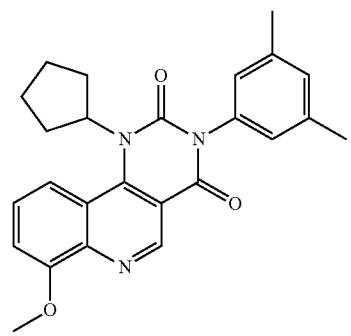 [SMILES: COc1cccc2c1ncc1c(=O)n(-c3cc(C)cc(C)c3)c(=O)n(C3CCCC3)c12]

1-Cyclopentyl-3-(3,5-dimethyl-phenyl)-7-methoxy-1H-pyrimido[5,4-c]quinoline-2,4-dione (33 mg) was prepared from 4-cyclopentylamino-8-methoxy-quinoline-3-carboxylic acid ethyl ester (0.32 mmol) and 1-isocyanato-3,5-dimethyl-benzene (0.48 mmol) following general procedure C. LCMS: m/z 416 [M+1]⁺.

Example 75

1-Cyclopentyl-3-(3-ethyl-phenyl)-7-methoxy-1H-pyrimido[5,4-c]quinoline-2,4-dione

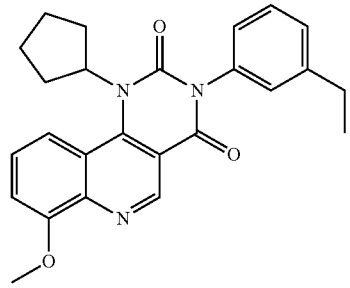 [SMILES: CCc1cccc(-n2c(=O)c3cnc4c(OC)cccc4c3n(C3CCCC3)c2=O)c1]

1-Cyclopentyl-3-(3-ethyl-phenyl)-7-methoxy-1H-pyrimido[5,4-c]quinoline-2,4-dione (89 mg) was prepared from 4-cyclopentylamino-8-methoxy-quinoline-3-carboxylic acid ethyl ester (0.32 mmol) and 1-ethyl-3-isocyanato-benzene (0.48 mmol) following general procedure C. LCMS: m/z 416 [M+1]⁺.

Example 76

1-Cyclopentyl-3-(2,3-dimethyl-phenyl)-7-methoxy-1H-pyrimido[5,4-c]quinoline-2,4-dione

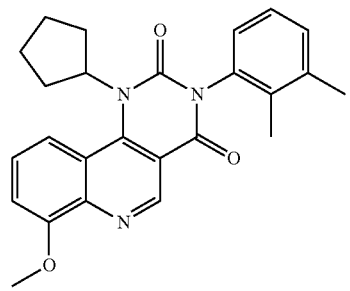 [SMILES: COc1cccc2c1ncc1c(=O)n(-c3cccc(C)c3C)c(=O)n(C3CCCC3)c12]

1-Cyclopentyl-3-(2,3-dimethyl-phenyl)-7-methoxy-1H-pyrimido[5,4-c]quinoline-2,4-dione (22 mg) was prepared from 4-cyclopentylamino-8-methoxy-quinoline-3-carboxy-lic acid ethyl ester (0.32 mmol) and 1-isocyanato-2,3-dimethyl-benzene (0.48 mmol) following general procedure C. LCMS: m/z 416 [M+1]⁺.

Example 77

1-Cyclopentyl-3-(2,5-dimethyl-phenyl)-7-methoxy-1H-pyrimido[5,4-c]quinoline-2,4-dione

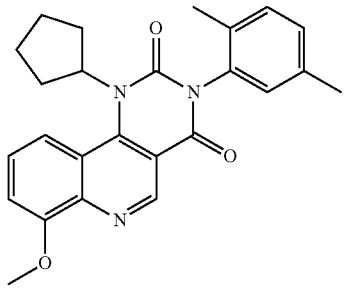 [SMILES: COc1cccc2c1ncc1c(=O)n(-c3cc(C)ccc3C)c(=O)n(C3CCCC3)c12]

1-Cyclopentyl-3-(2,5-dimethyl-phenyl)-7-methoxy-1H-pyrimido[5,4-c]quinoline-2,4-dione (46 mg) was prepared from 4-cyclopentylamino-8-methoxy-quinoline-3-carboxylic acid ethyl ester (0.32 mmol) and 1-isocyanato-2,5-dimethyl-benzene (0.48 mmol) following general procedure C. LCMS: m/z 416 [M+1]⁺.

Example 78

7-Methoxy-1-(4-methyl-cyclohexyl)-3-m-tolyl-1H-pyrimido[5,4-c]quinoline-2,4-dione

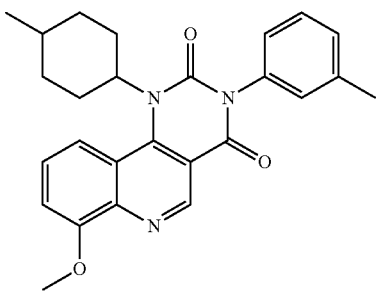

7-Methoxy-1-(4-methyl-cyclohexyl)-3-m-tolyl-1H-pyrimido[5,4-c]quinoline-2,4-dione (135 mg) was prepared from 8-methoxy-4-(4-methyl-cyclohexylamino)-quinoline- 3-carboxylic acid ethyl ester (0.29 mmol) and 1-isocyanato-3-methyl-benzene (0.44 mmol) following general procedure C. LCMS: m/z 430 [M+1]⁺.

Example 79

1-Cyclopentyl-7-methoxy-3-(3-nitro-phenyl)-1H-pyrimido[5,4-c]quinoline-2,4-dione

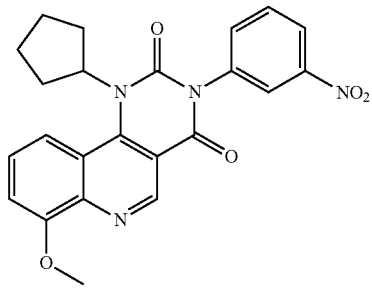 [SMILES: COc1cccc2c1ncc1c(=O)n(-c3cccc([N+](=O)[O-])c3)c(=O)n(C3CCCC3)c12]

1-Cyclopentyl-7-methoxy-3-(3-nitro-phenyl)-1H-pyrimido[5,4-c]quinoline-2,4-dione (19 mg) was prepared from 4-cyclopentylamino-8-methoxy-quinoline-3-carboxylic acid ethyl ester (0.1 mmol) and 1-isocyanato-3-nitro-benzene (0.5 mmol) following general procedure C. LCMS: m/z 433 [M+1]⁺.

Example 80

1-Cyclopentyl-7-methoxy-3-(3-trifluoromethyl-phenyl)-1H-pyrimido[5,4-c]quinoline-2,4-dione

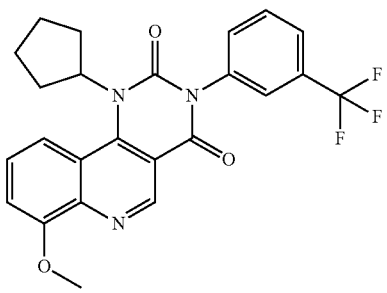 [SMILES: COc1cccc2c1ncc1c(=O)n(-c3cccc(C(F)(F)F)c3)c(=O)n(C3CCCC3)c12]

1-Cyclopentyl-7-methoxy-3-(3-trifluoromethyl-phenyl)-1H-pyrimido[5,4-c]quinoline-2,4-dione (27 mg) was prepared from 4-cyclopentylamino-8-methoxy-quinoline-3-carboxylic acid ethyl ester (0.1 mmol) and 1-isocyanato-3-nitro-benzene (0.5 mmol) following general procedure C. LCMS: m/z 456 [M+1]⁺.

Example 81

1-Cyclopentyl-3-(3,4-dimethyl-phenyl)-7-methoxy-1H-pyrimido[5,4-c]quinoline-2,4-dione

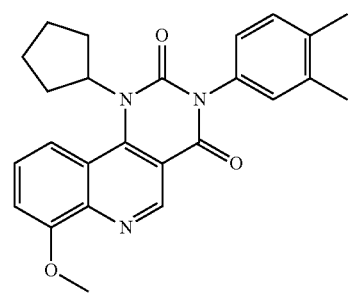 [SMILES: COc1cccc2c1ncc1c(=O)n(-c3ccc(C)c(C)c3)c(=O)n(C3CCCC3)c12]

1-Cyclopentyl-3-(3,4-dimethyl-phenyl)-7-methoxy-1H-pyrimido[5,4-c]quinoline-2,4-dione (106 mg) was prepared from 4-cyclopentylamino-8-methoxy-quinoline-3-carboxylic acid ethyl ester (0.32 mmol) and 1-isocyanato-3,4-dimethyl-benzene (0.48 mmol) following general procedure C. LCMS: m/z 416 [M+1]⁺.

Example 82

1-Cyclopentyl-7-methoxy-3-o-tolyl-1H-pyrimido[5,4-c]quinoline-2,4-dione

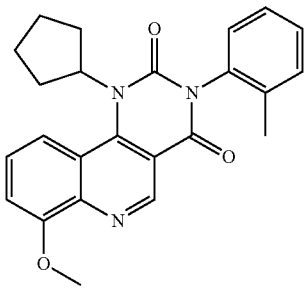 [SMILES: COc1cccc2c1ncc1c(=O)n(-c3ccccc3C)c(=O)n(C3CCCC3)c12]

1-Cyclopentyl-7-methoxy-3-o-tolyl-1H-pyrimido[5,4-c]quinoline-2,4-dione (24 mg) was prepared from 4-cyclopentylamino-8-methoxy-quinoline-3-carboxylic acid ethyl ester (0.1 mmol) and 1-isocyanato-2-methyl-benzene (0.5 mmol) following general procedure C. LCMS: m/z 402 [M+1]+.

Example 83

1-Butyl-7-methoxy-3-m-tolyl-1H-pyrimido[5,4-c]quinoline-2,4-dione

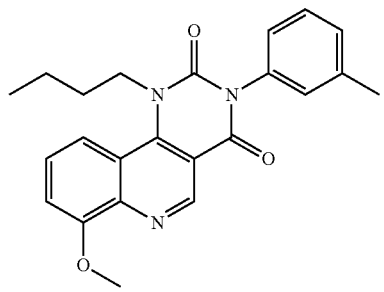 [SMILES: CCCCn1c(=O)n(-c2cccc(C)c2)c(=O)c2cnc3c(OC)cccc3c21]

1-Butyl-7-methoxy-3-m-tolyl-1H-pyrimido[5,4-c]quinoline-2,4-dione (17 mg) was prepared from 4-butylamino-8-methoxy-quinoline-3-carboxylic acid ethyl ester (0.1 mmol) and 1-isocyanato-3-methyl-benzene (0.5 mmol) following general procedure C. LCMS: m/z 390 [M+1]+.

Example 84

3-Benzo[1,3]dioxol-5-yl-1-cyclopentyl-7-methoxy-1H-pyrimido[5,4-c]quinoline-2,4-dione

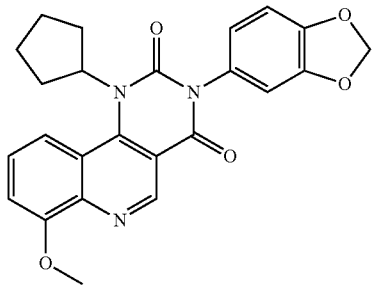 [SMILES: COc1cccc2c1ncc1c(=O)n(-c3ccc4c(c3)OCO4)c(=O)n(C3CCCC3)c12]

3-Benzo[1,3]dioxol-5-yl-1-cyclopentyl-7-methoxy-1H-pyrimido[5,4-c]quinoline-2,4-dione (33 mg) was prepared from 4-cyclopentylamino-8-methoxy-quinoline-3-carboxylic acid ethyl ester (0.1 mmol) and 5-isocyanato-benzo[1,3]dioxole (0.5 mmol) following general procedure C. LCMS: m/z 432 [M+1]+.

Example 85

1-Cyclopentyl-3-indan-5-yl-7-methoxy-1H-pyrimido[5,4-c]quinoline-2,4-dione

1-Cyclopentyl-3-indan-5-yl-7-methoxy-1H-pyrimido[5,4-c]quinoline-2,4-dione (21 mg) was prepared from 4-cyclopentylamino-8-methoxy-quinoline-3-carboxylic acid ethyl ester (0.1 mmol) and 5-isocyanato-indan (0.5 mmol) following general procedure C. LCMS: m/z 428 [M+1]+.

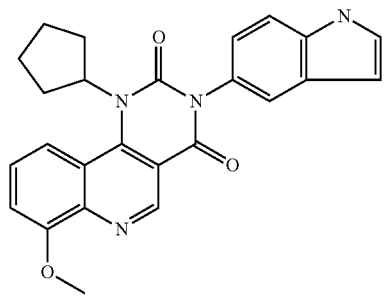 [SMILES: COc1cccc2c1ncc1c(=O)n(-c3ccc4[nH]ccc4c3)c(=O)n(C3CCCC3)c12]

Example 86

1-Cyclopentyl-7-methoxy-3-phenethyl-1H-pyrimido[5,4-c]quinoline-2,4-dione

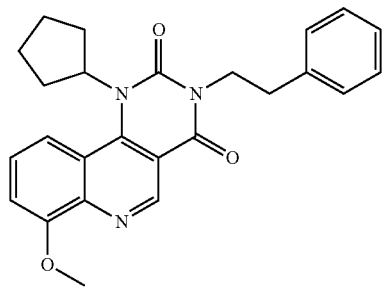 [SMILES: COc1cccc2c1ncc1c(=O)n(CCc3ccccc3)c(=O)n(C3CCCC3)c12]

1-Cyclopentyl-7-methoxy-3-phenethyl-1H-pyrimido[5,4-c]quinoline-2,4-dione (20 mg) was prepared from 4-cyclopentylamino-8-methoxy-quinoline-3-carboxylic acid ethyl ester (0.1 mmol) and (2-phenyl)ethyl isocyanate (0.5 mmol) following general procedure C. LCMS: m/z 416 [M+1]+.

Example 87

3-(3-Chloro-phenyl)-1-(4,4-difluoro-cyclohexyl)-7-methoxy-1H-pyrimido[5,4-c]quinoline-2,4-dione

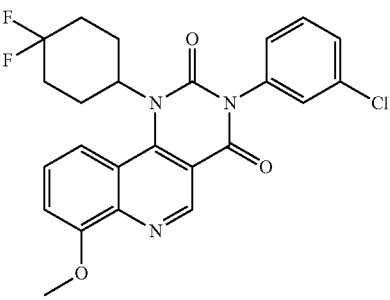 [SMILES: COc1cccc2c1ncc1c(=O)n(-c3cccc(Cl)c3)c(=O)n(C3CCC(F)(F)CC3)c12]

4-Chloro-8-methoxy-quinoline-3-carboxylic acid ethyl ester (250 mg, 0.94 mmol) was treated with 4,4-difluoro-cyclohexylamine following general procedure B to afford 4-(4,4-difluoro-cyclohexylamino)-8-methoxy-quinoline-3-carboxylic acid ethyl ester (192 mg). Thus obtained amino-ester (92 mg, 0.25 mmol) was subjected to reaction with 1-chloro-3-isocyanato-benzene according to general procedure C to furnish 3-(3-chloro-phenyl)-1-(4,4-difluoro-cyclohexyl)-7-methoxy-1H-pyrimido[5,4-c]quinoline-2,4-dione (69 mg). LCMS: m/z 472 [M+1]⁺. ¹H NMR (400 MHz, CDCl₃): δ 9.56 (s, 1H), 7.58 (m, 1H), 7.48 (m, 1H), 7.38 (m, 1H), 7.24 (m, 1H), 7.06-7.14 (m, 2H), 6.48 (m, 1H), 5.09 (m, 1H), 4.08 (s, 3H), 2.84 (m, 2H), 2.23 (m, 2H), 1.80-2.00 (m, 4H) ppm.

Example 88

4-[3-(3-Chloro-phenyl)-7-methoxy-2,4-dioxo-3,4-dihydro-2H-pyrimido[5,4-c]quinolin-1-yl]-piperidine-1-carboxylic acid tert-butyl ester

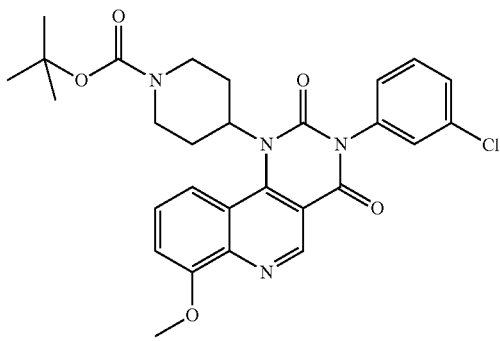 [SMILES: COc1cccc2c1ncc1c(=O)n(-c3cccc(Cl)c3)c(=O)n(C3CCN(C(=O)OC(C)(C)C)CC3)c12]

4-Chloro-8-methoxy-quinoline-3-carboxylic acid ethyl ester (1.0 g, 3.77 mmol) was treated with 4-amino-piperidine-1-carboxylic acid tert-butyl ester following general procedure B to afford 4-(1-tert-butoxycarbonyl-piperidin-4-ylamino)-8-methoxy-quinoline-3-carboxylic acid ethyl ester (1.48 g). Thus obtained amino-ester (500 mg, 1.17 mmol) was subjected to reaction with 1-chloro-3-isocyanato-benzene according to general procedure C to furnish 4-[3-(3-chloro-phenyl)-7-methoxy-2,4-dioxo-3,4-dihydro-2H-pyrimido[5,4-c]quinolin-1-yl]-piperidine-1-carboxylic acid tert-butyl ester (500 mg). LCMS: m/z 537 [M+1]⁺.

Example 89

3-(3-Chloro-phenyl)-7-methoxy-1-piperidin-4-yl-1H-pyrimido[5,4-c]quinoline-2,4-dione.dihydrochlode

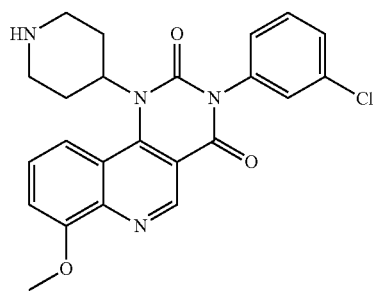 [SMILES: COc1cccc2c1ncc1c(=O)n(-c3cccc(Cl)c3)c(=O)n(C3CCNCC3)c12]

3-(3-Chloro-phenyl)-7-methoxy-1-piperidin-4-yl-1H-pyrimido[5,4-c]quinoline-2,4-dione.dihydrochloride (415 mg) was prepared according to general procedure G from 4-[3-(3-chloro-phenyl)-7-methoxy-2,4-dioxo-3,4-dihydro-2H-pyrimido[5,4-c]quinolin-1-yl]-piperidine-1-carboxylic acid tert-butyl ester (475 mg, 0.89 mmol). LCMS: m/z 437 [M+1]⁺.

Example 90

1-(1-Acetyl-piperidin-4-yl)-3-(3-chloro-phenyl)-7-methoxy-1H-pyrimido[5,4-c]quinoline-2,4-dione

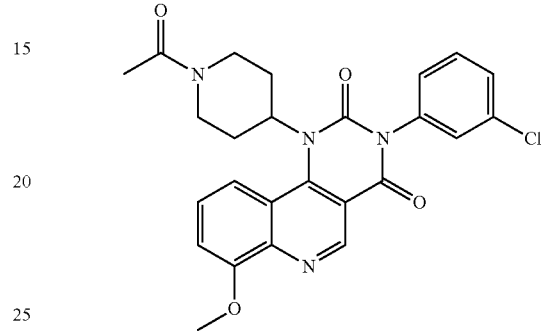

1-(1-Acetyl-piperidin-4-yl)-3-(3-chloro-phenyl)-7-methoxy-1H-pyrimido[5,4-c]quinoline-2,4-dione (45 mg) was prepared according to general procedure H from 3-(3-chloro-phenyl)-7-methoxy-1-piperidin-4-yl-1H-pyrimido[5,4-c]quinoline-2,4-dione.dihydrochloride (50 mg, 0.1 mmol) and acetyl chloride. LCMS: m/z 479 [M+1]⁺. ¹H NMR (400 MHz, CDCl₃): δ 9.59 (s, 1H), 7.58 (m, 1H), 7.52 (m, 1H), 7.42 (m, 1H), 7.24 (m, 1H), 7.10-7.18 (m, 2H), 6.48 (m, 1H), 5.18 (m, 1H), 4.82 (m, 1H), 4.12 (s, 3H), 3.95 (m, 1H), 3.20 (m, 1H), 3.58-3.78 (m, 3H), 2.08 (s, 3H), 1.78 (m, 2H) ppm.

Example 91

1-(1-Benzoyl-piperidin-4-yl)-3-(3-chloro-phenyl)-7-methoxy-1H-pyrimido[5,4-c]quinoline-2,4-dione

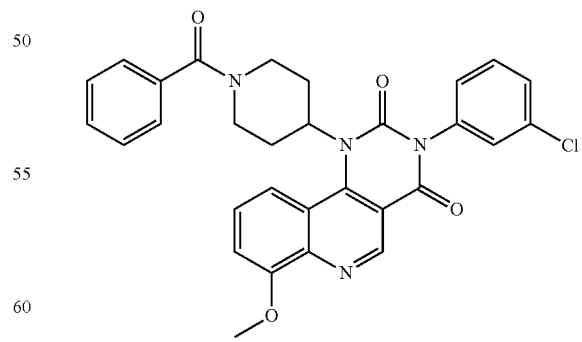

1-(1-Benzoyl-piperidin-4-yl)-3-(3-chloro-phenyl)-7-methoxy-1H-pyrimido[5,4-c]quinoline-2,4-dione (51 mg) was prepared according to general procedure H from 3-(3-chloro-phenyl)-7-methoxy-1-piperidin-4-yl-1H-pyrimido[5, 4-c]quinoline-2,4-dione.dihydrochloride (50 mg, 0.1 mmol) and benzoyl chloride. LCMS: m/z 541 [M+1]⁺.

Example 92

3-(3-Chloro-phenyl)-1-(1-methanesulfonyl-piperidin-4-yl)-7-methoxy-1H-pyrimido[5,4-c]quinoline-2,4-dione

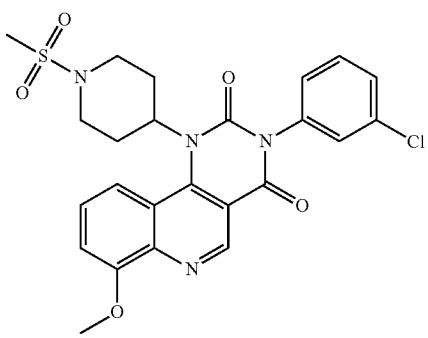 [SMILES: COc1cccc2c1ncc1c(=O)n(-c3cccc(Cl)c3)c(=O)n(C3CCN(S(C)(=O)=O)CC3)c12]

3-(3-Chloro-phenyl)-1-(1-methanesulfonyl-piperidin-4-yl)-7-methoxy-1H-pyrimido[5,4-c]quinoline-2,4-dione (47 mg) was prepared according to general procedure H from 3-(3-chloro-phenyl)-7-methoxy-1-piperidin-4-yl-1H-pyrimido[5,4-c]quinoline-2,4-dione.dihydrochloride (50 mg, 0.1 mmol) and methanesulfonyl chloride. LCMS: m/z 515 [M+1]⁺. ¹H NMR (400 MHz, CDCl₃): δ 9.56 (s, 1H), 7.58 (m, 1H), 7.48 (m, 1H), 7.38 (m, 1H), 7.24 (m, 1H), 7.09-7.18 (m, 2H), 6.48 (m, 1H), 5.06 (m, 1H), 4.10 (s, 3H), 4.02 (m, 2H), 3.80-3.92 (m, 7H), 1.84 (m, 2H) ppm.

Example 93

3-(3-Chloro-phenyl)-7-methoxy-1-[1-(propane-2-sulfonyl)-piperidin-4-yl]-1H-pyrimido[5,4-c]quinoline-2,4-dione

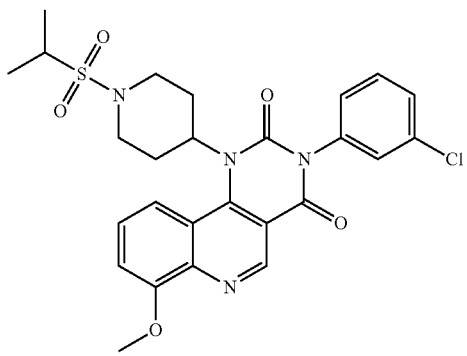

3-(3-Chloro-phenyl)-7-methoxy-1-[1-(propane-2-sulfonyl)-piperidin-4-yl]-1H-pyrimido[5,4-c]quinoline-2,4-dione (51 mg) was prepared according to general procedure H from 3-(3-chloro-phenyl)-7-methoxy-1-piperidin-4-yl-1H-pyrimido[5,4-c]quinoline-2,4-dione.dihydrochloride (50 mg, 0.1 mmol) and methanesulfonyl chloride. LCMS: m/z 543 [M+1]⁺.

Example 94

4-[3-(3-Chloro-phenyl)-7-methoxy-2,4-dioxo-3,4-dihydro-2H-pyrimido[5,4-c]quinolin-1-yl]-piperidine-1-sulfonic acid dimethylamide

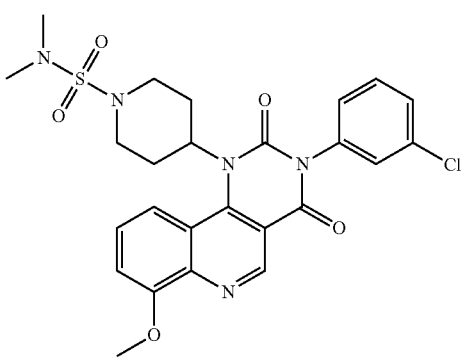 [SMILES: COc1cccc2c1ncc1c(=O)n(-c3cccc(Cl)c3)c(=O)n(C3CCN(S(=O)(=O)N(C)C)CC3)c12]

4-[3-(3-Chloro-phenyl)-7-methoxy-2,4-dioxo-3,4-dihydro-2H-pyrimido[5,4-c]quinolin-1-yl]-piperidine-1-sulfonic acid dimethylamide (48 mg) was prepared according to general procedure H from 3-(3-chloro-phenyl)-7-methoxy-1-piperidin-4-yl-1H-pyrimido[5,4-c]quinoline-2,4-dione.dihydrochloride (50 mg, 0.1 mmol) and N,N-dimethylsulfamoyl chloride. LCMS: m/z 544 [M+1]⁺.

Example 95

1-(1-Benzenesulfonyl-piperidin-4-yl)-3-(3-chloro-phenyl)-7-methoxy-1H-pyrimido[5,4-c]quinoline-2,4-dione

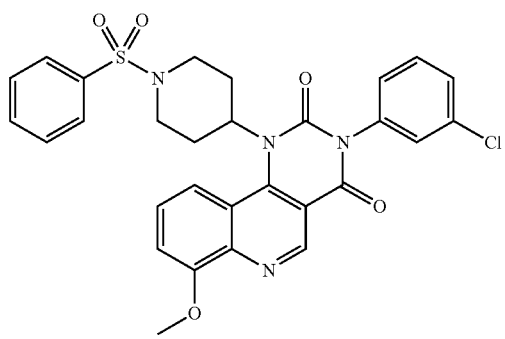 [SMILES: COc1cccc2c1ncc1c(=O)n(-c3cccc(Cl)c3)c(=O)n(C3CCN(S(=O)(=O)c4ccccc4)CC3)c12]

1-(1-Benzenesulfonyl-piperidin-4-yl)-3-(3-chloro-phenyl)-7-methoxy-1H-pyrimido[5,4-c]quinoline-2,4-dione (51 mg) was prepared according to general procedure H from 3-(3-chloro-phenyl)-7-methoxy-1-piperidin-4-yl-1H-pyrimido[5,4-c]quinoline-2,4-dione.dihydrochloride (50 mg, 0.1 mmol) and benzenesulfonyl chloride. LCMS: m/z 577 [M+1]+.

Example 96

3-(3-Chloro-phenyl)-1-[1-(1,1-dioxo-tetrahydro-1lambda*6*-thiophene-3-sulfonyl)-piperidin-4-yl]-7-methoxy-1H-pyrimido[5,4-c]quinoline-2,4-dione

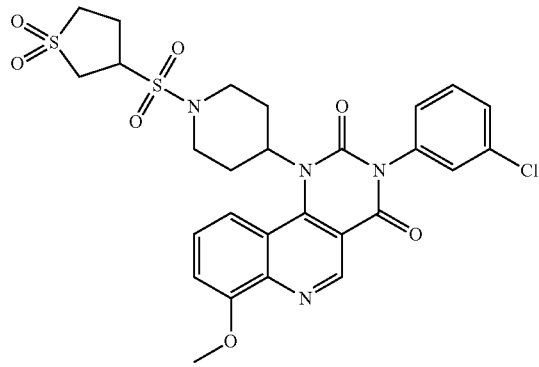 [SMILES: COc1cccc2c1ncc1c(=O)n(-c3cccc(Cl)c3)c(=O)n(C3CCN(S(=O)(=O)C4CCS(=O)(=O)C4)CC3)c12]

3-(3-Chloro-phenyl)-1-[1-(1,1-dioxo-tetrahydro-thiophene-3-sulfonyl)-piperidin-4-yl]-7-methoxy-1H-pyrimido[5,4-c]quinoline-2,4-dione (51 mg) was prepared according to general procedure H from 3-(3-chloro-phenyl)-7-methoxy-1-piperidin-4-yl-1H-pyrimido[5,4-c]quinoline-2,4-dione.dihydrochloride (50 mg, 0.1 mmol) and 1,1-dioxo-tetrahydro-thiophene-3-sulfonyl chloride. LCMS: m/z 619 [M+1]+.

Example 97

4-[3-(3-Chloro-phenyl)-7-methoxy-2,4-dioxo-3,4-dihydro-2H-pyrimido[5,4-c]quinolin-1-yl]-piperidine-1-carboxylic acid ethylamide

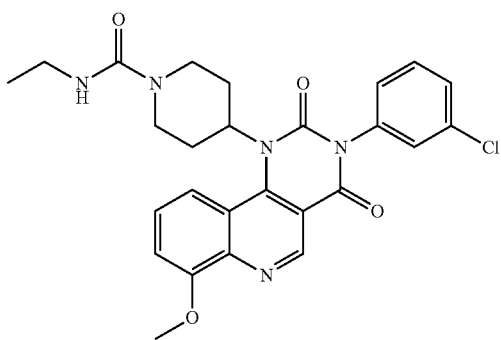 [SMILES: CCNC(=O)N1CCC(n2c(=O)n(-c3cccc(Cl)c3)c(=O)c3cnc4c(OC)cccc4c32)CC1]

4-[3-(3-Chloro-phenyl)-7-methoxy-2,4-dioxo-3,4-dihydro-2H-pyrimido[5,4-c]quinolin-1-yl]-piperidine-1-carboxylic acid ethylamide (40 mg) was prepared according to general procedure H from 3-(3-chloro-phenyl)-7-methoxy-1- piperidin-4-yl-1H-pyrimido[5,4-c]quinoline-2,4-dione.dihydrochloride (50 mg, 0.1 mmol) and ethyl isocyanate. LCMS: m/z 508 [M+1]+.

Example 98

4-[3-(3-Chloro-phenyl)-7-methoxy-2,4-dioxo-3,4-dihydro-2H-pyrimido[5,4-c]quinolin-1-yl]-piperidine-1-carboxylic acid isopropylamide

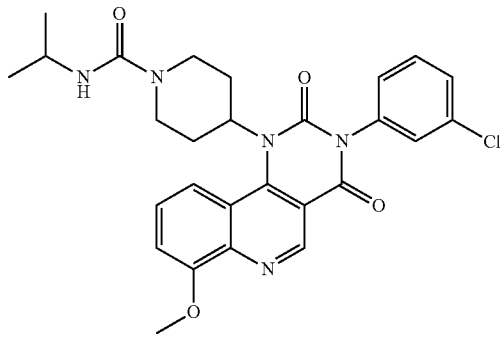 [SMILES: COc1cccc2c1ncc1c(=O)n(-c3cccc(Cl)c3)c(=O)n(C3CCN(C(=O)NC(C)C)CC3)c12]

4-[3-(3-Chloro-phenyl)-7-methoxy-2,4-dioxo-3,4-dihydro-2H-pyrimido[5,4-c]quinolin-1-yl]-piperidine-1-carboxylic acid isopropylamide (39 mg) was prepared according to general procedure H from 3-(3-chloro-phenyl)-7-methoxy-1-piperidin-4-yl-1H-pyrimido[5,4-c]quinoline-2,4-dione.dihydrochloride (50 mg, 0.10 mmol) and isopropyl isocyanate. LCMS: m/z 508 [M+1]+.

Example 99

3-(2-Chloro-phenyl)-7-methoxy-1-(4-methyl-cyclohexyl)-1H-pyrimido[5,4-c]quinoline-2,4-dione

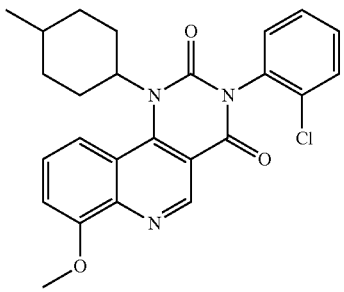 [SMILES: COc1cccc2c1ncc1c(=O)n(-c3ccccc3Cl)c(=O)n(C3CCC(C)CC3)c12]

3-(2-Chloro-phenyl)-7-methoxy-1-(4-methyl-cyclohexyl)-1H-pyrimido[5,4-c]quinoline-2,4-dione (50 mg) was prepared from 8-methoxy-4-(4-methyl-cyclohexylamino)-quinoline-3-carboxylic acid ethyl ester (0.164 mmol) and 1-chloro-2-isocyanato-benzene (0.25 mmol) following general procedure C. LCMS: m/z 450 [M+1]+. 1H NMR (400 MHz, CDCl3): δ 9.58 (s, 1H), 7.62 (m, 1H), 7.54-7.59 (m, 1H), 7.52 (m, 2H), 7.06 (m, 2H), 6.42 (m, 1H), 4.91 (m, 1H), 4.06 (s, 3H), 2.71 (m, 1H), 1.98 (m, 1H), 1.65 (m, 4H), 1.56 (m, 1H), 1.08 (d, 3H) ppm.

Example 100

3-(4-Chloro-phenyl)-7-methoxy-1-(4-methyl-cyclohexyl)-1H-pyrimido[5,4-c]quinoline-2,4-dione

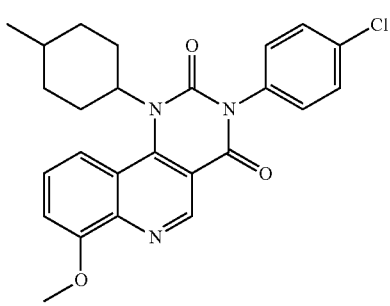 [SMILES: COc1cccc2c1ncc1c(=O)n(-c3ccc(Cl)cc3)c(=O)n(C3CCC(C)CC3)c12]

3-(4-Chloro-phenyl)-7-methoxy-1-(4-methyl-cyclohexyl)-1H-pyrimido[5,4-c]quinoline-2,4-dione (55 mg) was prepared from 8-methoxy-4-(4-methyl-cyclohexylamino)-quinoline-3-carboxylic acid ethyl ester (0.164 mmol) and 1-chloro-4-isocyanato-benzene (0.25 mmol) following general procedure C. LCMS: m/z 450 [M+1]$^+$.

Example 101

4-[3-(3-Chloro-phenyl)-7-methoxy-2,4-dioxo-3,4-dihydro-2H-pyrimido[5,4-c]quinolin-1-yl]-piperidine-1-carboxylic acid isopropyl ester

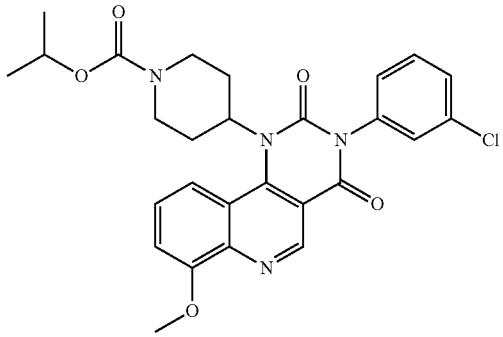 [SMILES: COc1cccc2c1ncc1c(=O)n(-c3cccc(Cl)c3)c(=O)n(C3CCN(C(=O)OC(C)C)CC3)c12]

4-[3-(3-Chloro-phenyl)-7-methoxy-2,4-dioxo-3,4-dihydro-2H-pyrimido[5,4-c]quinolin-1-yl]-piperidine-1-carboxylic acid isopropyl ester (47 mg) was prepared according to general procedure H from 3-(3-chloro-phenyl)-7-methoxy-1-piperidin-4-yl-1H-pyrimido[5,4-c]quinoline-2,4-dione.dihydrochloride (50 mg, 0.105 mmol) and isopropyl chloroformate. LCMS: m/z 523 [M+1]$^+$.

Example 102

Trans-4-[3-(3-Chloro-phenyl)-7-methoxy-2,4-dioxo-3,4-dihydro-2H-pyrimido[5,4-c]quinolin-1-yl]-cyclohexane-carboxylic acid methyl ester

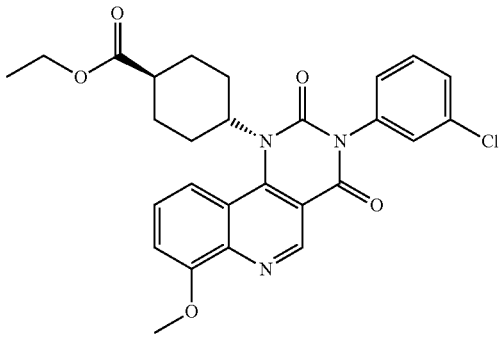

4-Chloro-8-methoxy-quinoline-3-carboxylic acid ethyl ester (250 mg, 0.94 mmol) was treated with trans-4-aminocyclohexanecarboxylic acid ethylester following general procedure B to afford 8-methoxy-4-(trans-4-ethoxycarbonyl-cyclohexylamino)-quinoline-3-carboxylic acid ethyl ester (207 mg). Thus obtained amino-ester (200 mg, 0.50 mmol) was subjected to reaction with 1-chloro-3-isocyanato-benzene according to general procedure C to furnish trans-4-[3-(3-chloro-phenyl)-7-methoxy-2,4-dioxo-3,4-dihydro-2H-pyrimido[5,4-c]quinolin-1-yl]-cyclohexane-carboxylic acid ethyl ester (175 mg). LCMS: m/z 508 [M+1]$^+$.

Example 103

Trans-4-[3-(3-Chloro-phenyl)-7-methoxy-2,4-dioxo-3,4-dihydro-2H-pyrimido[5,4-c]quinolin-1-yl]-cyclohexanecarboxylic acid.hydrochloride

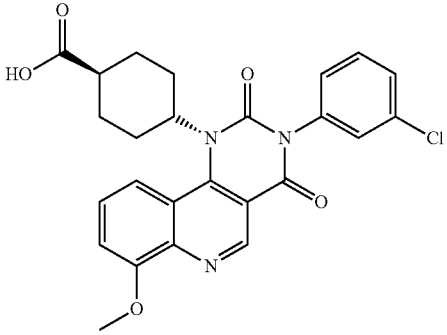

Trans-4-[3-(3-chloro-phenyl)-7-methoxy-2,4-dioxo-3,4-dihydro-2H-pyrimido[5,4-c]quinolin-1-yl]-cyclohexanecarboxylic acid.hydrochloride (31 mg) was prepared according to general procedure I from trans-4-[3-(3-chloro-phenyl)-7-methoxy-2,4-dioxo-3,4-dihydro-2H-pyrimido[5,4-c]quinolin-1-yl]-cyclohexane-carboxylic acid ethyl ester (75 mg, 0.15 mmol). LCMS: m/z 480 [M+1]+.

Example 104

Cis-4-[3-(3-Chloro-phenyl)-7-methoxy-2,4-dioxo-3,4-dihydro-2H-pyrimido[5,4-c]quinolin-1-yl]-cyclohexane-carboxylic acid ethyl ester

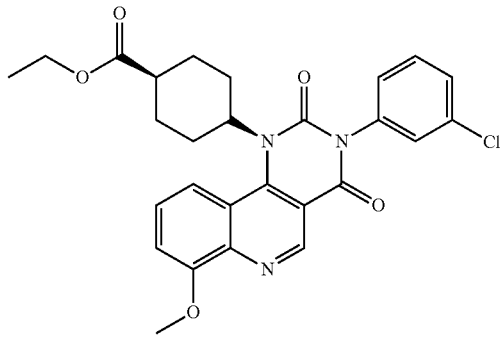

4-Chloro-8-methoxy-quinoline-3-carboxylic acid ethyl ester (250 mg, 0.94 mmol) was treated with cis-4-aminocyclohexanecarboxylic acid ethyl ester following general procedure B to afford 8-methoxy-4-(cis-4-ethoxycarbonyl-cyclohexylamino)-quinoline-3-carboxylic acid ethyl ester (198 mg). Thus obtained amino-ester (175 mg, 0.44 mmol) was subjected to reaction with 1-chloro-3-isocyanato-benzene according to general procedure C to furnish cis-4-[3-(3-chloro-phenyl)-7-methoxy-2,4-dioxo-3,4-dihydro-2H-pyrimido[5,4-c]quinolin-1-yl]-cyclohexane-carboxylic acid ethyl ester (138 mg). LCMS: m/z 508[M+1]+.

Example 105

Cis-4-[3-(3-Chloro-phenyl)-7-methoxy-2,4-dioxo-3,4-dihydro-2H-pyrimido[5,4-c]quinolin-1-yl]-cyclohexane-carboxylic acid.hydrochloride

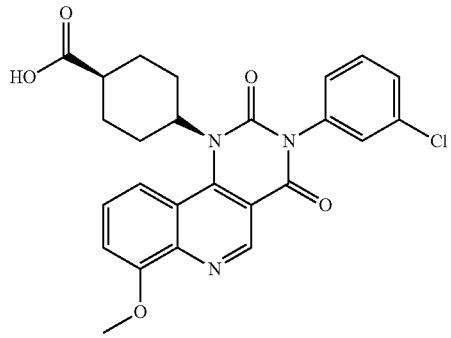

Cis-4-[3-(3-Chloro-phenyl)-7-methoxy-2,4-dioxo-3,4-dihydro-2H-pyrimido[5,4-c]quinolin-1-yl]-cyclohexanecarboxylic acid.hydrochloride (35 mg) was prepared according to general procedure I from cis-4-[3-(3-chloro-phenyl)-7-methoxy-2,4-dioxo-3,4-dihydro-2H-pyrimido[5,4-c]quinolin-1-yl]-cyclohexane-carboxylic acid ethyl ester (75 mg, 0.15 mmol). LCMS: m/z 480 [M+1]+.

Example 106

3-(3-Chloro-phenyl)-1-cyclohexyl-7-methoxy-1H-pyrimido[5,4-c]quinoline-2,4-dione

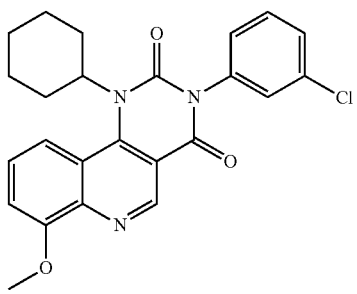 [SMILES: COc1cccc2c1ncc1c(=O)n(-c3cccc(Cl)c3)c(=O)n(C3CCCCC3)c12]

3-(3-Chloro-phenyl)-1-cyclohexyl-7-methoxy-1H-pyrimido[5,4-c]quinoline-2,4-dione (30 mg) was prepared from 4-cyclohexylamino-8-methoxy-quinoline-3-carboxylic acid ethyl ester (0.1 mmol) and 1-chloro-3-isocyanato-benzene (0.15 mmol) following general procedure C. LCMS: m/z 436 [M−1]+.

Example 107

4-(3-Benzo[1,3]-dioxol-5-yl-7-methoxy-2,4-dioxo-3,4-dihydro-2H-pyrimido[5,4-c]quinolin-1-yl)-piperidine-1-carboxylic acid tert-butyl ester

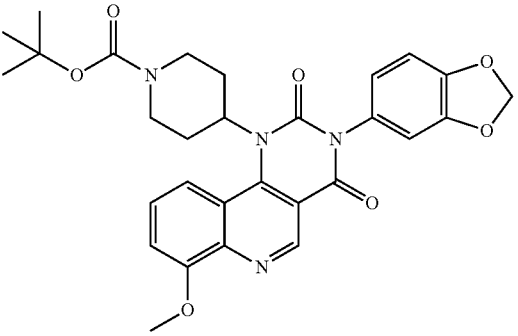 [SMILES: COc1cccc2c1ncc1c(=O)n(-c3ccc4c(c3)OCO4)c(=O)n(C3CCN(C(=O)OC(C)(C)C)CC3)c12]

4-(3-Benzo[1,3]dioxol-5-yl-7-methoxy-2,4-dioxo-3,4-dihydro-2H-pyrimido[5,4-c]quinolin-1-yl)-piperidine-1-carboxylic acid tert-butyl ester (110 mg) was prepared from 4-(1-tert-butoxycarbonyl-piperidin-4-ylamino)-8-methoxy-quinoline-3-carboxylic acid ethyl ester (0.31 mmol) and 5-isocyanato-benzo[1,3]dioxole (0.465 mmol) following general procedure C. LCMS: m/z 547 [M+1]+.

Example 108

3-Benzo[1,3]dioxol-5-yl-7-methoxy-1-piperidin-4-yl-1H-pyrimido[5,4-c]quinoline-2,4-dione.dihydrochloride

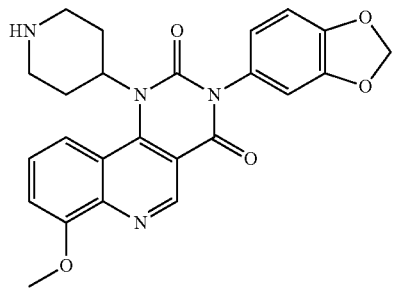 [SMILES: COc1cccc2c1ncc1c(=O)n(-c3ccc4c(c3)OCO4)c(=O)n(C3CCNCC3)c12]

3-Benzo[1,3]dioxol-5-yl-7-methoxy-1-piperidin-4-yl-1H-pyrimido[5,4-c]quinoline-2,4-dione.dihydrochloride (88 mg) was prepared according to general procedure G from 4-(3-benzo[1,3]dioxol-5-yl-7-methoxy-2,4-dioxo-3,4-dihydro-2H-pyrimido[5,4-c]quinolin-1-yl)-piperidine-1-carboxylic acid tert-butyl ester (100 mg, 183 mmol). LCMS: m/z 447 [M+1]+.

Example 109

3-Benzo[1,3]dioxol-5-yl-1-(1-methanesulfonyl-piperidin-4-yl)-7-methoxy-1H-pyrimido[5,4-c]quinoline-2,4-dione

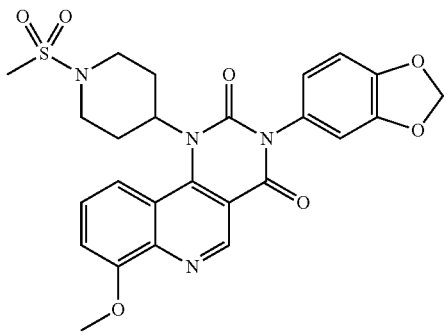 [SMILES: COc1cccc2c1ncc1c(=O)n(-c3ccc4c(c3)OCO4)c(=O)n(C3CCN(S(C)(=O)=O)CC3)c12]

3-Benzo[1,3]dioxol-5-yl-1-(1-methanesulfonyl-piperidin-4-yl)-7-methoxy-1H-pyrimido[5,4-c]quinoline-2,4-dione (45 mg) was prepared according to general procedure H from 3-Benzo[1,3]dioxol-5-yl-7-methoxy-1-piperidin-4-yl-1H-pyrimido[5,4-c]quinoline-2,4-dione.dihydrochloride (50 mg, 0.1 mmol) and methanesulfonyl chloride. LCMS: m/z 525 [M+1]+. $^1$H NMR (400 MHz, CDCl$_3$): δ 9.52 (s, 1H), 7.15 (m, 1H), 7.08 (m, 1H), 6.92 (m, 1H), 6.86 (m, 1H), 6.70-6.76 (m, 2H), 6.19 (s, 1H), 6.12 (s, 1H), 5.09 (m, 1H), 4.38 (m, 1H), 4.18 (m, 2H), 4.07 (s, 3H), 3.26 (m, 2H), 2.91 (m, 2H), 2.68 (m, 2H), 1.78 (m, 2H), 1.14 (t, 3H) ppm.

Example 110

3-(1-Cyclopentyl-7-methoxy-2,4-dioxo-1,4-dihydro-2H-pyrimido[5,4-c]quinolin-3-yl)-benzonitrile

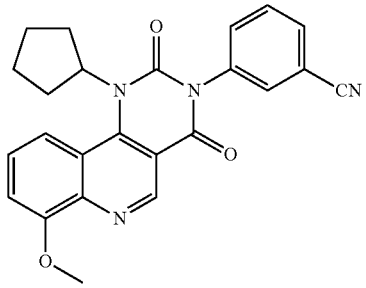 [SMILES: COc1cccc2c1ncc1c(=O)n(-c3cccc(C#N)c3)c(=O)n(C3CCCC3)c12]

3-(1-Cyclopentyl-7-methoxy-2,4-dioxo-1,4-dihydro-2H-pyrimido[5,4-c]quinolin-3-yl)-benzonitrile (19 mg) was prepared from 4-cyclopentylamino-8-methoxy-quinoline-3-carboxylic acid ethyl ester (0.1 mmol) and 3-isocyanato-benzonitrile (0.5 mmol) following general procedure C. LCMS: m/z 413 [M+1]+.

Example 111

1-Cyclopentyl-7-methoxy-3-(3-methylsulfanyl-phenyl)-1H-pyrimido[5,4-c]quinoline-2,4-dione

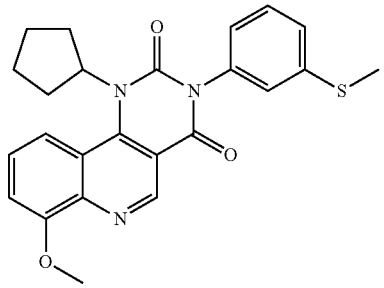 [SMILES: COc1cccc2c1ncc1c(=O)n(-c3cccc(SC)c3)c(=O)n(C3CCCC3)c12]

1-Cyclopentyl-7-methoxy-3-(3-methylsulfanyl-phenyl)-1H-pyrimido[5,4-c]quinoline-2,4-dione (28 mg) was prepared from 4-cyclopentylamino-8-methoxy-quinoline-3-carboxylic acid ethyl ester (0.1 mmol) and 1-isocyanato-3- methylsulfanyl-benzene (0.5 mmol) following general procedure C. LCMS: m/z 434 [M+1]⁺.

Example 112

1-Cyclopentyl-3-(3-methanesulfonyl-phenyl)-7-methoxy-1H-pyrimido[5,4-c]quinoline-2,4-dione

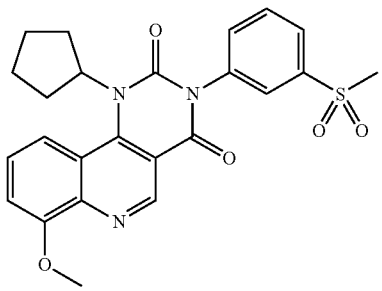 [SMILES: COc1cccc2c1ncc1c(=O)n(-c3cccc(S(C)(=O)=O)c3)c(=O)n(C3CCCC3)c12]

1-Cyclopentyl-3-(3-methanesulfonyl-phenyl)-7-methoxy-1H-pyrimido[5,4-c]quinoline-2,4-dione (21 mg) was prepared according to general procedure J from 1-cyclopentyl-7-methoxy-3-(3-methylsulfanyl-phenyl)-1H-pyrimido[5,4-c]quinoline-2,4-dione (21 mg, 0.5 mmol). LCMS: m/z 466 [M+1]⁺.

Example 113

3-[(R)-3-(3-Chloro-phenyl)-7-methoxy-2,4-dioxo-3,4-dihydro-2H-pyrimido[5,4-c]quinolin-1-yl]-pyrrolidine-1-carboxylic acid tert-butyl ester

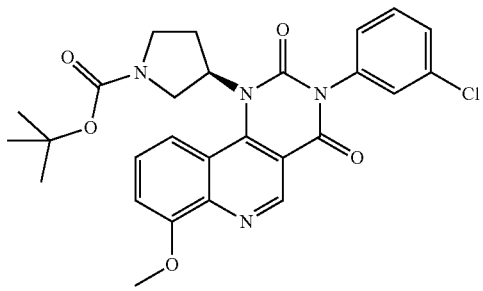 [SMILES: COc1cccc2c1ncc1c(=O)n(-c3cccc(Cl)c3)c(=O)n([C@@H]3CCN(C(=O)OC(C)(C)C)C3)c12]

4-Chloro-8-methoxy-quinoline-3-carboxylic acid ethyl ester (266 mg, 1.0 mmol) was treated with (R)-3-amino-pyrrolidine-1-carboxylic acid tert-butyl ester following general procedure B to afford 4-((R)-1-tert-butoxycarbonyl-pyrrolidin-3-ylamino)-8-methoxy-quinoline-3-carboxylic acid ethyl ester 381 mg). Thus obtained amino-ester (208 mg, 0.5 mmol) was subjected to reaction with 1-chloro-3-isocyanato-benzene according to general procedure C to furnish 3-[(R)-3-(3-chloro-phenyl)-7-methoxy-2,4-dioxo-3,4-dihydro-2H-pyrimido[5,4-c]quinolin-1-yl]-pyrrolidine-1-carboxylic acid tert-butyl ester (194 mg). LCMS: m/z 523 [M+1]⁺.

Example 114

(R)-3-(3-Chloro-phenyl)-7-methoxy-1-pyrrolidin-3-yl-1H-pyrimido[5,4-c]quinoline-2,4-dione.dihydrochloride

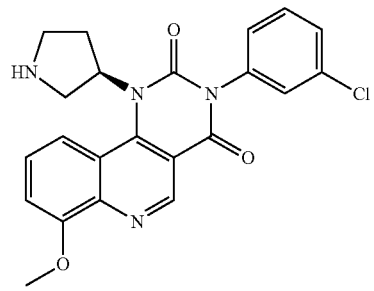 [SMILES: COc1cccc2c1ncc1c(=O)n(-c3cccc(Cl)c3)c(=O)n([C@@H]3CCNC3)c12]

(R)-3-(3-Chloro-phenyl)-7-methoxy-1-pyrrolidin-3-yl-1H-pyrimido[5,4-c]quinoline-2,4-dione.dihydrochloride (59 mg) was prepared according to general procedure G from 3-[(R)-3-(3-chloro-phenyl)-7-methoxy-2,4-dioxo-3,4-dihydro-2H-pyrimido[5,4-c]quinolin-1-yl]-pyrrolidine-1-carboxylic acid tert-butyl ester (105 mg, 0.2 mmol). LCMS: m/z 423 [M+1]⁺.

Example 115

3-(3-Chloro-phenyl)-1-((R)-1-methanesulfonyl-pyrrolidin-3-yl)-7-methoxy-1H-pyrimido[5,4-c]quinoline-2,4-dione

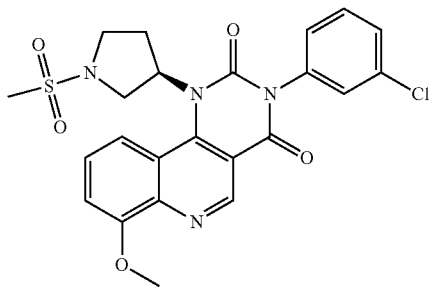 [SMILES: COc1cccc2c1ncc1c(=O)n(-c3cccc(Cl)c3)c(=O)n([C@@H]3CCN(S(C)(=O)=O)C3)c12]

3-(3-Chloro-phenyl)-1-((R)-1-methanesulfonyl-pyrrolidin-3-yl)-7-methoxy-1H-pyrimido[5,4-c]quinoline-2,4-dione (29 mg) was prepared according to general procedure H from (R)-3-(3-chloro-phenyl)-7-methoxy-1-pyrrolidin-3-yl- 1H-pyrimido[5,4-c]quinoline-2,4-dione.dihydrochloride (42 mg, 0.1 mmol) and methanesulfonyl chloride. LCMS: m/z 501 [M+1]+.

Example 116

3-[(S)-3-(3-Chloro-phenyl)-7-methoxy-2,4-dioxo-3,4-dihydro-2H-pyrimido[5,4-c]quinolin-1-yl]-pyrrolidine-1-carboxylic acid tert-butyl ester

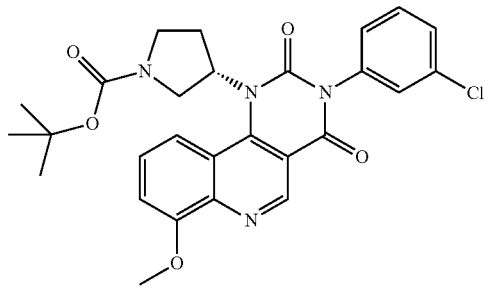 [SMILES: COc1cccc2c1ncc1c(=O)n(-c3cccc(Cl)c3)c(=O)n([C@H]3CCN(C(=O)OC(C)(C)C)C3)c12]

4-Chloro-8-methoxy-quinoline-3-carboxylic acid ethyl ester (266 mg, 1.0 mmol) was treated with (S)-3-amino-pyrrolidine-1-carboxylic acid tert-butyl ester following general procedure B to afford 4-((S)-1-tert-butoxycarbonyl-pyrrolidin-3-ylamino)-8-methoxy-quinoline-3-carboxylic acid ethyl ester (345 mg). Thus obtained amino-ester (208 mg, 0.5 mmol) was subjected to reaction with 1-chloro-3-isocyanato-benzene according to general procedure C to furnish 3-[(S)-3-(3-chloro-phenyl)-7-methoxy-2,4-dioxo-3,4-dihydro-2H-pyrimido[5,4-c]quinolin-1-yl]-pyrrolidine-1-carboxylic acid tert-butyl ester (177 mg). LCMS: m/z 523 [M+1]+.

Example 117

(S)-3-(3-Chloro-phenyl)-7-methoxy-1-pyrrolidin-3-yl-1H-pyrimido[5,4-c]quinoline-2,4-dione.dihydrochloride

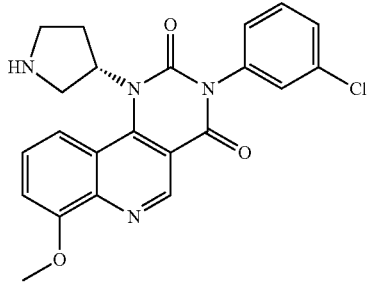 [SMILES: COc1cccc2c1ncc1c(=O)n(-c3cccc(Cl)c3)c(=O)n([C@H]3CCNC3)c12]

(S)-3-(3-Chloro-phenyl)-7-methoxy-1-pyrrolidin-3-yl-1H-pyrimido[5,4-c]quinoline-2,4-dione.dihydrochloride (53 mg) was prepared according to general procedure G from 3-[(S)-3-(3-chloro-phenyl)-7-methoxy-2,4-dioxo-3,4-dihydro-2H-pyrimido[5,4-c]quinolin-1-yl]-pyrrolidine-1-carboxylic acid tert-butyl ester (105 mg, 0.2 mmol). LCMS: m/z 423 [M+1]+.

Example 118

3-(3-Chloro-phenyl)-1-((S)-1-methanesulfonyl-pyrrolidin-3-yl)-7-methoxy-1H-pyrimido[5,4-c]quinoline-2,4-dione

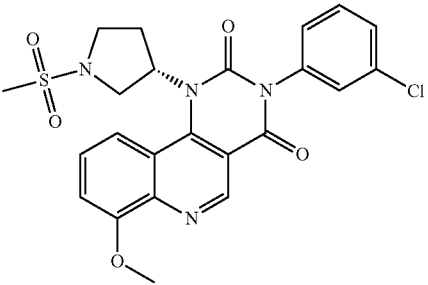 [SMILES: COc1cccc2c1ncc1c(=O)n(-c3cccc(Cl)c3)c(=O)n([C@H]3CCN(S(C)(=O)=O)C3)c12]

3-(3-Chloro-phenyl)-1-((S)-1-methanesulfonyl-pyrrolidin-3-yl)-7-methoxy-1H-pyrimido[5,4-c]quinoline-2,4-dione (27 mg) was prepared according to general procedure H from (S)-3-(3-chloro-phenyl)-7-methoxy-1-pyrrolidin-3-yl-1H-pyrimido[5,4-c]quinoline-2,4-dione.dihydrochloride (42 mg, 0.1 mmol) and methanesulfonyl chloride. LCMS: m/z 501 [M+1]+.

Example 119

3-Benzo[1,3]dioxol-5-yl-1-(2-methanesulfonyl-ethyl)-7-methoxy-1H-pyrimido[5,4-c]quinoline-2,4-dione

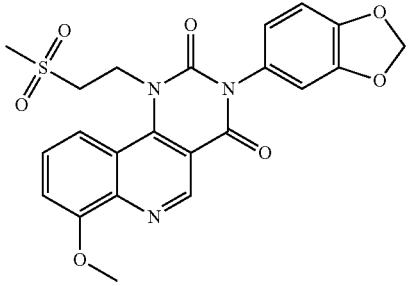 [SMILES: COc1cccc2c1ncc1c(=O)n(-c3ccc4c(c3)OCO4)c(=O)n(CCS(C)(=O)=O)c12]

4-Chloro-8-methoxy-quinoline-3-carboxylic acid ethyl ester (266 mg, 1.0 mmol) was treated with 2-methanesulfonyl-ethylamine following general procedure B to afford 4-(2-methanesulfonyl-ethylamino)-8-methoxy-quinoline-3-carboxylic acid ethyl ester (305 mg). Thus obtained amino-ester (70 mg, 0.2 mmol) was subjected to reaction with 5-Isocyanato-benzo[1,3]dioxole according to general procedure C to furnish 3-Benzo[1,3]dioxol-5-yl-1-(2-methanesulfonylethyl)-7-methoxy-1H-pyrimido[5,4-c]quinoline-2,4-dione (43 mg). LCMS: m/z 471 [M+1]+.

Example 120

1-Cyclopentyl-3-(2,3-dihydro-benzo[1,4]dioxin-6-yl)-7-methoxy-1H-pyrimido[5,4-c]quinoline-2,4-dione

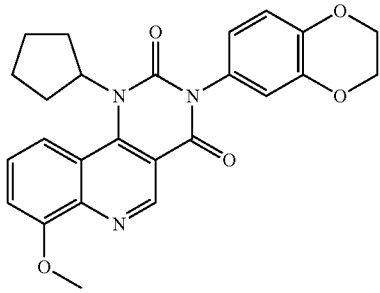 [SMILES: COc1cccc2c1ncc1c(=O)n(-c3ccc4c(c3)OCCO4)c(=O)n(C3CCCC3)c12]

1-Cyclopentyl-3-(2,3-dihydro-benzo[1,4]dioxin-6-yl)-7-methoxy-1H-pyrimido[5,4-c]quinoline-2,4-dione (18 mg) was prepared from 4-cyclopentylamino-8-methoxy-quinoline-3-carboxylic acid ethyl ester (0.1 mmol) and 6-isocyanato-2,3-dihydro-benzo[1,4]dioxine (0.5 mmol) following general procedure C. LCMS: m/z 446 [M+1]+.

Example 121

3-(3-Chloro-phenyl)-1-(1-ethanesulfonyl-piperidin-4-yl)-7-methoxy-1H-pyrimido[5,4-c]quinoline-2,4-dione

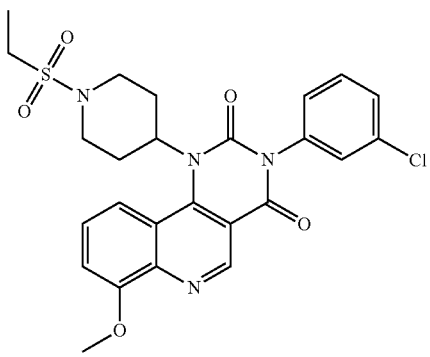 [SMILES: CCS(=O)(=O)N1CCC(n2c(=O)n(-c3cccc(Cl)c3)c(=O)c3cnc4c(OC)cccc4c32)CC1]

3-(3-Chloro-phenyl)-1-(1-ethanesulfonyl-piperidin-4-yl)-7-methoxy-1H-pyrimido[5,4-c]quinoline-2,4-dione (32 mg) was prepared according to general procedure H from 3-(3-chloro-phenyl)-7-methoxy-1-piperidin-4-yl-1H-pyrimido[5,4-c]quinoline-2,4-dione.dihydrochloride (40 mg) and ethanesulfonyl chloride. LCMS: m/z 529 [M+1]+.

Example 122

3-(3-Chloro-phenyl)-1-(1-methanesulfonylmethanesulfonyl-piperidin-4-yl)-7-methoxy-1H-pyrimido[5,4-c]quinoline-2,4-dione

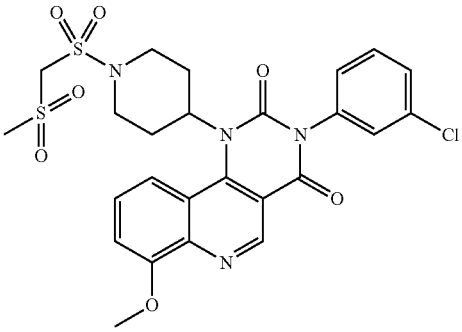 [SMILES: COc1cccc2c1ncc1c(=O)n(-c3cccc(Cl)c3)c(=O)n(C3CCN(S(=O)(=O)CS(C)(=O)=O)CC3)c12]

3-(3-Chloro-phenyl)-1-(1-ethanesulfonyl-piperidin-4-yl)-7-methoxy-1H-pyrimido[5,4-c]quinoline-2,4-dione (42 mg) was prepared according to general procedure H from 3-(3-chloro-phenyl)-7-methoxy-1-piperidin-4-yl-1H-pyrimido[5,4-c]quinoline-2,4-dione.dihydrochloride (40 mg) and methanesulfonylmethanesulfonyl chloride. LCMS: m/z 594 [M+1]+.

Example 123

4-[3-(3-Chloro-phenyl)-7-methoxy-2,4-dioxo-3,4-dihydro-2H-pyrimido[5,4-c]quinolin-1-yl]-piperidine-1-carboxylic acid methylamide

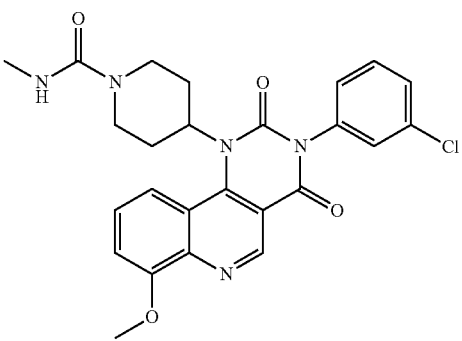 [SMILES: CNC(=O)N1CCC(n2c(=O)n(-c3cccc(Cl)c3)c(=O)c3cnc4c(OC)cccc4c32)CC1]

3-(3-Chloro-phenyl)-1-(1-ethanesulfonyl-piperidin-4-yl)-7-methoxy-1H-pyrimido[5,4-c]quinoline-2,4-dione (30 mg) was prepared by reacting 3-(3-chloro-phenyl)-7-methoxy-1-piperidin-4-yl-1H-pyrimido[5,4-c]quinoline-2,4-dione.dihydrochloride (75 mg) with carbonyldiimidazole and methylamine. LCMS: m/z 494 [M+1]+.

Example 124

4-[3-(3-Chloro-phenyl)-7-methoxy-2,4-dioxo-3,4-dihydro-2H-pyrimido[5,4-c]quinolin-1-yl]-piperidine-1-carboxylic acid methyl ester

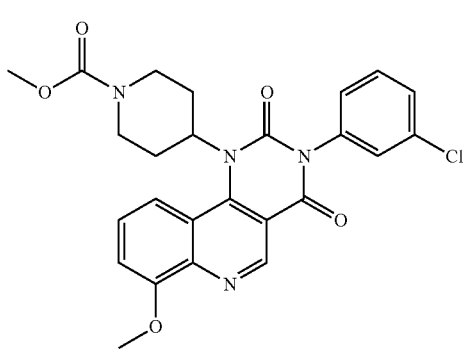 [SMILES: COC(=O)N1CCC(n2c(=O)n(-c3cccc(Cl)c3)c(=O)c3cnc4c(OC)cccc4c32)CC1]

4-[3-(3-Chloro-phenyl)-7-methoxy-2,4-dioxo-3,4-dihydro-2H-pyrimido[5,4-c]quinolin-1-yl]-piperidine-1-carboxylic acid methyl ester (35 mg) was prepared by reacting 3-(3-chloro-phenyl)-7-methoxy-1-piperidin-4-yl-1H-pyrimido[5,4-c]quinoline-2,4-dione.dihydrochloride (40 mg) with carbonyldiimidazole and methylamine. LCMS: m/z 495 [M+1]+.

Example 125

3-(3-2hloro-phenyl)-1-(1-methanesulfonyl-piperidin-4-yl)-7-methoxy-1H-pyrimido[5,4-c]quinoline-2,4-dione

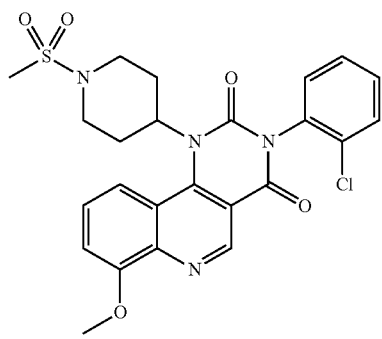 [SMILES: COc1cccc2c1ncc1c(=O)n(-c3ccccc3Cl)c(=O)n(C3CCN(S(C)(=O)=O)CC3)c12]

Title compound was prepared using the same procedures described for the preparation of 3-(3-chloro-phenyl)-1-(1-methanesulfonyl-piperidin-4-yl)-7-methoxy-1H-pyrimido[5,4-c]quinoline-2,4-dione. LCMS: m/z 515 [M+1]+.

Example 126

3-(3-Chloro-phenyl)-1-(1-methanesulfonyl-piperidin-4-ylmethyl)-7-methoxy-1H-pyrimido[5,4-c]quinoline-2,4-dione

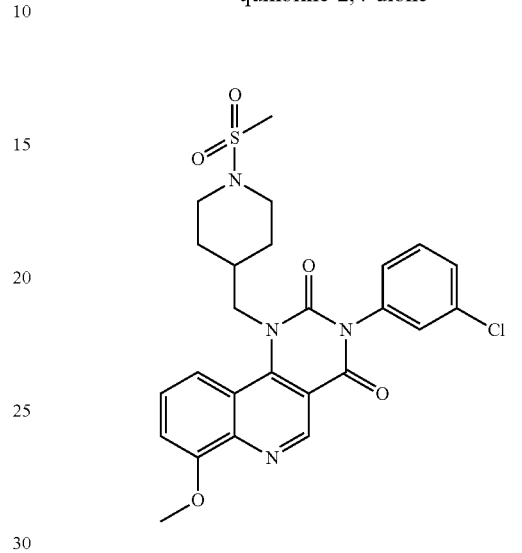

Title compound was prepared using the same procedures described for the preparation of 3-(3-chloro-phenyl)-1-(1-methanesulfonyl-piperidin-4-yl)-7-methoxy-1H-pyrimido[5,4-c]quinoline-2,4-dione using 4-aminomethyl-piperidine-1-carboxylic acid tert-butyl ester. LCMS: m/z 529 [M+1]+.

Example 127

N-{4-[(S)-3-(3-Chloro-phenyl)-7-methoxy-2,4-dioxo-3,4-dihydro-2H-pyrimido[5,4-c]quinolin-1-yl]-trans-cyclohexyl}-methanesulfonamide

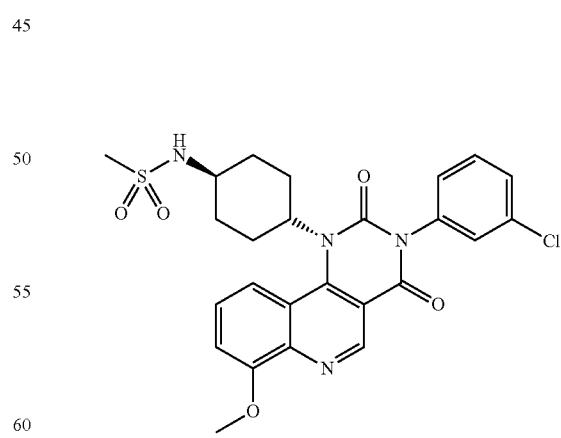

Title compound was prepared using the same procedures described for the preparation of 3-(3-chloro-phenyl)-1-(1-methanesulfonyl-piperidin-4-yl)-7-methoxy-1H-pyrimido[5,4-c]quinoline-2,4-dione using trans-(4-amino-cyclohexyl)-carbamic acid tert-butyl ester except the cyclization was carried out following general procedure K. LCMS: m/z 529 [M+1]$^+$.

Example 128

N-{3-[3-(3-Chloro-phenyl)-7-methoxy-2,4-dioxo-3,4-dihydro-2H-pyrimido[5,4-c]quinolin-1-yl]-propyl}-methanesulfonamide

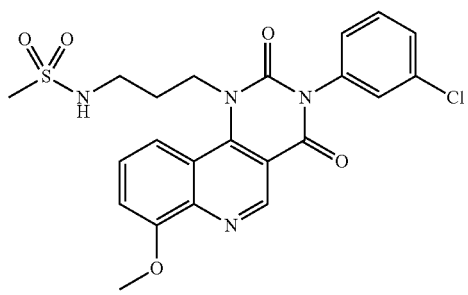 [SMILES: COc1cccc2c1ncc1c(=O)n(-c3cccc(Cl)c3)c(=O)n(CCCNS(C)(=O)=O)c12]

Title compound was prepared using the same procedures described for the preparation of 3-(3-chloro-phenyl)-1-(1-methanesulfonyl-piperidin-4-yl)-7-methoxy-1H-pyrimido[5,4-c]quinoline-2,4-dione except that the cyclization of amine-ester was carried out following general procedure K. LCMS: m/z 489 [M+1]$^+$.

Biological Examples

The compounds of the present invention include inhibitors of TNF-α synthesis. Compounds can be assayed in vitro for their ability to inhibit TNF-α accumulation in cell cultures. Inhibitor binding may also be measured by radiolabelling the inhibitor prior to binding, isolating the inhibitor or complex and determining the amount of radiolabel bound. Alternatively, inhibitor binding may be determined by running a competition experiment in which new inhibitors are incubated with a known radioligand. Compounds also can be assayed for their ability to affect cellular or physiological functions mediated by activity. Assays for each of these activities are described herein or are known in the art.

In general, embodiments of the present invention useful for pharmaceutical applications may have inhibitory potencies (IC$_{50}$'s) of interest of below about 100 μM. In an embodiment, embodiments of the present invention useful for pharmaceutical applications may have an IC$_{50}$ for a protein of interest of below about 50 μM. For particular applications, lower inhibitory potencies may be useful. Thus, in another embodiment, compounds of the present invention may inhibit TNF-α with an IC$_{50}$ in a range of less than 10 μM.

The compounds of the present invention elicit important and measurable pharmacological responses.

Human Whole Blood Assay

Blood is obtained by venipuncture from a healthy human donor. Preferably all donors are pre-screened for sexually transmitted disease as well as HIV and have been given a physical by a physician. Blood is drawn into 50 cc syringes containing 0.5 ml of sodium heparin (BD, 5000 U/mL). Typically each donor will give 100-150 ml of heparinized blood.

A third 50 cc syringe is collected without heparin. The non-heparinized blood is immediately evacuated into 5 to 6-8 ml clotting tubes (red-gray cap) containing a gel plug. (Becton Dickinson).

The clotted blood is separated by centrifugation at 1200×g for 15 minutes. The serum is removed, placed into a sterile tube and reserved.

Compounds are prepared as DMSO stocks. All compounds are prepared as 20 mM solutions and then serial diluted with DMSO. The final DMSO concentrations are not greater than 0.5% in the assay.

Compounds are added to a sterile deep-well polypropylene block (Corning) followed by 360 μL of heparinized blood. The blocks are covered with an adhesive foil strip then inverted to mix.

The blocks containing the compound and blood are placed into a 37° C. incubator for 30 minutes.

A stock of LPS using the reserved human serum is prepared. To prepare the stock, add 1 μL of LPS (5 mg/mL; Sigma Cat #L3024) to 5 mL of human serum. To each well added 40 μL of the serum containing LPS. Cover with foil and mix by inverting the block. If the blood fails to clot or shows extensive hemolysis, the LPS can be prepared in the same way using human Type AB serum (Cambrex).

After a 4-hour incubation at 37° C. the blocks are centrifuged at 1000×g to fully pellet the RBC.

The plasma is harvested and placed into a polypropylene 96 well plate and then stored at 4° C.

Samples are tested for TNF or other cytokines as per the manufacturer's instructions (TNF ELISA; R&D Systems, Cat #DY210). For TNF the samples are diluted 1:20 with PBS+1% BSA.

Human PBMC TNF Synthesis Assay

Human PBMC were obtained by from a healthy human donor leuko pak. Typically, all donors were pre-screened for STD, HIV and have been given a physical by a physician. One to two ampoules were thawed at 37° C. and then resuspended in 45 to 85 mL of RPMI+10% FBS to a final concentration of 2.5×10$^6$ cells/mL. Resuspended cells were filtered to remove any large clumps. (BD Falcon Cell strainer, 70 μM. Cat #352350) 00 μL of cells were added to each well of a 96-well tissue culture plate (Corning Costar #3595) and equilibrate in a humidified 5% CO$_2$ incubator at 37° C. for 30 minutes.

Prepare compounds for addition to cells: All compounds were DMSO stocks at 20 mM. Working stock for cell testing were prepared as 4× concentrated material in RPMI+10% FBS. Compounds were added to a polypropylene block and then diluted with the appropriate amount of RPMI+10% FBS. Typically 2.6 μL of 20 mM stock was diluted to 650 μL final volume to yield an 80 μM starting concentration in the stocks. RPMI was added to DMSO stock by pipetting into the tube or block. The compounds were then serial diluted with RPMI+10% FBS. The final DMSO concentrations were not greater than 0.5% in the assay.

Compounds were added to the cells as 4× working stock. 50 μL of compound was prepared above is added to the cells and re-equilibrated in a humidified 5% CO$_2$ incubator at 37° C. for 30 minutes.

A stock of LPS was prepared using RPMI+10% FBS. To prepare the stock, 2.8 μL of LPS (5 mg/mL; Sigma Cat #L3024) was added to 35 mL of media. 50 μL of the LPS in media was added to the cells. Control cultures without LPS received only RPMI+10% FBS. After an overnight incubation at 37° C., the cell culture supernatant was harvested and stored in a polypropylene 96 well plate.

Samples were tested for TNF as per the manufacturer's instructions (TNF ELISA; R&D Systems, Cat #DY210). The samples were serially diluted with PBS+1% BSA to the appropriate dilution condition for the cell prep, typically a 1:4 or 1:6 dilution.

TNF inhibition for select compounds of the present invention is shown in the table below:

| Ex. # | TNF inhib. (μM) | Ex. # | TNF inhib. (μM) | Ex. # | TNF inhib. (μM) |
|---|---|---|---|---|---|
| 1 | 0.18 | 4 | 14.2 | 5 | 0.27 |
| 10 | 0.41 | 16 | 0.68 | 17 | 0.39 |
| 18 | 1.1 | 28 | 3.5 | 29 | 0.92 |
| 30 | 2.5 | 32 | 2.6 | 33 | 20 |
| 34 | 3.6 | 37 | 20 | 38 | 0.45 |
| 39 | 1.3 | 41 | 0.5 | 45 | 0.2 |
| 46 | 1 | 47 | 0.9 | 48 | 1.4 |
| 51 | 0.03 | 54 | 0.006 | 55 | 0.163 |
| 72 | 0.004 | 73 | 0.009 | 75 | 0.006 |
| 78 | 0.001 | 83 | 0.001 | 84 | 0.002 |
| 87 | 0.002 | 88 | 0.001 | 89 | 0.005 |
| 90 | 0.002 | 91 | 0.001 | 92 | 0.0024 |
| 93 | 0.0004 | 94 | 0.0004 | 95 | 0.001 |
| 96 | 0.0004 | 97 | 0.0006 | 98 | 0.0003 |
| 99 | 0.02 | 100 | 0.0009 | 103 | 0.001 |
| 106 | 0.004 | 107 | 0.001 | 108 | 0.45 |
| 109 | 0.008 | 110 | 0.123 | 111 | 0.074 |
| 112 | 0.28 | 113 | 0.0003 | 114 | 0.031 |
| 115 | 0.029 | 116 | 0.002 | 117 | 1.0 |
| 118 | 0.029 | 120 | 0.24 | 124 | 50 |
| 126 | 0.002 | 127 | 0.006 | | |

Preparation of Human Peripheral Blood Mononuclear Cells from Donor Leuko Paks

Human donor leukopaks are obtained from normal, healthy human donors (Analytical Biological Services). Donor leukopaks are received by overnight delivery. All blood paks are shipped wrapped in cold packs and absorbent packing material.

The donor leukopak is opened aseptically in a hood using a scalpel or new razor blade cleaned with alcohol.

The donor cells are decanted into a 180 ml conical polypropylene tube (Nalgene Nunc #CS48; VWR#21020-500 or BD tube (VWR #21008-943). Typically a donor leukopak will yield 70-90 mL of cells.

The donation bag is backwashed with 50 mL of sterile Hanks Balanced Salts Solution (HBSS; Invitrogen w/o phenol red). Decant into cells.

Bring cell suspension to a final volume of 180 mL with HBSS at room temperature.

Add 30 mL of cell suspension to each of 6×50 mL conical tubes (Corning).

Underlay the cell suspension with 15 mL of Histopaque (Histopaque 1.077 g/mL; Sigma 10771) brought to room temperature. Use a 50 mL syringe and an 18 GA 6 inch spinal needle (BD #408360; 1.2 mM×152 mM; 18 GA) to underlay the histopaque taking care not to disturb the interface.

Centrifuge the tubes for 30 minutes at 400×g at room temperature. The brake should be turned off on the centrifuge.

Aspirate the media from the tubes taking care not to disturb the cells at the interface. Remove PBMC at the interface by aspiration taking care not to disturb the residual erythrocyte pellet.

Pool cells and resuspend to 200 mL. Split into 4×50 mL polypropylene tubes and centrifuge at 400×g for 10 minutes. Aspirate supernatant and resuspend cells in 100 mL of HBSS. Repeat centrifuge wash step 2×. Final pellets are resuspended in 50 mL of HBSS and filtered to remove any large clumps. (BD Falcon Cell strainer, 70 M. Cat #352350)

Cells are counted using a hemacytometer. Dilute 0.5 mL of cells in 9.5 mL of HBSS and count. Estimate cell number.

Pellet cells at 400×g for 10 minutes. Resuspend cells in fetal bovine serum (heat inactivated; Invitrogen) containing 6% DMSO to a final concentration of $1\times10^8$ cells/mL.

Aliquot cells to cryovials, 1 mL per vial.

Place cells into cell freezer blocks and place into −80° C. freezer overnight.

Remove cells from freezer and place cells into liquid nitrogen storage.

Prior to use of cells in compound profiling assays, determine the ability of the cells to respond to LPS (lipopolysaccharides from *Escherichia coli* 0111:B4; Sigma Cat#L3024, 5 mg resuspended in 1 mL of RPMI) and S100b (bovine S100b; Calbiochem, Cat#559290, resuspended in 1 mL of RPMI+10% FBS).

Thaw one ampoule of cells and resuspend in 40 mL of RPMI (ATCC; Cat #30-2001)+10% fetal bovine serum to a final concentration of $2.5\times10^6$ cells/mL.

Add 100 μL of cells to each well of a 96-well tissue culture plate (Corning Costar #3595) and equilibrate in a humidified 5% $CO_2$ incubator at 37° C. for 30 minutes.

Add 100 μL of RPMI+10% FBS with or without LPS (100 ng/mL) or S100 (20 ug/mL).

After an overnight incubation at 37° C., harvest the cell culture supernatant and store in a polypropylene 96 well plate at 4° C.

Samples are tested for TNF or other cytokines as per the manufacturers instructions (TNF ELISA; R&D Systems, Cat #DY210). The samples are serially diluted with PBS+1% BSA to find the proper dilution condition for the cell prep.

PDE4 Inhibition Assay

A TR-FRET-based phosphodiesterase assay kit from "Molecular Devices" was used to test whether these compounds were indeed direct inhibitors of the PDE4 enzyme. Using Roflumilast as a positive control, compounds of the present invention were tested against fluorescein-labeled cAMP substrate. The principle of the assay is based on the binding of a nucleotide monophosphate generated upon cAMP conversion to 5' AMP by PDE to an "IMAP binding reagent", which in turn is also ligated to a separate complex carrying terbium (Tb)-donor molecule. Proximity of the fluoreceinated 5'AMP to the Tb donor generates Fluorescence Resonance Energy Transfer. A PDE inhibitor will reduce the conversion of cAMP to 5'AMP, thus reducing monophosphate that can bind to the IMAP binding reagent and reduce the resulting FRET signal.

The following procedures were taken to obtain the experimental data described below:

The assay buffer was prepared by diluting 5× supplied Tween-based buffer in 1:5 in water to make 1× buffer. Add desired additive to buffer (DTT or $MnCl_2$). In a separate 96-well polypropylene plate, compound dilutions were prepared in assay buffer. Separate microcentrifuge tubes were prepared of PDE4B and PDE4D according to assay template—in assay buffer. The tubes were kept on ice. The enzyme concentration shown on the template were diluted by 1:4. FAM-cAMP substrate solution was prepared according to assay template. 5 μl compound was transferred from polypropylene plate into black 384-well plate. This plate was centrifuged briefly to make sure all 5 μl is on the bottom. Up to 80 μl of prepared PDE4B enzyme solution was transferred into alternate wells on row 'N' of 384-well plate starting from cell N1. Up to 80 μl of prepared PDE4D enzyme solution was transferred into alternate wells on row 'O' of 384-well plate, starting from cell O2. cAMP substrate solution was transferred into bottom row of separate 96-well plate. 5 μl of enzyme solution from the "reservoir" row (N or O) was transferred to each of the wells containing compounds, per layout map. Next, 10 μl of cAMP substrate was transferred to these wells. The order of substrate-first or enzyme-first can be switched depending on what is optimal. The final cAMP concentration was 100 nM in the reaction. 20 µl of assay buffer was pipetted into 4 separate wells—these are the blanks. The plate was sealed with an aluminum strip and incubated at 30° C. for 90 minutes. A TR-FRET solution was prepared. 4 ml of 1×IMAP Buffer A was added to 6 ml of IMAP Buffer B. 25 µl (⅛₀₀ of 20 ml) of binding beads was added to this and mix by inverting. 60 µl of this mixture was pipetted into 2 of the wells containing the "blank" assay buffer. Next, 49.7 µl (¼₀₀ of remaining volume) of Tb donor solution was added to the remaining TR-FRET solution and mixed by inverting. 60 µl of this solution was pipetted into remaining 2 "blank" assay buffer-containing wells. The TR-FRET solution was poured into a pipette boat and a multi-channel pipette was used to drop 60 µl of solution into all assay wells. The wells were covered with a foil strip and incubated for at least 3 hours or overnight protected from light (e.g. in a drawer) at room temperature. The plate was read on the Envision Reader: Emission 1: 520/Emission 2: 486/Exc: 340. Mirror: Umbelliferone (UV).

The data below was obtained by the procedure described above:

| Ex. # | PDE4B2 IC50 (nM) | PDE4D IC50 (nM) | Ex. # | PDE4B2 IC50 (nM) | PDE4D IC50 (nM) |
|---|---|---|---|---|---|
| 30 | 17000 | 25000 | 32 | 25000 | 25000 |
| 33 | 12400 | 25000 | 51 | 126 | 616 |
| 54 | 78 | 338 | 84 | 513 | 827 |
| 92 | 68 | 151 | 103 | 17 | 55 |
| 115 | 49 | 163 | 118 | 80 | 206 |
| 121 | 26 | 59 | 122 | 39 | 80 |
| 127 | 25 | 73 | | | |

The specific pharmacological responses observed may vary according to and depending on the particular active compound selected or whether there are present pharmaceutical carriers, as well as the type of formulation and mode of administration employed, and such expected variations or differences in the results are contemplated in accordance with practice of the present invention.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

We claim:

1. A method of treating chronic obstructive pulmonary disease (COPD) comprising administering to a human a compound of Formula (I) or a pharmaceutically acceptable salt thereof:

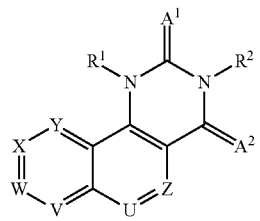

(I)

wherein:
$A^1$ is O or S;
$A^2$ is O or S;
U is N;
V is $C-(CH_2)_v R^V$;
W is $C-(CH_2)_w R^W$;
X is $C-(CH_2)_x R^X$;
Y is $C-(CH_2)_y R^Y$;
Z is $C-(CH_2)_z R^Z$;
$R^1$ is $-(CH_2)_q R^Q$;
$R^2$ is $-(CH_2)_s R^S$;
wherein
each of q, s, w, x, y, and z individually is 0, 1, 2, 3, or 4;
v is zero;
$R^Q$ is selected from the group consisting of:
  alkyl,
  cycloalkyl,
  phenyl,
  benzyl,
  tetrahydrofuranyl,
  tetrahydropyranyl,
  pyrrolidinyl,
  piperidinyl, and
  $-OR^8$, wherein
    the cycloalkyl is optionally substituted with one or more $R^c$;
    the phenyl and benzyl are each independently optionally substituted with one or more $R^a$; and
    the tetrahydrofuranyl, tetrahydropyranyl, pyrrolidinyl and piperidinyl are each independently optionally substituted with one or more $R^{hc}$;
$R^V$ is chloro or $-OCH_3$;
each of $R^S$, $R^W$, $R^X$, $R^Y$, and $R^Z$ is independently selected from the group consisting of
  alkyl;
  alkenyl;
  alkynyl;
  aryl;
  aryl substituted with one or more $R^a$;
  azido;
  cyano;
  cycloalkyl;
  cycloalkyl substituted with one or more $R^c$;
  fused cycloalkylaryl substituted with one or more $R^{f1}$;
  fused arylcycloalkyl substituted with one or more $R^{f2}$;
  fused heterocyclyaryl substituted with one or more $R^{f3}$;
  fused arylheterocyclyl substituted with one or more $R^{f4}$;
  fused cycloalkylheteroaryl substituted with one or more $R^{f5}$;
  fused heteroarylcycloalkyl substituted with one or more $R^{f6}$;
  fused heterocyclylheteroaryl substituted with one or more $R^{f7}$;
  halogen;
  haloalkyl;
  heterocyclyl;
  heterocyclyl substituted with one or more $R^{hc}$;
  heteroaryl;
  heteroaryl substituted with one or more $R^{ha}$;
  hydrogen;
  $-NR^3R^4$;
  $-C(O)NR^3R^4$;
  $-C(O)R^5$;
  $-C(O)_2R^6$;
  $-S(O)_jR^7$;

—OR$^8$; and
nitro;
wherein
- each of R$^3$ and R$^4$ is independently selected from the group consisting of H, acyl, alkyl, alkoxy, alkoxyalkyl, alkylsulfonyl, aryl, cycloalkyl, heterocyclyl and heteroaryl;
- j is 0, 1, or 2;
- each R$^5$, R$^6$, R$^7$, and R$^8$ is independently selected from the group consisting of
  - hydrogen;
  - alkyl;
  - alkenyl;
  - alkynyl;
  - alkoxy;
  - aryl;
  - aryl substituted with one or more R$^a$;
  - cycloalkyl;
  - cycloalkyl substituted with one or more R$^c$;
  - halogen;
  - haloalkyl;
  - heterocyclyl;
  - heterocyclyl substituted with one or more R$^{hc}$;
  - heteroaryl; and
  - heteroaryl substituted with one or more R$^{ha}$;
  - wherein each of R$^a$, R$^c$, R$^{f1}$, R$^{f2}$, R$^{f3}$, R$^{f4}$, R$^{f5}$, R$^{f6}$, R$^{f7}$, R$^{hc}$ and R$^{ha}$ is independently selected from the group consisting of acyl, alkyl, alkenyl, alkynyl, alkoxy, amide, amino, aryl, cyano, cycloalkyl, halogen, haloalkyl, haloalkoxy, heteroaryl, hydroxy, nitro, —C(O)OR$^9$, —SO$_2$R$^{10}$, —SR$^{11}$, —C(O)R$^{12}$, —C(O)NR$^{13}$, —NH—SO$_2$—R$^{14}$, —SO$_2$—NR$^{15}$R$^{16}$, and —SO$_2$—CH$_2$—SO$_2$—CH$_3$; and wherein
  - each of R$^9$, R$^{10}$, R$^{11}$, R$^{12}$, R$^{13}$ R$^{14}$, R$^{15}$, and R$^{16}$ is independently selected from the group consisting of hydrogen, alkyl, alkenyl, alkynyl, aryl, cycloalkyl, heterocyclyl, and heteroaryl.

2. The method of claim 1, wherein A$^1$ and A$^2$ are each O.

3. The method of claim 1, wherein R$^X$ is halogen or hydrogen and x is zero.

4. The method of claim 1, wherein R$^1$ is cycloalkyl or cycloalkyl substituted with one or more R$^c$.

5. The method of claim 4, wherein the cycloalkyl is cyclopentyl or cyclohexyl substituted with one or more R$^c$.

6. The method of claim 1, wherein R$^S$ is selected from the group consisting of
- hydrogen,
- alkyl,
- cycloalkyl,
- phenyl,
- benzyl,
- furanyl,
- thiophenyl,
- isoxazolyl,
- benzodioxolyl, and
- indanyl,
- —C(O)R$^5$,
- —C(O)$_2$R$^6$, and
- —OR$^8$, wherein
  - the cycloalkyl is optionally substituted with one or more R$^c$;
  - the phenyl and benzyl are each independently optionally substituted with one or more R$^a$; and
  - the furanyl, thiophenyl, isoxazolyl, benzodioxolyl, and indanyl, are each independently optionally substituted with one or more R$^{ha}$.

7. The method of claim 6, wherein R$^2$ is phenyl substituted with one or more R$^a$, and R$^a$ is halogen.

8. The method of claim 7, wherein R$^2$ is 3-chlorophenyl.

9. The method of claim 8, wherein R$^1$ is a 4-substituted cyclohexyl group.

10. The method of claim 9, wherein R$^1$ is trans-4-cyclohexanecarboxylic acid.

11. The method of claim 10, wherein the compound is in the form of a hydrochloric acid salt.

* * * * *